US006864259B2

(12) United States Patent
Ellsworth et al.

(10) Patent No.: US 6,864,259 B2
(45) Date of Patent: Mar. 8, 2005

(54) ANTIBACTERIAL AGENTS

(75) Inventors: Edmund Lee Ellsworth, Brighton, MI (US); Kim Marie Hutchings, Ann Arbor, MI (US); Dai Nguyen, Edmonton (CA); Rajeshwar Singh, Edmonton (CA); Howard Daniel Hollis Showalter, Ann Arbor, MI (US)

(73) Assignee: Warner-Lambert Company, Morris Plains, NJ (US)

( * ) Notice: Subject to any disclaimer, the term of this patent is extended or adjusted under 35 U.S.C. 154(b) by 2 days.

(21) Appl. No.: 10/157,370

(22) Filed: May 29, 2002

(65) Prior Publication Data

US 2003/0114458 A1 Jun. 19, 2003

Related U.S. Application Data

(60) Provisional application No. 60/365,077, filed on Mar. 19, 2002, and provisional application No. 60/294,338, filed on May 30, 2001.

(51) Int. Cl.$^7$ .................... C07D 471/04; C07D 487/04; A61K 31/519

(52) U.S. Cl. ........................... 514/252.16; 514/255.05; 514/259.4; 514/259.41; 514/228.2; 514/233.2; 544/282; 544/61; 544/116; 544/119

(58) Field of Search .......................... 544/282, 61, 116, 544/119; 514/252.16, 255.05, 259.4, 259.41, 228.2, 233.9

(56) References Cited

FOREIGN PATENT DOCUMENTS

| EP | 35619 A | 9/1981 |
|---|---|---|
| GB | 2097784 A | 11/1982 |
| WO | WO 9414809 A | 7/1994 |
| WO | WO 9422449 A | 10/1994 |
| WO | WO 9510519 A | 4/1995 |
| WO | WO 9818781 A | 5/1998 |
| WO | WO 9921840 A | 5/1999 |
| WO | WO 9961444 A | 12/1999 |
| WO | WO 0153273 A | 7/2001 |

OTHER PUBLICATIONS

Hunger et al., CAPLUS Abstract 52:50662, 1958.*
Garcia–Quintana, H.G., et al., Study of benzotriazepines and quinazolines obtained by synthesis on bacterial populations, J. Vet. Med., Series B, vol. 34(5): 341–346 (1987).
Kornet, M.J., et al., Synthesis of 3–amino–2–4 (1H, 3H)–quinazolinediones for testing as anticonvulsants, J. Hetero. Chem., vol. 21(5): 1533–1535 (1984).
Langis, C., The synthesis of 1,3,4–benzotriazepine–1H–2, 5–diones, Chim. Ther., vol. 2: 349–351 (1967).
Peet, N.P., et al., Synthesis of 3,4–dihydro–1H–1,3,4–benzotriazepine, 2,5–diones, J. Org. Chem., vol. 40(13):1909–1914 (1975).

Baronnet, R., et al., Synthesis and pharmacodynamics of 3–dialkylamino–1H, 3H–quinazoline–2,4–diones and derivatives, Eur. J. Med. Chem. —Chim. Ther., vol. 18(3):241–247 (1983).
Davidson, J.S., The preparation of 5–(2–aminophenyl)–1,3, 4–oxadiazol–2(3H)–one and its rearrangement to 3–amino–2,4(1H,3H)–quinazolinedione, Moatshefte fur Chem., vol. 115(5):565–572 (1984).
Zhuo, J–C., et al., Boron–containing heterocycles: Syntheses, Structures, and Benzoborauracil Nucleoside, J. Org. Chem., vol. 64(26):9566–9574 (1999).
Database Caplus, Chemical Abstract Service, AN—1998:699954; Bull. Korean Chem. Soc., vol. 19(10):1117–1119 (1998).
Database Caplus, Chemical Abstract Service, AN—1996:275827; J. Hetero. Chem., vol. 33(4):1131–1135 (1996).
Database Caplus, Chemical Abstract Service, AN—1977:468311; J. Org. Chem., vol. 45(15):2551–2556 (1997).
Database Caplus, Chemical Abstrat Service, AN—1968:2872; Helv. Chim. Acta., vol. 50(7):2019–2022 (1968).
Herold, et al., Synthesis and structure of novel 4–arylehexahydro–1H, 3H–pyrido '1,2–olpyrimidine derivatives, Journal of Heterocyclic Chemistry, Heterocorporation. Provo., US, Vo. 36(2): 389–396 (1999).
Database Crossfile, Beilstein Reg. No. 214132 (1910); Chem. Berich., vol. 43:1236 (1910).
Database Crossfile, Beistein Reg. No. 657750 (1965); Chem. Berich., vol. 98:1505–1510 (1965).
Database Crossfile, Beilstein Reg. No. 169392 (1967); Chem. Ther., vol. 2:1236 (1967).
Database Caplus, Chemical Abstract Service, AN—1997:522336; Arch. Pharm., vol. 330(5): 129–134 (1997).

(List continued on next page.)

Primary Examiner—Deepak Rao
(74) Attorney, Agent, or Firm—Heidi M. Berven; Robert N. Young

(57) ABSTRACT

The present invention provides compounds of Formula (I):

I

[structure with $R_1$–$R_6$ and K substituents on a bicyclic ring system]

wherein $R_1$–$R_6$ and K have any of the values defined in the specification, and pharmaceutically acceptable salt thereof, that are useful as antibacterial agents. Also disclosed are pharmaceutical compositions comprising one or more compounds of Formula I, processes for preparing compounds of Formula I, and intermediates useful for preparing compounds of Formula I.

26 Claims, No Drawings

OTHER PUBLICATIONS

Database Crossfire Beilstein, Accession No. 8138 (Abstract) Robins, Hitchings: J. Amer. Chem. Soc., vol. 77, p. 2256 (1955).

Database Crossfire Beilstein, Accession No. 157768 (Abstract) Chatterjee, Anand: J. Sci. Ind. Res., vol 17B, p. 63 (1958).

Database Crossfire Beilstein, Accession No. 383776 (Abstract) Jacini: Gazz. Chim. Ital., vol. 73, p. 85 (1943).

Database Crossfire Beilstein, Accession No. 1198342 & 1174334 (Abstract) K. Grohe, H. Heitzer: Justus Liebigs Ann. chem., p. 2066–2073 (1974).

Chemical Abstracts, Abstract No. 233993w, vol. 118:23 (Jun. 7, 1993).

Chemical Abstracts, Abstract No. 339967j, vol. 123:25 (Dec. 18, 1995).

Chemical Abstracts, Abstract No. 17901h, vol. 127:2 (Jul. 14, 1997).

Chemical Abstracts, Abstract No. 34737x, vol. 128:4 (Jan. 26, 1998).

Chemical Abstracts, Abstract No. 237941k, vol. 133:17 (Oct. 23, 2000).

* cited by examiner

ANTIBACTERIAL AGENTS

CROSS REFERENCE TO RELATED APPLICATIONS

This is a utility application which claims the benefit of priority from U.S. Provisional Application Nos. 60/294,338 filed on May 30, 2001 and 60/365,077 filed on Mar. 19, 2002.

FIELD OF THE INVENTION

This invention relates to antibacterial agents having a pyrido[1,2-c]pyrimidine core structure and methods for their use.

BACKGROUND OF THE INVENTION

Antibiotic resistance is a worldwide problem with catastrophic potential. A Task Force co-chaired by the United States Centers for Disease Control (CDC), Food and Drug Administration (FDA), and National Institutes of Health (NIH) recently addressed this important issue, observing that drug resistant pathogens are a growing menace to all people, regardless of race, age, gender, or socioeconomic background. The Task Force noted that a number of microbes responsible for infections in humans are rapidly developing resistance to existing drugs. For example, according to the Task Force, in the United States alone, up to 30 percent of the *Staphylococcus pneumoniae* infections (skin, bone, lung, and bloodstream infections) are no longer susceptible to penicillin in some areas. Up to 11 percent of *S. pneumoniae* are resistant to third generation cephalosporin antibiotics. Significantly, resistance of *S. pneumoniae* to the fluoroquinolones, a newer class of potent antibiotics, has also been reported.

Exemplified by ciprofloxacin A, the fluoroquinolones are bacterial inhibitors that apparently exert their effect by inhibiting DNA gyrase and topoisomerase IV.

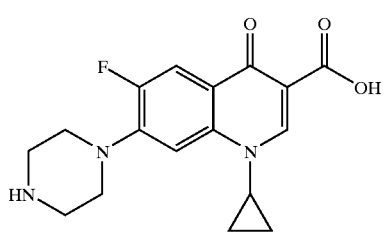

A

The consequences of antibiotic resistance, particularly fluoroquinolone resistance, can be fatal for some individuals. In a case reported from Denmark, a 62-year-old woman diagnosed with food poisoning from ciprofloxacin-resistant *Salmonella* died after undergoing antibiotic treatment using that drug.

The dramatic and lethal emergence of antibiotic resistance typified by this and other reports has spurred the U.S. Task Force to call for the implementation of a public health action plan to combat antimicrobial resistance. As a vital component of that plan, there is a need for the development of new products that will prevent the continued emergence of antibiotic resistance generally, and that will prevent and treat colonization and infection of resistant organisms in patients.

SUMMARY OF THE INVENTION

The present invention provides compounds having pyrido [1,2-c] pyrimidine core structures that meet these and other needs. Accordingly, there is provided a compound of the invention which is a compound of Formula I:

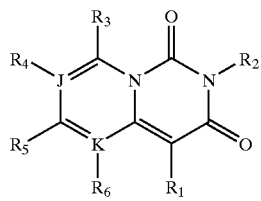

I or a pharmaceutically acceptable salt thereof wherein:
$R_1$ is H,
 $C_1$–$C_7$ alkyl and substituted alkyl,
 $C_2$–$C_7$ alkenyl and substituted alkenyl,
 $C_2$–$C_7$ alkynyl and substituted alkynyl,
 $C_3$–$C_7$ cycloalkyl and substituted cycloalkyl,
 aryl and substituted aryl,
 heterocyclic and substituted heterocyclic,
 or heteroaryl and substituted heteroaryl;
$R_2$ is H,
 $C_1$–$C_7$ alkyl and substituted alkyl,
 $C_2$–$C_7$ alkenyl and substituted alkenyl,
 $C_2$–$C_7$ alkynyl and substituted alkynyl,
 $C_3$–$C_7$ cycloalkyl and substituted cycloalkyl,
 aryl and substituted aryl,
 heterocyclic and substituted heterocyclic,
 heteroaryl and substituted heteroaryl,
 halo,
 $NO_2$,
 NO,
 CN,
 $OR_a$,

wherein $R_a$ is H,
 $C_1$–$C_7$ alkyl and substituted alkyl,
 $C_2$–$C_7$ alkenyl and substituted alkenyl,
 $C_3$–$C_7$ cycloalkyl and substituted cycloalkyl,
 aryl and substituted aryl,
 heteroaryl and substituted heteroaryl,
 heterocycloalkyl and substituted heterocycloalkyl,

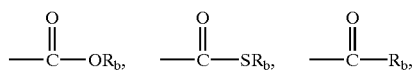

wherein $R_b$ is H,
 $C_1$–$C_7$ alkyl and substituted alkyl,
 $C_2$–$C_7$ alkenyl and substituted alkenyl,
 $C_3$–$C_7$ cycloalkyl and substituted cycloalkyl,
 aryl and substituted aryl,
 heteroaryl and substituted heteroaryl,
 heterocycloalkyl and substituted heterocycloalkyl;

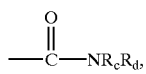

wherein $R_c$ and $R_d$ are independantly H,
 $C_1$–$C_7$ alkyl and substituted alkyl,
 $C_2$–$C_7$ alkenyl and substituted alkenyl, $C_3$–$C_7$ cycloalkyl and substituted cycloalkyl,
aryl and substituted aryl,
heteroaryl and substituted heteroaryl,
heterocycloalkyl and substituted heterocycloalkyl;
$NR_eR_f$, wherein
  $R_e$ and $R_f$ are each independently H,
  $C_1$–$C_7$ alkyl and substituted alkyl,
  $C_2$–$C_7$ alkenyl and substituted alkenyl,
  $C_2$–$C_7$ alkynyl and substituted alkynyl,
  $C_3$–$C_7$ cycloalkyl and substituted cycloalkyl,
  $C_5$–$C_8$ cycloalkenyl and substituted cycloalkenyl,
  aryl and substituted aryl, or

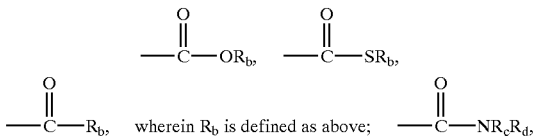

wherein $R_b$ is defined as above;

wherein $R_c$ and $R_d$ are defined as above;
aryl and substituted aryl,
heteroaryl and substituted heteroaryl,
heterocycloalkyl and substituted heterocycloalkyl, or
$R_e$ and $R_f$ are taken together with the nitrogen to which they are attached form a 4, 5, 6, 7, or 8 membered ring having from 0 to 3 heteroatoms selected from N, O, and S, wherein said ring is optionally substituted by one or more substituents;
$R_3$, $R_4$, and $R_6$ independently are H,
  OH,
  $(O)_nC_1$–$C_7$ alkyl and substituted alkyl,
  $(O)_nC_2$–$C_7$ alkenyl and substituted alkenyl,
  $(O)_nC_2$–$C_7$ alkynyl and substituted alkynyl,
wherein n is 0 or 1,
  halo,
  $NO_2$,
  CN,
  $NR_eR_f$, wherein $R_e$ and $R_f$ are defined as above; or
$R_1$ and $R_6$ taken together with the atoms to which they are attached form a 5, 6, 7, or 8 membered ring having from 0 to 3 heteroatoms selected from N, O, and S, wherein said ring is optionally substituted by one or more substituents;
$R_5$ is hydrogen,
  $C_1$–$C_7$ alkyl and substituted alkyl,
  $C_2$–$C_7$ alkenyl and substituted alkenyl,
  $C_2$–$C_7$ alkynyl and substituted alkynyl,
  $OR_a$, wherein $R_a$ is defined as above,

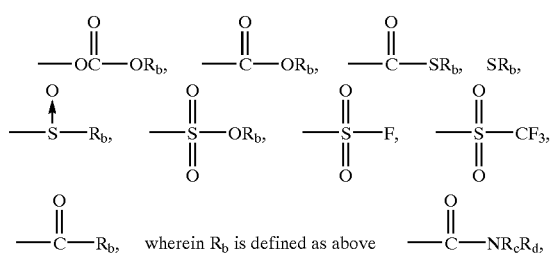

wherein $R_b$ is defined as above    wherein $R_c$ and $R_d$ are defined as above;
halo,
$NO_2$,
CN,
$NR_eR_f$, wherein $R_e$ and $R_f$ are defined as above;
aryl or fused aryl,
heterocyclic or fused heterocyclic,
heteroaryl or fused heteroaryl,
bicyclic heterocyclic or spiro heterocyclic,
  wherein fused aryl, fused heterocyclic, fused heteroaryl, bicyclic heterocyclic, or spiro heterocyclic can be substituted; and
  wherein J and K independently are C or N, provided that when J or K is N, $R_4$ or $R_6$ is absent at that position.
The invention also provides a compound of Formula II;

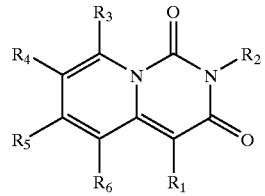

II or a pharmaceutically acceptable salt thereof wherein:
$R_1$ is H,
  $C_1$–$C_7$ alkyl and substituted alkyl,
  $C_2$–$C_7$ alkenyl and substituted alkenyl,
  $C_2$–$C_7$ alkynyl and substituted alkynyl,
  $C_3$–$C_7$ cycloalkyl and substituted cycloalkyl,
  aryl and substituted aryl,
  heterocyclic and substituted heterocyclic,
  or heteroaryl and substituted heteroaryl;
$R_2$ is H,
  $C_1$–$C_7$ alkyl and substituted alkyl,
  $C_2$–$C_7$ alkenyl and substituted alkenyl,
  $C_2$–$C_7$ alkynyl and substituted alkynyl,
  $C_3$–$C_7$ cycloalkyl and substituted cycloalkyl,
  aryl and substituted aryl,
  heterocyclic and substituted heterocyclic,
  heteroaryl and substituted heteroaryl,
  halo,
  $NO_2$,
  NO,
  CN,
  $OR_a$,

wherein $R_a$ is H,
  $C_1$–$C_7$ alkyl and substituted alkyl,
  $C_2$–$C_7$ alkenyl and substituted alkenyl,
  $C_3$–$C_7$ cycloalkyl and substituted cycloalkyl,
  aryl and substituted aryl,
  heteroaryl and substituted heteroaryl,
  heterocycloalkyl and substituted heterocycloalkyl,

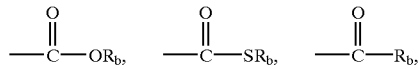

wherein $R_b$ is H,
  $C_1$–$C_7$ alkyl and substituted alkyl,
  $C_2$–$C_7$ alkenyl and substituted alkenyl,
  $C_3$–$C_7$ cycloalkyl and substituted cycloalkyl,
  aryl and substituted aryl, heteroaryl and substituted heteroaryl,
heterocycloalkyl and substituted heterocycloalkyl;

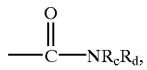

wherein $R_c$ and $R_d$ are independantly H,
  $C_1$–$C_7$ alkyl and substituted alkyl,
  $C_2$–$C_7$ alkenyl and substituted alkenyl,
  $C_3$–$C_7$ cycloalkyl and substituted cycloalkyl,
  aryl and substituted aryl,
  heteroaryl and substituted heteroaryl,
  heterocycloalkyl and substituted heterocycloalkyl;
$NR_eR_f$, wherein
  $R_e$ and $R_f$ are each independently H,
  $C_1$–$C_7$ alkyl and substituted alkyl,
  $C_2$–$C_7$ alkenyl and substituted alkenyl,
  $C_2$–$C_7$ alkynyl and substituted alkynyl,
  $C_3$–$C_7$ cycloalkyl and substituted cycloalkyl,
  $C_5$–$C_8$ cycloalkenyl and substituted cycloalkenyl,
  aryl and substituted aryl, or

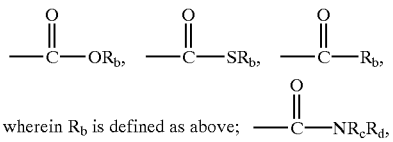

wherein $R_b$ is defined as above;

wherein $R_c$ and $R_d$ are defined as above;
aryl and substituted aryl,
heteroaryl and substituted heteroaryl,
heterocycloalkyl and substituted heterocycloalkyl, or
$R_e$ and $R_f$ taken together with the nitrogen to which they are attached form a 4, 5, 6, 7, or 8 membered ring having from 0 to 3 heteroatoms selected from N, O, and S, wherein said ring is optionally substituted by one or more substituents;
$R_3$, $R_4$, and $R_6$ independently are H,
  OH,
  $(O)_nC_1$–$C_7$ alkyl and substituted alkyl,
  $(O)_nC_2$–$C_7$ alkenyl and substituted alkenyl,
  $(O)_nC_2$–$C_7$ alkynyl and substituted alkynyl,
wherein n is 0 or 1,
  halo,
  $NO_2$,
  CN,
  $NR_eR_f$, wherein $R_e$ and $R_f$ are defined as above; or
$R_1$ and $R_6$ taken together with the atoms to which they are attached form a 5, 6, 7, or 8 membered ring having from 0 to 3 heteroatoms selected from N, O, and S, wherein said ring is optionally substituted by one or more substituents;
$R_5$ is hydrogen,
  $C_1$–$C_7$ alkyl and substituted alkyl,
  $C_2$–$C_7$ alkenyl and substituted alkenyl,
  $C_2$–$C_7$ alkynyl and substituted alkynyl,
$OR_a$, wherein $R_a$ is defined as above,

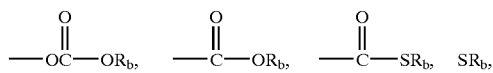

-continued

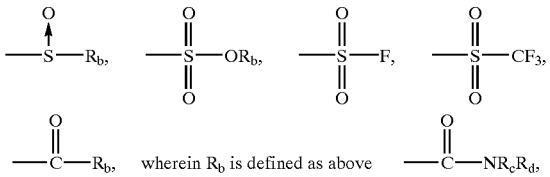

wherein $R_c$ and $R_d$ are defined as above;
halo,
$NO_2$,
CN,
$NR_eR_f$, wherein $R_e$ and $R_f$ are as defined above,
aryl or fused aryl,
heterocyclic or fused heterocyclic,
heteroaryl or fused heteroaryl, or
bicyclic heterocyclic or spiro heterocyclic,
  wherein fused aryl, fused heterocyclic, fused heteroaryl, bicyclic heterocyclic, or spiro heterocyclic can be substituted.

The invention also provides a compound of Formula III:

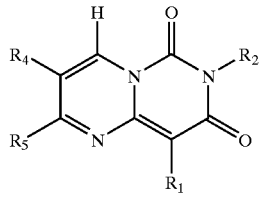

III or a pharmaceutically acceptable salt thereof, wherein:
$R_1$ is H,
  $C_1$–$C_7$ alkyl and substituted alkyl,
  $C_2$–$C_7$ alkenyl and substituted alkenyl,
  $C_2$–$C_7$ alkynyl and substituted alkynyl,
  $C_3$–$C_7$ cycloalkyl and substituted cycloalkyl,
  aryl and substituted aryl,
  heterocyclic and substituted heterocyclic,
  or heteroaryl and substituted heteroaryl;
$R_2$ is H,
  $C_1$–$C_7$ alkyl and substituted alkyl,
  $C_2$–$C_7$ alkenyl and substituted alkenyl,
  $C_2$–$C_7$ alkynyl and substituted alkynyl,
  $C_3$–$C_7$ cycloalkyl and substituted cycloalkyl,
  aryl and substituted aryl,
  heterocyclic and substituted heterocyclic,
  heteroaryl and substituted heteroaryl,
  halo,
  $NO_2$,
  NO,
  CN,
  $OR_a$,

wherein $R_a$ is H,
  $C_1$–$C_7$ alkyl and substituted alkyl,
  $C_2$–$C_7$ alkenyl and substituted alkenyl,
  $C_3$–$C_7$ cycloalkyl and substituted cycloalkyl,
  aryl and substituted aryl, heteroaryl and substituted heteroaryl,
heterocycloalkyl and substituted heterocycloalkyl,

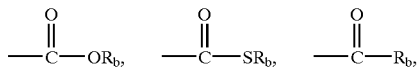

wherein $R_b$ is H,
$C_1$–$C_7$ alkyl and substituted alkyl,
$C_2$–$C_7$ alkenyl and substituted alkenyl,
$C_3$–$C_7$ cycloalkyl and substituted cycloalkyl,
aryl and substituted aryl,
heteroaryl and substituted heteroaryl,
heterocycloalkyl and substituted heterocycloalkyl;

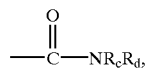

wherein $R_c$ and $R_d$ are independantly H,
$C_1$–$C_7$ alkyl and substituted alkyl,
$C_2$–$C_7$ alkenyl and substituted alkenyl,
$C_3$–$C_7$ cycloalkyl and substituted cycloalkyl,
aryl and substituted aryl,
heteroaryl and substituted heteroaryl,
heterocycloalkyl and substituted heterocycloalkyl;
$NR_eR_f$, wherein
$R_e$ and $R_f$ are each independently H,
$C_1$–$C_7$ alkyl and substituted alkyl,
$C_2$–$C_7$ alkenyl and substituted alkenyl,
$C_2$–$C_7$ alkynyl and substituted alkynyl,
$C_3$–$C_7$ cycloalkyl and substituted cycloalkyl,
$C_5$–$C_8$ cycloalkenyl and substituted cycloalkenyl,
aryl and substituted aryl, or

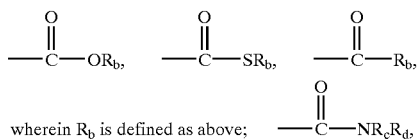

wherein $R_b$ is defined as above;

wherein $R_c$ and $R_d$ are defined as above;
aryl and substituted aryl,
heteroaryl and substituted heteroaryl,
heterocycloalkyl and substituted heterocycloalkyl, or
$R_e$ and $R_f$ are taken together with the nitrogen to which they are attached form a 4, 5, 6, 7, or 8 membered ring having from 0 to 3 heteroatoms selected from N, O, and S, wherein said ring is optionally substituted by one or more substituents;
$R_4$ is H,
OH,
$(O)_nC_1$–$C_7$ alkyl and substituted alkyl,
$(O)_nC_2$–$C_7$ alkenyl and substituted alkenyl,
$(O)_nC_2$–$C_7$ alkynyl and substituted alkynyl,
wherein n is 0 or 1,
halo,
$NO_2$,
CN,
$NR_eR_f$, wherein $R_e$ and $R_f$ are defined as above;
$R_5$ is hydrogen,
$C_1$–$C_7$ alkyl and substituted alkyl,
$C_2$–$C_7$ alkenyl and substituted alkenyl, $C_2$–$C_7$ alkynyl and substituted alkynyl,
$OR_a$, wherein $R_a$ is defined as above,

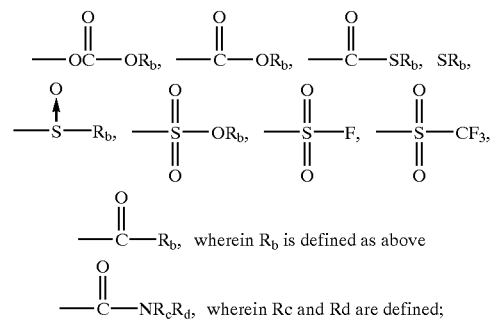

wherein $R_c$ and $R_d$ are defined as above;
halo,
$NO_2$,
CN,
$NR_eR_f$, wherein $R_e$ and $R_f$ are defined as above,
aryl or fused aryl,
heterocyclic or fused heterocyclic,
heteroaryl or fused heteroaryl, or
bicyclic heterocyclic or spiro heterocyclic,
wherein fused aryl, fused heterocyclic, fused heteroaryl, bicyclic heterocyclic, or spiro heterocyclic can be substituted.

The invention also provides a compound of Formula IV:

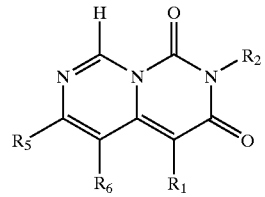

IV or a pharmaceutically acceptable salt thereof, wherein:
$R_1$ is H,
$C_1$–$C_7$ alkyl and substituted alkyl,
$C_2$–$C_7$ alkenyl and substituted alkenyl,
$C_2$–$C_7$ alkynyl and substituted alkynyl,
$C_3$–$C_7$ cycloalkyl and substituted cycloalkyl,
aryl and substituted aryl,
heterocyclic and substituted heterocyclic,
or heteroaryl and substituted heteroaryl;
$R_2$ is H,
$C_1$–$C_7$ alkyl and substituted alkyl,
$C_2$–$C_7$ alkenyl and substituted alkenyl,
$C_2$–$C_7$ alkynyl and substituted alkynyl,
$C_3$–$C_7$ cycloalkyl and substituted cycloalkyl,
aryl and substituted aryl,
heterocyclic and substituted heterocyclic,
heteroaryl and substituted heteroaryl,
halo,
$NO_2$,
NO, CN,
OR$_a$,

wherein R$_a$ is H,
C$_1$–C$_7$ alkyl and substituted alkyl,
C$_2$–C$_7$ alkenyl and substituted alkenyl,
C$_3$–C$_7$ cycloalkyl and substituted cycloalkyl,
aryl and substituted aryl,
heteroaryl and substituted heteroaryl,
heterocycloalkyl and substituted heterocycloalkyl,

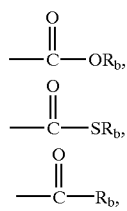

wherein R$_b$ is H,
C$_1$–C$_7$ alkyl and substituted alkyl,
C$_2$–C$_7$ alkenyl and substituted alkenyl,
C$_3$–C$_7$ cycloalkyl and substituted cycloalkyl,
aryl and substituted aryl,
heteroaryl and substituted heteroaryl,
heterocycloalkyl and substituted heterocycloalkyl;

wherein R$_c$ and R$_d$ are independantly H,
C$_1$–C$_7$ alkyl and substituted alkyl,
C$_3$–C$_7$ cycloalkyl and substituted cycloalkyl,
C$_2$–C$_7$ alkenyl and substituted alkenyl,
aryl and substituted aryl,
heteroaryl and substituted heteroaryl,
heterocycloalkyl and substituted heterocycloalkyl;
NR$_e$R$_f$, wherein
R$_e$ and R$_f$ are each independently H,
C$_1$–C$_7$ alkyl and substituted alkyl,
C$_2$–C$_7$ alkenyl and substituted alkenyl,
C$_2$–C$_7$ alkynyl and substituted alkynyl,
C$_3$–C$_7$ cycloalkyl and substituted cycloalkyl,
C$_5$–C$_8$ cycloalkenyl and substituted cycloalkenyl,
aryl and substituted aryl, or

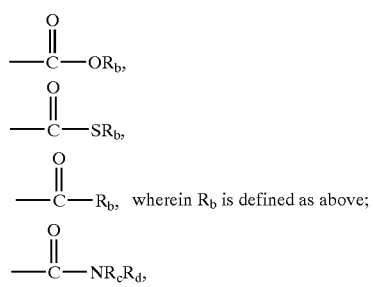

wherein R$_c$ and R$_d$ are defined as above;
aryl and substituted aryl,
heteroaryl and substituted heteroaryl,
heterocycloalkyl and substituted heterocycloalkyl, or
R$_e$ and R$_f$ are taken together with the nitrogen to which they are attached form a 4, 5, 6, 7, or 8 membered ring having from 0 to 3 heteroatoms selected from N, O, and S, wherein said ring is optionally substituted by one or more substituents;
R$_5$ is hydrogen,
C$_1$–C$_7$ alkyl and substituted alkyl,
C$_2$–C$_7$ alkenyl and substituted alkenyl,
C$_2$–C$_7$ alkynyl and substituted alkynyl,
OR$_a$, wherein R$_a$ is defined as above,

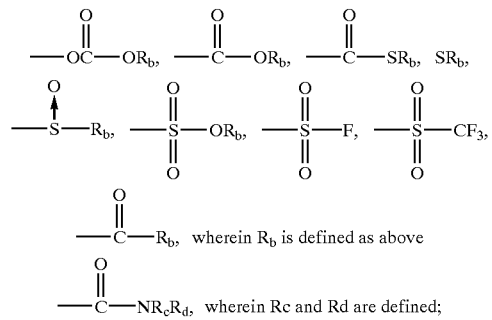

wherein R$_c$ and R$_d$ are defined as above;
halo,
NO$_2$,
CN,
NR$_e$R$_f$, wherein R$_e$ and R$_f$ are defined as above,
aryl or fused aryl,
heterocyclic or fused heterocyclic,
heteroaryl or fused heteroaryl,
bicyclic heterocyclic or spiro heterocyclic,
  wherein fused aryl, fused heterocyclic, fused heteroaryl, bicyclic heterocyclic, or spiro heterocyclic can be substituted;
R$_6$ is H,
OH,
(O)$_n$C$_1$–C$_7$ alkyl and substituted alkyl,
(O)$_n$C$_2$–C$_7$ alkenyl and substituted alkenyl,
(O)$_n$C$_2$–C$_7$ alkynyl and substituted alkynyl,
wherein n is 0 or 1,
halo,
NO$_2$,
CN,
NR$_e$R$_f$, wherein R$_e$ and R$_f$ are defined as above; or
R$_1$ and R$_6$ taken together with the atoms to which they are attached form a 5, 6, 7, or 8 membered ring having from 0 to 3 heteroatoms selected from N, O, and S, optionally substituted by one or more substituents.

The invention also provides a compound of Formula V:

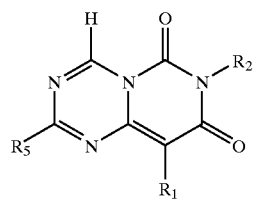

or a pharmaceutically acceptable salt thereof, wherein:
R$_1$ is H,
C$_1$–C$_7$ alkyl and substituted alkyl,
C$_2$–C$_7$ alkenyl and substituted alkenyl, C$_2$–C$_7$ alkynyl and substituted alkynyl,
C$_3$–C$_7$ cycloalkyl and substituted cycloalkyl,
aryl and substituted aryl,
heterocyclic and substituted heterocyclic,
or heteroaryl and substituted heteroaryl;

R$_2$ is H,
C$_1$–C$_7$ alkyl and substituted alkyl,
C$_2$–C$_7$ alkenyl and substituted alkenyl,
C$_2$–C$_7$ alkynyl and substituted alkynyl,
C$_3$–C$_7$ cycloalkyl and substituted cycloalkyl,
aryl and substituted aryl,
heterocyclic and substituted heterocyclic,
heteroaryl and substituted heteroaryl,
halo,
NO$_2$,
NO,
CN,
OR$_a$,

wherein R$_a$ is H,
C$_1$–C$_7$ alkyl and substituted alkyl,
C$_2$–C$_7$ alkenyl and substituted alkenyl,
C$_3$–C$_7$ cycloalkyl and substituted cycloalkyl,
aryl and substituted aryl,
heteroaryl and substituted heteroaryl,
heterocycloalkyl and substituted heterocycloalkyl,

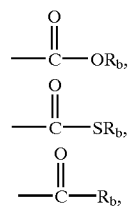

wherein R$_b$ is H,
C$_1$–C$_7$ alkyl and substituted alkyl,
C$_2$–C$_7$ alkenyl and substituted alkenyl,
C$_3$–C$_7$ cycloalkyl and substituted cycloalkyl,
aryl and substituted aryl,
heteroaryl and substituted heteroaryl,
heterocycloalkyl and substituted heterocycloalkyl;

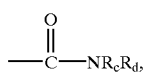

wherein R$_c$ and R$_d$ are independantly H,
C$_1$–C$_7$ alkyl and substituted alkyl,
C$_2$–C$_7$ alkenyl and substituted alkenyl,
C$_3$–C$_7$ cycloalkyl and substituted cycloalkyl,
aryl and substituted aryl,
heteroaryl and substituted heteroaryl,
heterocycloalkyl and substituted heterocycloalkyl;
NR$_e$R$_f$, wherein
R$_e$ and R$_f$ are each independently H,
C$_1$–C$_7$ alkyl and substituted alkyl,
C$_2$–C$_7$ alkenyl and substituted alkenyl,
C$_2$–C$_7$ alkynyl and substituted alkynyl,
C$_3$–C$_7$ cycloalkyl and substituted cycloalkyl,
C$_5$–C$_8$ cycloalkenyl and substituted cycloalkenyl,
aryl and substituted aryl, or

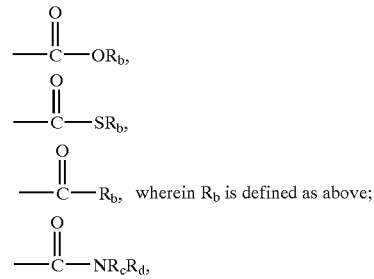

wherein R$_c$ and R$_d$ are defined as above;
aryl and substituted aryl,
heteroaryl and substituted heteroaryl,
heterocycloalkyl and substituted heterocycloalkyl, or
R$_e$ and R$_f$ are taken together with the nitrogen to which they are attached form a 4, 5, 6, 7, or 8 membered ring having from 0 to 3 heteroatoms selected from N, O, and S, wherein said ring is optionally substituted by one or more substituents;

R$_5$ is hydrogen,
C$_1$–C$_7$ alkyl and substituted alkyl,
C$_2$–C$_7$ alkenyl and substituted alkenyl,
C$_2$–C$_7$ alkynyl and substituted alkynyl,
OR$_a$, wherein R$_a$ is defined as above,

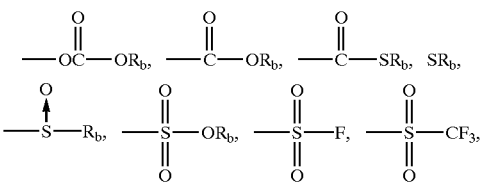

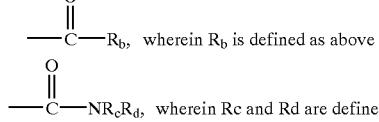

halo,
NO$_2$,
CN,
NR$_e$R$_f$, wherein R$_e$ and R$_f$ are defined as above,
aryl or fused aryl,
heterocyclic or fused heterocyclic,
heteroaryl or fused heteroaryl, or
bicyclic heterocyclic or spiro heterocyclic,
wherein fused aryl, fused heterocyclic, fused heteroaryl, bicyclic heterocyclic, or spiro heterocyclic can be substituted.

The invention further provides a compound of Formula VI

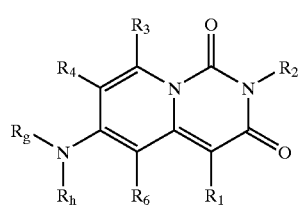

or a pharmaceutically acceptable salt thereof, wherein:

$R_1$ is H,
  $C_1$–$C_7$ alkyl and substituted alkyl,
  $C_2$–$C_7$ alkenyl and substituted alkenyl,
  $C_2$–$C_7$ alkynyl and substituted alkynyl,
  $C_3$–$C_7$ cycloalkyl and substituted cycloalkyl,
  aryl and substituted aryl,
  heterocyclic and substituted heterocyclic,
  or heteroaryl and substituted heteroaryl;

$R_2$ is H,
  $C_1$–$C_7$ alkyl and substituted alkyl,
  $C_2$–$C_7$ alkenyl and substituted alkenyl,
  $C_2$–$C_7$ alkynyl and substituted alkynyl,
  $C_3$–$C_7$ cycloalkyl and substituted cycloalkyl,
  aryl and substituted aryl,
  heterocyclic and substituted heterocyclic,
  heteroaryl and substituted heteroaryl,
  halo,
  $NO_2$,
  NO,
  CN,
  $OR_a$,

wherein $R_a$ is H,
  $C_1$–$C_7$ alkyl and substituted alkyl,
  $C_2$–$C_7$ alkenyl and substituted alkenyl,
  $C_3$–$C_7$ cycloalkyl and substituted cycloalkyl,
  aryl and substituted aryl,
  heteroaryl and substituted heteroaryl,
  heterocycloalkyl and substituted heterocycloalkyl,

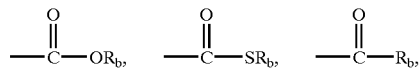

wherein $R_b$ is H,
  $C_1$–$C_7$ alkyl and substituted alkyl,
  $C_2$–$C_7$ alkenyl and substituted alkenyl,
  $C_3$–$C_7$ cycloalkyl and substituted cycloalkyl,
  aryl and substituted aryl,
  heteroaryl and substituted heteroaryl,
  heterocycloalkyl and substituted heterocycloalkyl;

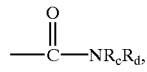

wherein $R_c$ and $R_d$ are independantly H,
  $C_1$–$C_7$ alkyl and substituted alkyl,
  $C_2$–$C_7$ alkenyl and substituted alkenyl,
  $C_3$–$C_7$ cycloalkyl and substituted cycloalkyl,
  aryl and substituted aryl,
  heteroaryl and substituted heteroaryl,
  heterocycloalkyl and substituted heterocycloalkyl;
$NR_eR_f$, wherein
  $R_e$ and $R_f$ are each independently H,
  $C_1$–$C_7$ alkyl and substituted alkyl,
  $C_2$–$C_7$ alkenyl and substituted alkenyl,
  $C_2$–$C_7$ alkynyl and substituted alkynyl,
  $C_3$–$C_7$ cycloalkyl and substituted cycloalkyl,
  $C_5$–$C_8$ cycloalkenyl and substituted cycloalkenyl,
  aryl and substituted aryl, or

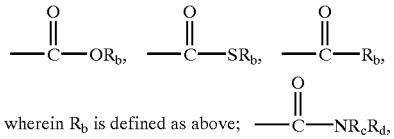

wherein $R_c$ and $R_d$ are defined as above;
  aryl and substituted aryl,
  heteroaryl and substituted heteroaryl,
  heterocycloalkyl and substituted heterocycloalkyl, or
  $R_e$ and $R_f$ are taken together with the nitrogen to which they are attached form a 4, 5, 6, 7, or 8 membered ring having from 0 to 3 heteroatoms selected from N, O, and S, wherein said ring is optionally substituted by one or more substituents;

$R_3$, $R_4$, and $R_6$ independently are H,
  OH,
  $(O)_nC_1$–$C_7$ alkyl and substituted alkyl,
  $(O)_nC_2$–$C_7$ alkenyl and substituted alkenyl,
  $(O)_nC_2$–$C_7$ alkynyl and substituted alkynyl,
wherein n is 0 or 1,
  halo,
  $NO_2$,
  CN, or
  $NR_eR_f$, wherein $R_e$ and $R_f$ are defined as above; and
$R_g$ and $R_h$ are defined as for $R_e$ and $R_f$ above.

The invention also provides a compound of Formula VII

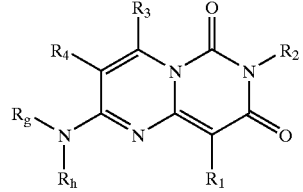

VII or a pharmaceutically acceptable salt thereof, wherein:

$R_1$ is H,
  $C_1$–$C_7$ alkyl and substituted alkyl,
  $C_2$–$C_7$ alkenyl and substituted alkenyl,
  $C_2$–$C_7$ alkynyl and substituted alkynyl,
  $C_3$–$C_7$ cycloalkyl and substituted cycloalkyl,
  aryl and substituted aryl,
  heterocyclic and substituted heterocyclic,
  or heteroaryl and substituted heteroaryl;

$R_2$ is H,
  $C_1$–$C_7$ alkyl and substituted alkyl,
  $C_2$–$C_7$ alkenyl and substituted alkenyl,
  $C_2$–$C_7$ alkynyl and substituted alkynyl,
  $C_3$–$C_7$ cycloalkyl and substituted cycloalkyl,
  aryl and substituted aryl,
  heterocyclic and substituted heterocyclic,
  heteroaryl and substituted heteroaryl,
  halo,
  $NO_2$,
  NO, CN,
OR$_a$,

wherein R$_a$ is H,
C$_1$–C$_7$ alkyl and substituted alkyl,
C$_2$–C$_7$ alkenyl and substituted alkenyl,
C$_3$–C$_7$ cycloalkyl and substituted cycloalkyl,
aryl and substituted aryl,
heteroaryl and substituted heteroaryl,
heterocycloalkyl and substituted heterocycloalkyl,

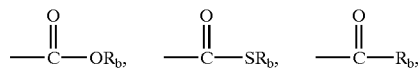

wherein R$_b$ is H,
C$_1$–C$_7$ alkyl and substituted alkyl,
C$_2$–C$_7$ alkenyl and substituted alkenyl,
C$_3$–C$_7$ cycloalkyl and substituted cycloalkyl,
aryl and substituted aryl,
heteroaryl and substituted heteroaryl,
heterocycloalkyl and substituted heterocycloalkyl;

wherein R$_c$ and R$_d$ are independantly H,
C$_1$–C$_7$ alkyl and substituted alkyl,
C$_2$–C$_7$ alkenyl and substituted alkenyl,
C$_3$–C$_7$ cycloalkyl and substituted cycloalkyl,
aryl and substituted aryl,
heteroaryl and substituted heteroaryl,
heterocycloalkyl and substituted heterocycloalkyl;
NR$_e$R$_f$, wherein
R$_e$ and R$_f$ are each independently H,
C$_1$–C$_7$ alkyl and substituted alkyl,
C$_2$–C$_7$ alkenyl and substituted alkenyl,
C$_2$–C$_7$ alkynyl and substituted alkynyl,
C$_3$–C$_7$ cycloalkyl and substituted cycloalkyl,
C$_5$–C$_8$ cycloalkenyl and substituted cycloalkenyl,
aryl and substituted aryl, or

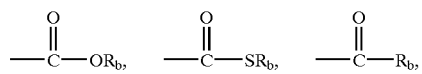

wherein R$_b$ is defined as above; 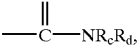

wherein R$_c$ and R$_d$ are defined as above;
aryl and substituted aryl,
heteroaryl and substituted heteroaryl,
heterocycloalkyl and substituted heterocycloalkyl, or
R$_e$ and R$_f$ are taken together with the nitrogen to which they are attached form a 4, 5, 6, 7, or 8 membered ring having from 0 to 3 heteroatoms selected from N, O, and S, wherein said ring is optionally substituted by one or more substituents;
R$_3$ and R$_4$ independently are H,
OH,
(O)$_n$C$_1$–C$_7$ alkyl and substituted alkyl,
(O)$_n$C$_2$–C$_7$ alkenyl and substituted alkenyl,
(O)$_n$C$_2$–C$_7$ alkynyl and substituted alkynyl,
wherein n is 0 or 1,
halo,
NO$_2$,
CN, or
NR$_e$R$_f$, wherein R$_e$ and R$_f$ are defined as above; and R$_g$ and R$_h$ are defined as for R$_e$ and R$_f$ above.

The invention further provides a compound of Formula VIII:

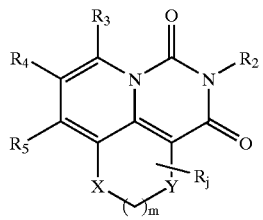

VIII or a pharmaceutically acceptable salt thereof, wherein:
R$_2$ is H,
C$_1$–C$_7$ alkyl and substituted alkyl,
C$_2$–C$_7$ alkenyl and substituted alkenyl,
C$_2$–C$_7$ alkynyl and substituted alkynyl,
C$_3$–C$_7$ cycloalkyl and substituted cycloalkyl,
aryl and substituted aryl,
heterocyclic and substituted heterocyclic,
heteroaryl and substituted heteroaryl,
halo,
NO$_2$,
NO,
CN,
OR$_a$,

wherein R$_a$ is H,
C$_1$–C$_7$ alkyl and substituted alkyl,
C$_2$–C$_7$ alkenyl and substituted alkenyl,
C$_3$–C$_7$ cycloalkyl and substituted cycloalkyl,
aryl and substituted aryl,
heteroaryl and substituted heteroaryl,
heterocycloalkyl and substituted heterocycloalkyl,

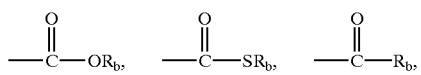

wherein R$_b$ is H,
C$_1$–C$_7$ alkyl and substituted alkyl,
C$_2$–C$_7$ alkenyl and substituted alkenyl,
C$_3$–C$_7$ cycloalkyl and substituted cycloalkyl,
aryl and substituted aryl,
heteroaryl and substituted heteroaryl,
heterocycloalkyl and substituted heterocycloalkyl;

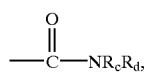

wherein R$_c$ and R$_d$ are independantly H,
C$_1$–C$_7$ alkyl and substituted alkyl,
C$_2$–C$_7$ alkenyl and substituted alkenyl,
C$_3$–C$_7$ cycloalkyl and substituted cycloalkyl, aryl and substituted aryl,
heteroaryl and substituted heteroaryl,
heterocycloalkyl and substituted heterocycloalkyl;
$NR_eR_f$, wherein
$R_e$ and $R_f$ are each independently H,
$C_1$–$C_7$ alkyl and substituted alkyl,
$C_2$–$C_7$ alkenyl and substituted alkenyl,
$C_2$–$C_7$ alkynyl and substituted alkynyl,
$C_3$–$C_7$ cycloalkyl and substituted cycloalkyl,
$C_5$–$C_8$ cycloalkenyl and substituted cycloalkenyl,
aryl and substituted aryl, or

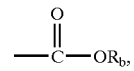

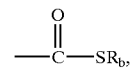

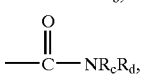

wherein $R_c$ and $R_d$ are defined as above;
aryl and substituted aryl,
heteroaryl and substituted heteroaryl,
heterocycloalkyl and substituted heterocycloalkyl, or
$R_e$ and $R_f$ are taken together with the nitrogen to which they are attached form a 4, 5, 6, 7, or 8 membered ring having from 0 to 3 heteroatoms selected from N, O, and S, wherein said ring is optionally substituted by one or more substituents;
$R_3$ and $R_4$ independently are H,
OH,
$(O)_nC_1$–$C_7$ alkyl and substituted alkyl,
$(O)_nC_2$–$C_7$ alkenyl and substituted alkenyl,
$(O)_nC_2$–$C_7$ alkynyl and substituted alkynyl,
wherein n is 0 or 1,
halo,
$NO_2$,
CN,
$NR_eR_f$, wherein $R_e$ and $R_f$ are defined as above,
$R_5$ is hydrogen,
$C_1$–$C_7$ alkyl and substituted alkyl,
$C_2$–$C_7$ alkenyl and substituted alkenyl,
$C_2$–$C_7$ alkynyl and substituted alkynyl,
$OR_a$, wherein $R_a$ is defined as above,

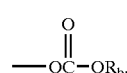

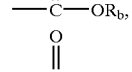

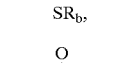

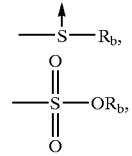

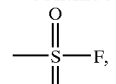

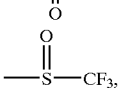

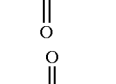

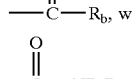

wherein $R_c$ and $R_d$ are defined as above;
halo,
$NO_2$,
CN,
$NR_eR_f$ as defined above,
aryl or fused aryl,
heterocyclic or fused heterocyclic,
heteroaryl or fused heteroaryl,
bicyclic heterocyclic or spiro heterocyclic,
wherein fused aryl, fused heterocyclic, fused heteroaryl, bicyclic heterocyclic, or spiro heterocyclic can be substituted; and
X and Y each independently are O, $CH_2$, $CH(C_1$–$C_7$ alkyl), NH, $N(C_1$–$C_7$ alkyl), S, SO, or $SO_2$;
m is 0-14;
$R_j$ is H,
OH,
$(O)_nC_1$–$C_7$ alkyl and substituted alkyl,
$(O)_nC_2$–$C_7$ alkenyl and substituted alkenyl,
$(O)_nC_2$–$C_7$ alkynyl and substituted alkynyl,
wherein n is 0 or 1,
halo,
$NO_2$,
CN,
$NR_kR_m$,
wherein $R_k$ and $R_m$ independently are H,
$C_1$–$C_7$ alkyl and substituted alkyl,
$C_2$–$C_7$ alkenyl and substituted alkenyl,
$C_2$–$C_7$ alkynyl and substituted alkynyl,

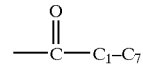

alkyl and substituted alkyl, or
$R_k$ and $R_m$ taken together with the nitrogen to which they are attached form a 3- to 7-membered ring containing from 1 to 3 heteroatoms selected from N, O, and S, said ring being unsubstituted or substituted with 1, 2, 3, or 4 substituent groups.

The invention also provides a compound which is:

2-Amino-4-cyclopropyl-7-fluoro-5-methyl-6-[3-(1-methylaminoethyl)pyrrolidin-1-yl]pyrido[1,2-c]pyrimidine-1,3-dione;

2-Amino-4-cyclopropyl-7-fluoro-5-methyl-6-pyrrolidin-1-yl-pyrido[1,2-c]pyrimidine-1,3-dione;

2-Amino-4-cyclopropyl-7-fluoro-6-[3-(1-hydroxyethyl)pyrrolidin-1-yl-5-methylpyrido[1,2-c]pyrimidine-1,3-dione;

2-Amino-6-[(R)-3-(1-aminocyclopropyl)pyrrolidin-1-yl]-4-cyclopropyl-7-fluoro-5-methylpyrido[1,2-c]pyrimidine-1,3-dione;

2-Amino-6-((3S, 4S) and (3R,4R)-3-aminomethyl-4-fluoropyrrolidin-1-yl)-4-cyclopropyl-7-fluoro-5-methylpyrido[1,2-c]pyrimidine-1,3-dione;

2-Amino-6-[(R)-3-((S)-1-aminoethyl)pyrrolidin-1-yl]-4-cyclopropyl-7-fluoro-5-methyl-pyrido[1,2-c]pyrimidine-1,3-dione; hydrochloride; and 2-Amino-6-[4-(1-aminoethyl)-3,3-dimethylpyrrolidin-1-yl]-4-cyclopropyl-7-fluoro-5-methyl-pyrido[1,2-c]pyrimidine-1,3-dione; hydrochloride;

2-Amino-4-cyclopropyl-7-fluoro-5-methyl-6-[3-(1-methylaminoethyl)pyrrolidin-1-yl]-pyrido[1,2-c]pyrimidine-1,3-dione;

2-Amino-4-cyclopropyl-7-fluoro-5-methyl-6-pyrrolidin-1-ylpyrido[1,2-c]pyrimidine-1,3-dione;

2-Amino-4-cyclopropyl-7-fluoro-6-[3-(1-hydroxyethyl)pyrrolidin-1-yl-5-methyl-pyrido[1,2-c]pyrimidine-1,3-dione;

2-Amino-6-[(R)-3-((R)-1-aminoethyl)-pyrrolidin-1-yl]-4-cyclopropyl-7-fluoro-5-methylpyrido[1,2-c]pyrimidine-1,3-dione hydrochloride;

2-Amino-6-[(R)-3-((S)-1-aminoethyl)-pyrrolidin-1-yl]-4-cyclopropyl-7-fluoro-5-methylpyrido[1,2-c]pyrimidine-1,3-dione hydrochloride;

2-Amino-6-[4-(1-aminoethyl)-3,3-dimethyl-pyrrolidin-1-yl]-4-cyclopropyl-7-fluoro-5-methylpyrido[1,2-c]pyrimidine-1,3-dione hydrochloride;

2-Amino-6-(3-aminopyrrolidin-1-yl)-4-cyclopropyl-7-fluoro-5-methylpyrido[1,2-c]pyrimidine-1,3-dione hydrochloride;

2-Amino-6-[3-(1-aminoethyl)-4-methylpyrrolidin-1-yl]-4-cyclopropyl-7-fluoro-5-methylpyrido[1,2-c]pyrimidine-1,3-dione hydrochloride;

2-Amino-6-[3-(1-amino-1-phenylmethyl)pyrrolidin-1-yl]-4-cyclopropyl-7-fluoro-5-methylpyrido[1,2-c]pyrimidine-1,3-dione;

2-Amino-6-{3-[1-amino-1-(2-fluorophenyl)methyl]pyrrolidin-1-yl}-4-cyclopropyl-7-fluoro-5-methylpyrido[1,2-c]pyrimidine-1,3-dione;

2-Amino-6-{3-[1-amino-1-(4-fluorophenyl)methyl]pyrrolidin-1-yl}-4-cyclopropyl-7-fluoro-5-methylpyrido[1,2-c]pyrimidine-1,3-dione;

2-Amino-6-{3-[1-amino-1-(2,4-difluorophenyl)methyl]pyrrolidin-1-yl}-4-cyclopropyl-7-fluoro-5-methylpyrido[1,2-c]pyrimidine-1,3-dione;

2-Amino-6-{3-[1-amino-1-(2,6-difluorophenyl)methyl]pyrrolidin-1-yl}-4-cyclopropyl-7-fluoro-5-methylpyrido[1,2-c]pyrimidine-1,3-dione;

2-Amino-6-{3-[1-amino-1-(2,4,6-trifluorophenyl)methyl]pyrrolidin-1-yl}-4-cyclopropyl-7-fluoro-5-methylpyrido[1,2-c]pyrimidine-1,3-dione;

2-Amino-6-[3-(1-aminopropyl)pyrrolidin-1-yl]-4-cyclopropyl-7-fluoro-5-methylpyrido[1,2-c]pyrimidine-1,3-dione;

2-Amino-6-[3-(1-amino-2-methylpropyl)pyrrolidin-1-yl]-4-cyclopropyl-7-fluoro-5-methylpyrido[1,2-c]pyrimidine-1,3-dione;

2-Amino-6-[3-(1-amino-2-cyclopropylmethyl)pyrrolidin-1-yl]-4-cyclopropyl-7-fluoro-5methylpyrido[1,2-c]pyrimidine-1,3-dione;

2-Amino-6-[3-(1-aminocyclopropyl)pyrrolidin-1-yl]-4-cyclopropyl-7-fluoro-5-methylpyrido[1,2-c]pyrimidine-1,3-dione;

2-Amino-6-[3-(1-aminocyclopropyl)-4-fluoropyrrolidin-1-yl]-4-cyclopropyl-7-fluoro-5-methylpyrido[1,2-c]pyrimidine-1,3-dione;

2-Amino-6-[3-(1-amino-1-phenylmethyl)-4-fluoropyrrolidin-1-yl]-4-cyclopropyl-7-fluoro-5-methylpyrido[1,2-c]pyrimidine-1,3-dione;

2-Amino-6-[3-(1-amino-2-fluoroethyl)pyrrolidin-1-yl]-4-cyclopropyl-7-fluoro-5-methylpyrido[1,2-c]pyrimidine-1,3-dione;

2-Amino-6-[3-(1-amino-2,2-difluorocyclopropyl)pyrrolidin-1-yl]-4-cyclopropyl-7-fluoro-5-methylpyrido[1,2-c]pyrimidine-1,3-dione;

2-Amino-6-[3-(1-aminoethyl)pyrrolidin-1-yl]-4-cyclopropyl-7-fluoro-5-methylpyrido[1,2-c]pyrimidine-1,3-dione;

2-Amino-6-[3-(1-amino-2-fluorocyclopropyl)pyrrolidin-1-yl]-4-cyclopropyl-7-fluoro-5-methylpyrido[1,2-c]pyrimidine-1,3-dione;

2-Amino-6-[3-(1-amino-1-methylethyl)pyrrolidin-1-yl]-4-cyclopropyl-7-fluoro-5-methylpyrido[1,2-c]pyrimidine-1,3-dione;

2-Amino-6-[3-(1-aminoethyl)-4-fluoropyrrolidin-1-yl]-4-cyclopropyl-7-fluoro-5-methylpyrido[1,2-c]pyrimidine-1,3-dione;

2-Amino-6-[3-(1-amino-1-pyridin-2-ylmethyl)pyrrolidin-1-yl]-4-cyclopropyl-7-fluoro-5-methylpyrido[1,2-c]pyrimidine-1,3-dione;

2-Amino-6-[3-(1-amino-2-fluorocyclopropyl)-4-fluoropyrrolidin-1-yl]-4-cyclopropyl-7-fluoro-5-methylpyrido[1,2-c]pyrimidine-1,3-dione;

2-Amino-6-[3-(1-amino-1-pyridin-3-ylmethyl)pyrrolidin-1-yl]-4-cyclopropyl-7-fluoro-5-methylpyrido[1,2-c]pyrimidine-1,3-dione;

2-Amino-6-[3-(1-amino-1-pyridin-4-ylmethyl)pyrrolidin-1-yl]-4-cyclopropyl-7-fluoro-5-methylpyrido[1,2-c]pyrimidine-1,3-dione;

2-Amino-6-(4-aminohexahydrocyclopenta[c]pyrrol-2-yl)-4-cyclopropyl-7-fluoro-5-methylpyrido[1,2-c]pyrimidine-1,3-dione;

2-Amino-6-(4-amino-5-fluorohexahydrocyclopenta[c]pyrrol-2-yl)-4-cyclopropyl-7-fluoro-5-methylpyrido[1,2-c]pyrimidine-1,3-dione;

2-Amino-4-cyclopropyl-7-fluoro-5-methyl-6-(3-phenylpyrrolidin-1-yl)pyrido[1,2-c]pyrimidine-1,3-dione;

2-Amino-4-cyclopropyl-7-fluoro-5-methyl-6-(3-pyridin-2-ylpyrrolidin-1-yl)pyrido[1,2-c]pyrimidine-1,3-dione;

2-Amino-4-cyclopropyl-7-fluoro-5-methyl-6-(3-pyridin-3-ylpyrrolidin-1-yl)pyrido[1,2-c]pyrimidine-1,3-dione;

2-Amino-4-cyclopropyl-7-fluoro-5-methyl-6-(3-pyridin-4-ylpyrrolidin-1-yl)pyrido[1,2-c]pyrimidine-1,3-dione;

2-Amino-4-cyclopropyl-7-fluoro-5-methyl-6-(piperazin-1-yl)pyrido[1,2-c]pyrimidine-1,3-dione;

2-Amino-4-cyclopropyl-7-fluoro-5-methyl-6-(4-methylpiperazin-1-yl)pyrido[1,2-c]pyrimidine-1,3-dione;

N-{1-[1-(2-Amino-4-cyclopropyl-7-fluoro-5-methyl-1,3-dioxo-2,3-dihydro-1H-pyrido[1,2-c]pyrimidin-6-yl)pyrrolidin-3-yl]ethyl}methanesulfonamide, 2-Amino-4-cyclopropyl-7-fluoro-5-methyl-6-octahydropyrrolo[3,4-b]pyridin-6-yl)pyrido[1,2-c]pyrimidine-1,3-dione;

2-Amino-6-(7-amino-5-azaspiro[2.4]hept-5-yl)-4-cyclopropyl-7-fluoro-5-methylpyrido[1,2-c]pyrimidine-1,3-dione;

2-Amino-4-cyclopropyl-7-fluoro-5-methyl-6-(thiophen-3-yl)pyrido[1,2-c]pyrimidine-1,3-dione;

2-Amino-4-cyclopropyl-7-fluoro-5-methyl-6-(1-methyl-2,3-dihydro-1H-isoindol-5-yl)pyrido[1,2-c]pyrimidine-1,3-dione;

2-Amino-4-cyclopropyl-7-fluoro-6-(7-hydroxymethyl-5-azaspiro[2.4]hept-5-yl)-5-methylpyrido[1,2-c]pyrimidine-1,3-dione;

2-Amino-6-(3-amino-4-methoxyiminopyrrolidin-1-yl)-4-cyclopropyl-7-fluoro-5-methylpyrido[1,2-c]pyrimidine-1,3-dione;

2-Amino-4-cyclopropyl-7-fluoro-5-methyl-6-(3-methylaminomethylpyrrolidin-1-yl)pyrido[1,2-c]pyrimidine-1,3-dione;
2-Amino-6-(5-aminomethylthiophen-3-yl)-4-cyclopropyl-7-fluoro-5-methylpyrido[1,2-c]pyrimidine-1,3-dione;
2-Amino-6-[3-(1-aminoethyl)-3-fluoropyrrolidin-1-yl]-4-cyclopropyl-7-fluoro-5-methylpyrido[1,2-c]pyrimidine-1,3-dione;
2-Amino-6-(5-aminomethylthiophen-3-yl]-4-cyclopropyl-7-fluoro-5-methylpyrido[1,2-c]pyrimidine-1,3-dione;
2-Amino-6-(5-aminomethylthiophen-2-yl]-4-cyclopropyl-7-fluoro-5-methylpyrido[1,2-c]pyrimidine-1,3-dione;
2-Amino-6-(4-aminomethylthiophen-2-yl]-4-cyclopropyl-7-fluoro-5-methylpyrido[1,2-c]pyrimidine-1,3-dione;
2-Amino-6-(4-aminomethylthiophen-3-yl]-4-cyclopropyl-7-fluoro-5-methylpyrido[1,2-c]pyrimidine-1,3-dione;
2-Amino-4-cyclopropyl-6-(5,6-dihydro-4H-thieno[2,3-c]pyrrol-3-yl)-7-fluoro-5-methylpyrido[1,2-c]pyrimidine-1,3-dione;
2-Amino-4-cyclopropyl-6-(5,6-dihydro-4H-thieno[2,3-c]pyrrol-2-yl)-7-fluoro-5-methylpyrido[1,2-c]pyrimidine-1,3-dione;
2-Amino-4-cyclopropyl-7-fluoro-5-methyl-6-(6-methyl-5,6-dihydro-4H-thieno[2,3-c]pyrrol-2-yl)pyrido[1,2-c]pyrimidine-1,3-dione;
2-Amino-4-cyclopropyl-7-fluoro-5-methyl-6-(6-methyl-5,6-dihydro-4H-thieno[2,3-c]pyrrol-3-yl)pyrido[1,2-c]pyrimidine-1,3-dione;
2-Amino-4-cyclopropyl-7-fluoro-5-methyl-6-(5-pyridin-4-ylthiophen-3-yl)pyrido[1,2-c]pyrimidine-1,3-dione;
2-Amino-4-cyclopropyl-7-fluoro-5-methyl-6-(5-pyridin-3-ylthiophen-3-yl)pyrido[1,2-c]pyrimidine-1,3-dione;
2-Amino-4-cyclopropyl-7-fluoro-5-methyl-6-(5-pyridin-2-ylthiophen-3-yl)pyrido[1,2-c]pyrimidine-1,3-dione;
2-Amino-4-cyclopropyl-7-fluoro-5-methyl-6-(4-pyridin-4-ylthiophen-3-yl)pyrido[1,2-c]pyrimidine-1,3-dione;
2-Amino-4-cyclopropyl-7-fluoro-5-methyl-6-(4-pyridin-3-ylthiophen-3-yl)pyrido[1,2-c]pyrimidine-1,3-dione;
2-Amino-4-cyclopropyl-7-fluoro-5-methyl-6-(4-pyridin-2-ylthiophen-3-yl)pyrido[1,2-c]pyrimidine-1,3-dione;
2-Amino-4-cyclopropyl-7-fluoro-5-methyl-6-pyridin-4-ylpyrido[1,2-c]pyrimidine-1,3-dione;
2-Amino-6-(4-aminomethylpyridin-2-yl)-4-cyclopropyl-7-fluoro-5-methylpyrido[1,2-c]pyrimidine-1,3-dione;
2-Amino-6-(5-aminomethylpyridin-2-yl)-4-cyclopropyl-7-fluoro-5-methylpyrido[1,2-c]pyrimidine-1,3-dione;
2-Amino-6-(6-aminomethylpyridin-2-yl)-4-cyclopropyl-7-fluoro-5-methylpyrido[1,2-c]pyrimidine-1,3-dione;
2-Amino-6-(5-aminomethylpyrimidin-2-yl]-4-cyclopropyl-7-fluoro-5-methylpyrido[1,2-c]pyrimidine-1,3-dione;
2-Amino-4-cyclopropyl-7-fluoro-5-methyl-6-pyrimidin-2-ylpyrido[1,2-c]pyrimidine-1,3-dione;
2-Amino-6-(2-aminomethylpyrimidin-5-yl]-4-cyclopropyl-7-fluoro-5-methylpyrido[1,2-c]pyrimidine-1,3-dione;
2-Amino-4-cyclopropyl-7-fluoro-5-methyl-6-pyrimidin-5-ylpyrido[1,2-c]pyrimidine-1,3-dione;
2-Amino-4-cyclopropyl-7-fluoro-5-methyl-6-pyrazin-2-ylpyrido[1,2-c]pyrimidine-1,3-dione;
2-Amino-6-(6-aminomethylpyrazin-2-yl]-4-cyclopropyl-7-fluoro-5-methylpyrido[1,2-c]pyrimidine-1,3-dione;
2-Amino-6-[3-(6-aminomethylpyridin-2-yl)pyrrolidin-1-yl]-4-cyclopropyl-7-fluoro-5-methylpyrido[1,2-c]pyrimidine-1,3-dione;
2-Amino-6-[3-(2-aminomethylpyridin-3-yl)pyrrolidin-1-yl]-4-cyclopropyl-7-fluoro-5-methylpyrido[1,2-c]pyrimidine-1,3-dione;
2-Amino-6-[5-(2-aminomethylpyridin-3-yl)thiophen-3-yl]-4-cyclopropyl-7-fluoro-5-methylpyrido[1,2-c]pyrimidine-1,3-dione;
2-Amino-6-[5-(2-aminomethylpyridin-3-yl)thiophen-2-yl]-4-cyclopropyl-7-fluoro-5-methylpyrido[1,2-c]pyrimidine-1,3-dione;
2-Amino-6-[5-(6-aminomethylpyridin-2-yl)thiophen-2-yl]-4-cyclopropyl-7-fluoro-5-methylpyrido[1,2-c]pyrimidine-1,3-dione;
2-Amino-6-[5-(6-aminomethylpyridin-2-yl)thiophen-3-yl]-4-cyclopropyl-7-fluoro-5-methylpyrido[1,2-c]pyridine-1,3-dione;
2-Amino-6-[4-(2-aminomethylpyridin-3-yl)thiophen-2-yl]-4-cyclopropyl-7-fluoro-5-methylpyrido[1,2-c]pyrimidine-1,3-dione;
2-Amino-6-[3-(2-aminomethylpyridin-3-yl)thiophen-2-yl]-4-cyclopropyl-7-fluoro-5-methylpyrido[1,2-c]pyrimidine-1,3-dione;
2-Amino-6-[4-(6-aminomethylpyridin-2-yl)thiophen-3-yl]-4-cyclopropyl-7-fluoro-5-methylpyrido[1,2-c]pyrimidine-1,3-dione;
2-Amino-4-cyclopropyl-7-fluoro-5-methyl-6-(4-pyridin-4-ylthiophen-2-yl)pyrido[1,2-c]pyrimidine-1,3-dione;
2-Amino-6-[4-(1-aminoethyl)thiophen-2-yl]-4-cyclopropyl-7-fluoro-5-methylpyrido[1,2-c]pyrimidine-1,3-dione;
2-Amino-6-[(R)-3-(1-aminocyclopropyl)pyrrolidin-1-yl]-4-cyclopropyl-7-fluoro-5-methylpyrido[1,2-c]pyrimidine-1,3-dione;
2-Amino-6-((3S, 4S) and (3R,4R)-3-aminomethyl-4-fluoropyrrolidin-1-yl)-4-cyclopropyl-7-fluoro-5-methylpyrido[1,2-c]pyrimidine-1,3-dione;
2-Amino-6-(3-aminomethylpyrrolidin-1-yl)-4-cyclopropyl-7-fluoro-5-methylpyrido-[1,2-c]pyrimidine-1,3-dione;
2-Amino-6-(7-amino-5-azospiro[2.4]hept-5-yl)-4-cyclopropyl-7-fluoro-5-methylpyrido[1,2-c]primidine-1,3-dione;
2-Amino-6-[3-(aminooxazol-4-yl-methyl)pyrrolidin-1-yl]-4-cyclopropyl-7-fluoro-5-methylpyrido[1,2-c]pyrimidine-1,3-dione;
2-Amino-6-(4-aminooctahydroisoindol-2-yl)-4-cyclopropyl-7-fluoro-5-methylpyrido[1,2-c]pyrimidine-1,3-dione;
2-Amino-6-[3-(1-amino-1-methylethyl)pyrrolidine-1-yl]-4-cyclopropyl-7-fluoro-5-methylpyrido[1,2-c]pyrimidine-1,3-dione; and
6-Chloro-4-cyclopropyl-7-fluoro-5-methylpyrido[1,2-c]pyrimidine-1,3-dione;
2-Amino-4-cyclopropyl-7-fluoro-5-methoxy-6-[3-(1-methylaminoethyl)pyrrolidin-1-yl]pyrido[1,2-c]pyrimidine-1,3-dione;
2-Amino-4-cyclopropyl-7-fluoro-5-methoxy-6-pyrrolidin-1-yl-pyrido[1,2-c]pyrimidine-1,3-dione;
2-Amino-4-cyclopropyl-7-fluoro-6-[3-(1-hydroxyethyl)pyrrolidin-1-yl-5-methoxypyrido[1,2-c]pyrimidine-1,3-dione;
2-Amino-6-[(R)-3-(1-aminocyclopropyl)pyrrolidin-1-yl]-4-cyclopropyl-7-fluoro-5-methoxypyrido[1,2-c]pyrimidine-1,3-dione;
2-Amino-6-((3S, 4S) and (3R,4R)-3-aminomethyl-4-fluoropyrrolidin-1-yl)-4-cyclopropyl-7-fluoro-5-methoxypyrido[1,2-c]pyrimidine-1,3-dione;

2-Amino-6-[(R)-3-((S)-1-aminoethyl)pyrrolidin-1-yl]-4-cyclopropyl-7-fluoro-5-methoxypyrido[1,2-c]pyrimidine-1,3-dione; hydrochloride; and 2-Amino-6-[4-(1-aminoethyl)-3,3-dimethylpyrrolidin-1-yl]-4-cyclopropyl-7-fluoro-5-methoxypyrido[1,2-c]pyrimidine-1,3-dione; hydrochloride;

2-Amino-4-cyclopropyl-7-fluoro-5-methoxy-6-[3-(1-methylaminoethyl)pyrrolidin-1-yl]-pyrido[1,2-c]pyrimidine-1,3-dione;

2-Amino-4-cyclopropyl-7-fluoro-5-methoxy-6-pyrrolidin-1-ylpyrido[1,2-c]pyrimidine-1,3-dione;

2-Amino-4-cyclopropyl-7-fluoro-6-[3-(1-hydroxyethyl)pyrrolidin-1-yl-5-methoxypyrido[1,2-c]pyrimidine-1,3-dione;

2-Amino-6-[(R)-3-((R)-1-aminoethyl)-pyrrolidin-1-yl]-4-cyclopropyl-7-fluoro-5-methoxypyrido[1,2-c]pyrimidine-1,3-dione hydrochloride;

2-Amino-6-[(R)-3-((S)-1-aminoethyl)-pyrrolidin-1-yl]-4-cyclopropyl-7-fluoro-5-methoxypyrido[1,2-c]pyrimidine-1,3-dione hydrochloride;

2-Amino-6-[4-(1-aminoethyl)-3,3-dimethyl-pyrrolidin-1-yl]-4-cyclopropropyl-7-fluoro-5-methoxypyrido[1,2-c]pyrimidine-1,3-dione hydrochloride;

2-Amino-6-(3-aminopyrrolidin-1-yl)-4-cyclopropyl-7-fluoro-5-methoxypyrido[1,2-c]pyrimidine-1,3-dione hydrochloride;

2-Amino-6-[3-(1-aminoethyl)-4-methylpyrrolidin-1-yl]-4-cyclopropyl-7-fluoro-5-methoxypyrido[1,2-c]pyrimidine-1,3-dione hydrochloride;

2-Amino-6-[3-(1-amino-1-phenylmethyl)pyrrolidin-1-yl]-4-cyclopropyl-7-fluoro-5-methoxypyrido[1,2-c]pyrimidine-1,3-dione;

2-Amino-6-{3-[1-amino-1-(2-fluorophenyl)methyl]pyrrolidin-1-yl}-4-cyclopropyl-7-fluoro-5-methoxypyrido[1,2-c]pyrimidine-1,3-dione;

2-Amino-6-{3-[1-amino-1-(4-fluorophenyl)methylpyrrolidin-1-yl]-4-cyclopropyl-7-fluoro-5-methoxypyrido[1,2-c]pyrimidine-1,3-dione;

2-Amino-6-{3-[1-amino-1-(2,4-difluorophenyl)methyl]pyrrolidin-1-yl}-4-cyclopropyl-7-fluoro-5-methoxypyrido[1,2-c]pyrimidine-1,3-dione;

2-Amino-6-{3-[1-amino-1-(2,6-difluorophenyl)methyl]pyrrolidin-1-yl}-4-cyclopropyl-7-fluoro-5-methoxypyrido[1,2-c]pyrimidine-1,3-dione;

2-Amino-6-{3-[1-amino-1-(2,4,6-trifluorophenyl)methyl]pyrrolidin-1-yl}-4-cyclopropyl-7-fluoro-5-methoxypyrido[1,2-c]pyrimidine-1,3-dione;

2-Amino-6-[3-(1-aminopropyl)pyrrolidin-1-yl]-4-cyclopropyl-7-fluoro-5-methoxypyrido[1,2-c]pyrimidine-1,3-dione;

2-Amino-6-[3-(1-amino-2-methylpropyl)pyrrolidin-1-yl]-4-cyclopropyl-7-fluoro-5-methoxypyrido[1,2-c]pyrimidine-1,3-dione;

2-Amino-6-[3-(1-amino-2-cyclopropylmethyl)pyrrolidin-1-yl]-4-cyclopropyl-7-fluoro-5-methoxypyrido[1,2-c]pyrimidine-1,3-dione;

2-Amino-6-[3-(1-aminocyclopropyl)pyrrolidin-1-yl]-4-cyclopropyl-7-fluoro-5-methoxypyrido[1,2-c]pyrimidine-1,3-dione;

2-Amino-6-[3-(1-aminocyclopropyl)-4-fluoropyrrolidin-1-yl]-4-cyclopropyl-7-fluoro-5-methoxypyrido[1,2-c]pyrimidine-1,3-dione;

2-Amino-6-[3-(1-amino-1-phenylmethyl)-4-fluoropyrrolidin-1-yl]-4-cyclopropyl-7-fluoro-5-methoxypyrido[1,2-c]pyrimidine-1,3-dione;

2-Amino-6-[3-(1-amino-2-fluoroethyl)pyrrolidin-1-yl]-4-cyclopropyl-7-fluoro-5-methoxypyrido[1,2-c]pyrimidine-1,3-dione;

2-Amino-6-[3-(1-amino-2,2-difluorocyclopropyl)pyrrolidin-1-yl]-4-cyclopropyl-7-fluoro-5-methoxypyrido[1,2-c]pyrimidine-1,3-dione;

2-Amino-6-[3-(1-aminoethyl)pyrrolidin-1-yl]-4-cyclopropyl-7-fluoro-5-methoxypyrido[1,2-c]pyrimidine-1,3-dione;

2-Amino-6-[3-(1-amino-2-fluorocyclopropyl)pyrrolidin-1-yl]-4-cyclopropyl-7-fluoro-5-methoxypyrido[1,2-c]pyrimidine-1,3-dione;

2-Amino-6-[3-(1-amino-1-methylethyl)pyrrolidin-1-yl]-4-cyclopropyl-7-fluoro-5-methoxypyrido[1,2-c]pyrimidine-1,3-dione;

2-Amino-6-[3-(1-aminoethyl)-4-fluoropyrrolidin-1-yl]-4-cyclopropyl-7-fluoro-5-methoxypyrido[1,2-c]pyrimidine-1,3-dione;

2-Amino-6-[3-(1-amino-1-pyridin-2-ylmethyl)pyrrolidin-1-yl]-4-cyclopropyl-7-fluoro-5-methoxypyrido[1,2-c]pyrimidine-1,3-dione;

2-Amino-6-[3-(1-amino-2-fluorocyclopropyl)-4-fluoropyrrolidin-1-yl]-4-cyclopropyl-7-fluoro-5-methoxypyrido[1,2-c]pyrimidine-1,3-dione;

2-Amino-6-[3-(1-amino-1-pyridin-3-ylmethyl)pyrrolidin-1-yl]-4-cyclopropyl-7-fluoro-5-methoxypyrido[1,2-c]pyrimidine-1,3-dione;

2-Amino-6-[3-(1-amino-1-pyridin-4-ylmethyl)pyrrolidin-1-yl]-4-cyclopropyl-7-fluoro-5-methoxypyrido[1,2-c]pyrimidine-1,3-dione;

2-Amino-6-(4-aminohexahydrocyclopenta[c]pyrrol-2-yl)-4-cyclopropyl-7-fluoro-5-methoxypyrido[1,2-c]pyrimidine-1,3-dione;

2-Amino-6-(4-amino-5-fluorohexahydrocyclopenta[c]pyrrol-2-yl)-4-cyclopropyl-7-fluoro-5-methoxypyrido[1,2-c]pyrimidine-1,3-dione;

2-Amino-4-cyclopropyl-7-fluoro-5-methoxy-6-(3-phenylpyrrolidin-1-yl)pyrido[1,2-c]pyrimidine-1,3-dione;

2-Amino-4-cyclopropyl-7-fluoro-5-methoxy-6-(3-pyridin-2-ylpyrrolidin-1-yl)pyrido[1,2-c]pyrimidine-1,3-dione;

2-Amino-4-cyclopropyl-7-fluoro-5-methoxy-6-(3-pyridin-3-ylpyrrolidin-1-yl)pyrido[1,2-c]pyrimidine-1,3-dione;

2-Amino-4-cyclopropyl-7-fluoro-5-methoxy-6-(3-pyridin-4-ylpyrrolidin-1-yl)pyrido[1,2-c]pyrimidine-1,3-dione;

2-Amino-4-cyclopropyl-7-fluoro-5-methoxy-6-(piperazin-1-yl)pyrido[1,2-c]pyrimidine-1,3-dione;

2-Amino-4-cyclopropyl-7-fluoro-5-methoxy-6-(4-methylpiperazin-1-yl)pyrido[1,2-c]pyrimidine-1,3-dione;

N-{1-[1-(2-Amino-4-cyclopropyl-7-fluoro-5-methoxy-1,3-dioxo-2,3-dihydro-1H-pyrido[1,2-c]pyrimidin-6-yl)pyrrolidin-3-yl]ethyl}methanesulfonamide, 2-Amino-4-cyclopropyl-7-fluoro-5-methoxy-6-octahydropyrrolo[3,4-b]pyridin-6-yl)pyrido[1,2-c]pyrimidine-1,3-dione;

2-Amino-6-(7-amino-5-azaspiro[2.4]hept-5-yl)-4-cyclopropyl-7-fluoro-5-methoxypyrido[1,2-c]pyrimidine-1,3-dione;

2-Amino-4-cyclopropyl-7-fluoro-5-methoxy-6-(thiophen-3-yl)pyrido[1,2-c]pyrimidine-1,3-dione;

2-Amino-4-cyclopropyl-7-fluoro-5-methoxy-6-(1-methyl-2,3-dihydro-1H-isoindol-5-yl)pyrido[1,2-c]pyrimidine-1,3-dione;

2-Amino-4-cyclopropyl-7-fluoro-6-(7-hydroxymethyl-5-azaspiro[2.4]hept-5-yl)-5-methoxypyrido[1,2-c]pyrimidine-1,3-dione;

2-Amino-6-(3-amino-4-methoxyiminopyrrolidin-1-yl)-4-cyclopropyl-7-fluoro-5-methoxypyrido[1,2-c]pyrimidine-1,3-dione;

2-Amino-4-cyclopropyl-7-fluoro-5-methoxy-6-(3-methylaminomethylpyrrolidin-1-yl)pyrido[1,2-c]pyrimidine-1,3-dione;

2-Amino-6-(5-aminomethylthiophen-3-yl)-4-cyclopropyl-7-fluoro-5-methoxypyrido[1,2-c]pyrimidine-1,3-dione;

2-Amino-6-[3-(1-aminoethyl)-3-fluoropyrrolidin-1-yl]-4-cyclopropyl-7-fluoro-5-methoxypyrido[1,2-c]pyrimidine-1,3-dione;

2-Amino-6-(5-aminomethylthiophen-3-yl]-4-cyclopropyl-7-fluoro-5-methoxypyrido[1,2-c]pyrimidine-1,3-dione;

2-Amino-6-(5-aminomethylthiophen-2-yl]-4-cyclopropyl-7-fluoro-5-methoxypyrido[1,2-c]pyrimidine-1,3-dione;

2-Amino-6-(4-aminomethylthiophen-2-yl]-4-cyclopropyl-7-fluoro-5-methoxypyrido[1,2-c]pyrimidine-1,3-dione;

2-Amino-6-(4-aminomethylthiophen-3-yl]-4-cyclopropyl-7-fluoro-5-methoxypyrido[1,2-c]pyrimidine-1,3-dione;

2-Amino-4-cyclopropyl-6-(5,6-dihydro-4H-thieno[2,3-c]pyrrol-3-yl)-7-fluoro-5-methoxypyrido[1,2-c]pyrimidine-1,3-dione;

2-Amino-4-cyclopropyl-6-(5,6-dihydro-4H-thieno[2,3-c]pyrrol-2-yl)-7-fluoro-5-methoxypyrido[1,2-c]pyrimidine-1,3-dione;

2-Amino-4-cyclopropyl-7-fluoro-5-methoxy-6-(6-methyl-5,6-dihydro-4H-thieno[2,3-c]pyrrol-2-yl)pyrido[1,2-c]pyrimidine-1,3-dione;

2-Amino-4-cyclopropyl-7-fluoro-5-methoxy-6-(6-methyl-5,6-dihydro-4H-thieno[2,3-c]pyrrol-3-yl)pyrido[1,2-c]pyrimidine-1,3-dione;

2-Amino-4-cyclopropyl-7-fluoro-5-methoxy-6-(5-pyridin-4-ylthiophen-3-yl)pyrido[1,2-c]pyrimidine-1,3-dione;

2-Amino-4-cyclopropyl-7-fluoro-5-methoxy-6-(5-pyridin-3-ylthiophen-3-yl)pyrido[1,2-c]pyrimidine-1,3-dione;

2-Amino-4-cyclopropyl-7-fluoro-5-methoxy-6-(5-pyridin-2-ylthiophen-3-yl)pyrido[1,2-c]pyrimidine-1,3-dione;

2-Amino-4-cyclopropyl-7-fluoro-5-methoxy-6-(4-pyridin-4-ylthiophen-3-yl)pyrido[1,2-c]pyrimidine-1,3-dione;

2-Amino-4-cyclopropyl-7-fluoro-5-methoxy-6-(4-pyridin-3-ylthiophen-3-yl)pyrido[1,2-c]pyrimidine-1,3-dione;

2-Amino-4-cyclopropyl-7-fluoro-5-methoxy-6-(4-pyridin-2-ylthiophen-3-yl)pyrido[1,2-c]pyrimidine-1,3-dione;

2-Amino-4-cyclopropyl-7-fluoro-5-methoxy-6-pyridin-4-ylpyrido[1,2-c]pyrimidine-1,3-dione;

2-Amino-6-(4-aminomethylpyridin-2-yl)-4-cyclopropyl-7-fluoro-5-methoxypyrido[1,2-c]pyrimidine-1,3-dione;

2-Amino-6-(5-aminomethylpyridin-2-yl)-4-cyclopropyl-7-fluoro-5-methoxypyrido[1,2-c]pyrimidine-1,3-dione;

2-Amino-6-(6-aminomethylpyridin-2-yl)-4-cyclopropyl-7-fluoro-5-methoxypyrido[1,2-c]pyrimidine-1,3-dione;

2-Amino-6-(5-aminomethylpyrimidin-2-yl]-4-cyclopropyl-7-fluoro-5-methoxypyrido[1,2-c]pyrimidine-1,3-dione;

2-Amino-4-cyclopropyl-7-fluoro-5-methoxy-6-pyrimidin-2-ylpyrido[1,2-c]pyrimidine-1,3-dione;

2-Amino-6-(2-aminomethylpyrimidin-5-yl]-4-cyclopropyl-7-fluoro-5-methoxypyrido[1,2-c]pyrimidine-1,3-dione;

2-Amino-4-cyclopropyl-7-fluoro-5-methoxy-6-pyrimidin-5-ylpyrido[1,2-c]pyrimidine-1,3-dione;

2-Amino-4-cyclopropyl-7-fluoro-5-methoxy-6-pyrazin-2-ylpyrido[1,2-c]pyrimidine-1,3-dione;

2-Amino-6-(6-aminomethylpyrazin-2-yl]-4-cyclopropyl-7-fluoro-5-methoxypyrido[1,2-c]pyrimidine-1,3-dione;

2-Amino-6-[3-(6-aminomethylpyridin-2-yl)pyrrolidin-1-yl]-4-cyclopropyl-7-fluoro-5-methoxypyrido[1,2-c]pyrimidine-1,3-dione;

2-Amino-6-[3-(2-aminomethylpyridin-3-yl)pyrrolidin-1-yl]-4-cyclopropyl-7-fluoro-5-methoxypyrido[1,2-c]pyrimidine-1,3-dione;

2-Amino-6-[5-(2-aminomethylpyridin-3-yl)thiophen-3-yl]-4-cyclopropyl-7-fluoro-5-methoxypyrido[1,2-c]pyrimidine-1,3-dione;

2-Amino-6-[5-(2-aminomethylpyridin-3-yl)thiophen-2-yl]-4-cyclopropyl-7-fluoro-5-methoxypyrido[1,2-c]pyrimidine-1,3-dione;

2-Amino-6-[5-(6-aminomethylpyridin-2-yl)thiophen-2-yl]-4-cyclopropyl-7-fluoro-5-methoxypyrido[1,2-c]pyrimidine-1,3-dione;

2-Amino-6-[5-(6-aminomethylpyridin-2-yl)thiophen-3-yl]-4-cyclopropyl-7-fluoro-5-methoxypyrido[1,2-c]pyrimidine-1,3-dione;

2-Amino-6-[4-(2-aminomethylpyridin-3-yl)thiophen-2-yl]-4-cyclopropyl-7-fluoro-5-methoxypyrido[1,2-c]pyrimidine-1,3-dione;

2-Amino-6-[3-(2-aminomethylpyridin-3-yl)thiophen-2-yl]-4-cyclopropyl-7-fluoro-5-methoxypyrido[1,2-c]pyrimidine-1,3-dione;

2-Amino-6-[4-(6-aminomethylpyridin-2-yl)thiophen-3-yl]-4-cyclopropyl-7-fluoro-5-methoxypyrido[1,2-c]pyrimidine-1,3-dione;

2-Amino-4-cyclopropyl-7-fluoro-5-methoxy-6-(4-pyridin-4-ylthiophen-2-yl)pyrido[1,2-c]pyrimidine-1,3-dione;

2-Amino-6-[4-(1-aminoethyl)thiophen-2-yl]-4-cyclopropyl-7-fluoro-5-methoxypyrido[1,2-c]pyrimidine-1,3-dione;

2-Amino-6-[(R)-3-(1-aminocyclopropyl)pyrrolidin-1-yl]-4-cyclopropyl-7-fluoro-5-methoxypyrido[1,2-c]pyrimidine-1,3-dione;

2-Amino-6-((3S, 4S) and (3R,4R)-3-aminomethyl-4-fluoropyrrolidin-1-yl)-4-cyclopropyl-7-fluoro-5-methoxypyrido[1,2-c]pyrimidine-1,3-dione;

2-Amino-6-(3-aminomethylpyrrolidin-1-yl)-4-cyclopropyl-7-fluoro-5-methoxypyrido-[1,2-c]pyrimidine-1,3-dione;

2-Amino-6-(7-amino-5-azospiro[2.4]hept-5-yl)-4-cyclopropyl-7-fluoro-5-methoxypyrido[1,2-c]primidine-1,3-dione;

2-Amino-6-[3-(aminooxazol-4-yl-methyl)pyrrolidin-1-yl]-4-cyclopropyl-7-fluoro-5-methoxypyrido[1,2-c]pyrimidine-1,3-dione;

2-Amino-6-(4-aminooctahydroisoindol-2-yl)-4-cyclopropyl-7-fluoro-5-methoxypyrido[1,2-c]pyrimidine-1,3-dione;

2-Amino-6-[3-(1-aminoethyl)pyrrolidin-1-yl]-4-cyclopropyl-7-fluoro-5,8-dimethylpyrido[1,2-c]pyrimidine-1,3-dione;

2-Amino-6-[3-(1-aminoethyl)pyrrolidin-1-yl]-4-cyclopropyl-7-fluoro-5-methoxy-8-methylpyrido[1,2-c]pyrimidine-1,3-dione;

2,8-Diamino-6-[3-(1-aminoethyl)pyrrolidin-1-yl]-4-cyclopropyl-7-fluoro-5-methylpyrido[1,2-c]pyrimidine-1,3-dione;

2,8-Diamino-6-(3-aminomethyl-4-fluoropyrrolidin-1-yl)-4-cyclopropyl-7-fluoro-5-methylpyrido[1,2-c]pyrimidine-1,3-dione;

2-Amino-6-(3-aminomethyl-4-fluoropyrrolidin-1-yl)-4-cyclopropyl-7-fluoro-5,8-dimethylpyrido[1,2-c]pyrimidine-1,3-dione;

2-Amino-6-[3-(1-amino-2,2-difluoroethyl)pyrrolidin-1-yl]-4-cyclopropyl-7-fluoro-5,8-dimethylpyrido[1,2-c]pyrimidine-1,3-dione;

2-Amino-6-[3-(1-amino-2,2-difluoroethyl)pyrrolidin-1-yl]-4-cyclopropyl-7-fluoro-5-methoxy-8-methylpyrido[1,2-c]pyrimidine-1,3-dione;

2-Amino-6-(4-aminomethyl-4,5,6,7-tetrahydrobenzo[b]thiophen-2-yl)-4-cyclopropyl-7-fluoro-5-methoxy-8-methylpyrido[1,2-c]pyrimidine-1,3-dione;

2-Amino-6-(4-aminomethyl-4,5,6,7-tetrahydrobenzo[b]thiophen-2-yl)-4-cyclopropyl-7-fluoro-5,8-dimethylpyrido[1,2-c]pyrimidine-1,3-dione;

2-Amino-6-(4-aminomethyl-4,5,6,7-tetrahydrobenzo[b]thiophen-2-yl)-4-cyclopropyl-7-fluoro-5-methylpyrido[1,2-c]pyrimidine-1,3-dione;

2-Amino-4-cyclopropyl-6-[3-(1,2-dihydroxyethyl)pyrrolidin-1-yl]-7-fluoro-5-methoxy-8-methylpyrido[1,2-c]pyrimidine-1,3-dione;

2-Amino-4-cyclopropyl-6-[3-(1,2-dihydroxyethyl)pyrrolidin-1-yl]-7-fluoro-5,8-dimethylpyrido[1,2-c]pyrimidine-1,3-dione;

2-Amino-4-cyclopropyl-6-[3-(1,2-dihydroxyethyl)pyrrolidin-1-yl]-7-fluoro-5-methylpyrido[1,2-c]pyrimidine-1,3-dione;

2-Amino-4-cyclopropyl-6-[3-(1,2-dihydroxyethyl)pyrrolidin-1-yl]-7-fluoro-5-methoxypyrido[1,2-c]pyrimidine-1,3-dione;

2-Amino-6-[3-(1-amino-2-hydroxyethyl)pyrrolidin-1-yl]-4-cyclopropyl-7-fluoro-5-methoxypyrido[1,2-c]pyrimidine-1,3-dione;

2-Amino-6-[3-(1-amino-2-hydroxyethyl)pyrrolidin-1-yl]-4-cyclopropyl-7-fluoro-5-methoxy-8-methylpyrido[1,2-c]pyrimidine-1,3-dione;

2-Amino-6-[3-(1-amino-2-hydroxyethyl)pyrrolidin-1-yl]-4-cyclopropyl-7-fluoro-5,8-dimethylpyrido[1,2-c]pyrimidine-1,3-dione;

2-Amino-6-[3-(1-amino-1-methylethyl)pyrrolidine-1-yl]-4-cyclopropyl-7-fluoro-5-methoxypyrido[1,2-c]pyrimidine-1,3-dione; and 6-Chloro-4-cyclopropyl-7-fluoro-5-methoxypyrido[1,2-c]pyrimidine-1,3-dione;

6-Chloro-4-cyclopropyl-7-fluoro-5-methoxy-8-methylpyrido[1,2-c]pyrimidine-1,3-dione;

6-Chloro-4-cyclopropyl-7-fluoro-5,8-dimethylpyrido[1,2-c]pyrimidine-1,3-dione;

2-Amino-6-chloro-4-cyclopropyl-7-fluoro-5-methoxypyrido[1,2-c]pyrimidine-1,3-dione;

2-Amino-6-chloro-4-cyclopropyl-7-fluoro-5-methoxy-8-methylpyrido[1,2-c]pyrimidine-1,3-dione;

2-Amino-6-chloro-4-cyclopropyl-7-fluoro-5,8-dimethylpyrido[1,2-c]pyrimidine-1,3-dione;

8-Amino-6-hloro-4-cyclopropyl-7-fluoro-5-methylpyrido[1,2-c]pyrimidine-1,3-dione;

2,8-Diamino-6-hloro-4-cyclopropyl-7-fluoro-5-methylpyrido[1,2-c]pyrimidine-1,3-dione;

or a pharmaceutically acceptable salt thereof.

The invention also provides a compound which is:

4-Cyclopropyl-7-fluoro-5-methyl-6-[3-(1-methylaminoethyl)pyrrolidin-1-yl]pyrido[1,2-c]pyrimidine-1,3-dione;

4-Cyclopropyl-7-fluoro-5-methyl-6-pyrrolidin-1-ylpyrido[1,2-c]pyrimidine-1,3-dione;

4-Cyclopropyl-7-fluoro-6-[3-(1-hydroxyethyl)pyrrolidin-1-yl-5-methylpyrido[1,2-c]pyrimidine-1,3-dione;

6-[(R)-3-((R)-1-Aminoethyl)-pyrrolidin-1-yl]-4-cyclopropyl-7-fluoro-5-methylpyrido[1,2-c]pyrimidine-1,3-dione hydrochloride;

6-[(R)-3-((S)-1-Aminoethyl)-pyrrolidin-1-yl]-4-cyclopropyl-7-fluoro-5-methylpyrido[1,2-c]pyrimidine-1,3-dione hydrochloride;

6-[4-(1-Aminoethyl)-3,3-dimethylpyrrolidin-1-yl]-4-cyclopropyl-7-fluoro-5-methylpyrido[1,2-c]pyrimidine-1,3-dione hydrochloride;

6-(3-Aminopyrrolidin-1-yl)-4-cyclopropyl-7-fluoro-5-methyl-pyrido[1,2-c]pyrimidine-1,3-dione hydrochloride;

6-[3-(1-Aminoethyl)-4-methylpyrrolidin-1-yl]-4-cyclopropyl-7-fluoro-5-methylpyrido[1,2-c]pyrimidine-1,3-dione hydrochloride;

6-[3-(1-Amino-1-phenylmethyl)pyrrolidin-1-yl]-4-cyclopropyl-7-fluoro-5-methylpyrido[1,2-c]pyrimidine-1,3-dione;

6-{3-[1-Amino-1-(2-fluorophenyl)methyl]pyrrolidin-1-yl}-4-cyclopropyl-7-fluoro-5-methylpyrido[1,2-c]pyrimidine-1,3-dione;

6-{3-[1-Amino-1-(4-fluorophenyl)methyl]pyrrolidin-1-yl}-4-cyclopropyl-7-fluoro-5-methylpyrido[1,2-c]pyrimidine-1,3-dione;

6-{3-[1-Amino-1-(2,4-difluorophenyl)methyl]pyrrolidin-1-yl}-4-cyclopropyl-7-fluoro-5-methylpyrido[1,2-c]pyrimidine-1,3-dione;

6-{3-[1-Amino-1-(2,6-difluorophenyl)methyl]pyrrolidin-1-yl}-4-cyclopropyl-7-fluoro-5-methylpyrido[1,2-c]pyrimidine-1,3-dione;

6-{3-[1-Amino-1-(2,4,6-trifluorophenyl)methyl]pyrrolidin-1-yl}-4-cyclopropyl-7-fluoro-5-methylpyrido[1,2-c]pyrimidine-1,3-dione;

6-[3-(1-Aminopropyl)pyrrolidin-1-yl]-4-cyclopropyl-7-fluoro-5-methylpyrido[1,2-c]pyrimidine-1,3-dione;

6-[3-(1-Amino-2-methylpropyl)pyrrolidin-1-yl]-4-cyclopropyl-7-fluoro-5-methylpyrido[1,2-c]pyrimidine-1,3-dione;

6-[3-(1-Amino-2-cyclopropylmethyl)pyrrolidin-1-yl]-4-cyclopropyl-7-fluoro-5-methylpyrido[1,2-c]pyrimidine-1,3-dione;

6-[3-(1-Aminocyclopropyl)pyrrolidin-1-yl]-4-cyclopropyl-7-fluoro-5-methylpyrido[1,2-c]pyrimidine-1,3-dione;

6-[3-(1-Aminocyclopropyl)-4-fluoropyrrolidin-1-yl]-4-cyclopropyl-7-fluoro-5-methylpyrido[1,2-c]pyrimidine-1,3-dione;

6-[3-(1-Amino-1-phenylmethyl)-4-fluoropyrrolidin-1-yl]-4-cyclopropyl-7-fluoro-5-methylpyrido[1,2-c]pyrimidine-1,3-dione;

6-[3-(1-Amino-2-fluoroethyl)pyrrolidin-1-yl]-4-cyclopropyl-7-fluoro-5-methylpyrido[1,2-c]pyrimidine-1,3-dione;

6-[3-(1-Amino-2,2-difluorocyclopropyl)pyrrolidin-1-yl]-4-cyclopropyl-7-fluoro-5-methylpyrido[1,2-c]pyrimidine-1,3-dione;

6-[3-(1-Aminoethyl)pyrrolidin-1-yl]-4-cyclopropyl-7-fluoro-5-methylpyrido[1,2-c]pyrimidine-1,3-dione;

6-[3-(1-Amino-2-fluorocyclopropyl)pyrrolidin-1-yl]-4-cyclopropyl-7-fluoro-5-methylpyrido[1,2-c]pyrimidine-1,3-dione;

6-[3-(1-Amino-1-methylethyl)pyrrolidin-1-yl]-4-cyclopropyl-7-fluoro-5-methylpyrido[1,2-c]pyrimidine-1,3-dione;

6-[3-(1-Aminoethyl)-4-fluoropyrrolidin-1-yl]-4-cyclopropyl-7-fluoro-5-methylpyrido[1,2-c]pyrimidine-1,3-dione;

6-[3-(1-Amino-1-pyridin-2-ylmethyl)pyrrolidin-1-yl]-4-cyclopropyl-7-fluoro-5-methylpyrido[1,2-c]pyrimidine-1,3-dione;

6-[3-(1-Amino-2-fluorocyclopropyl)-4-fluoropyrrolidin-1-yl]-4-cyclopropyl-7-fluoro-5-methylpyrido[1,2-c]pyrimidine-1,3-dione;

6-[3-(1-Amino-1-pyridin-3-ylmethyl)pyrrolidin-1-yl]-4-cyclopropyl-7-fluoro-5-methylpyrido[1,2-c]pyrimidine-1,3-dione;

6-[3-(1-Amino-1-pyridin-4-ylmethyl)pyrrolidin-1-yl]-4-cyclopropyl-7-fluoro-5-methylpyrido[1,2-c]pyrimidine-1,3-dione;

6-(4-Aminohexahydrocyclopenta[c]pyrrol-2-yl)-4-cyclopropyl-7-fluoro-5-methylpyrido[1,2-c]pyrimidine-1,3-dione;

6-(4-Amino-5-fluorohexahydrocyclopenta[c]pyrrol-2-yl)-4-cyclopropyl-7-fluoro-5-methylpyrido[1,2-c]pyrimidine-1,3-dione;

4-Cyclopropyl-7-fluoro-5-methyl-6-(3-phenylpyrrolidin-1-yl)pyrido[1,2-c]pyrimidine-1,3-dione;

4-Cyclopropyl-7-fluoro-5-methyl-6-(3-pyridin-2-ylpyrrolidin-1-yl)pyrido[1,2-c]pyrimidine-1,3-dione;

4-Cyclopropyl-7-fluoro-5-methyl-6-(3-pyridin-3-ylpyrrolidin-1-yl)pyrido[1,2-c]pyrimidine-1,3-dione;

4-Cyclopropyl-7-fluoro-5-methyl-6-(3-pyridin-4-ylpyrrolidin-1-yl)pyrido[1,2-c]pyrimidine-1,3-dione;

4-Cyclopropyl-7-fluoro-5-methyl-6-(piperazin-1-yl)pyrido[1,2-c]pyrimidine-1,3-dione;

4-Cyclopropyl-7-fluoro-5-methyl-6-(4-methylpiperazin-1-yl)pyrido[1,2-c]pyrimidine-1,3-dione;

N-{1-[1-(4-Cyclopropyl-7-fluoro-5-methyl-1,3-dioxo-2,3-dihydro-1H-pyrido[1,2-c]pyrimidin-6-yl)pyrrolidin-3-yl]ethyl}methanesulfonamide;

4-Cyclopropyl-7-fluoro-5-methyl-6(octahydropyrrolo[3,4-b]pyridin-6-yl)pyrido[1,2-c]pyrimidine-1,3-dione;

6-(7-Amino-5-azaspiro[2.4]hept-5-yl)-4-cyclopropyl-7-fluoro-5-methylpyrido[1,2-c]pyrimidine-1,3-dione;

4-Cyclopropyl-7-fluoro-5-methyl-6-(thiophen-3-yl)pyrido[1,2-c]pyrimidine-1,3-dione;

4-Cyclopropyl-7-fluoro-5-methyl-6-(1-methyl-2,3-dihydro-1H-isoindol-5-yl)pyrido[1,2-c]pyrimidine-1,3-dione;

4-Cyclopropyl-7-fluoro-6-(7-hydroxymethyl-5-azaspiro[2.4]hept-5-yl)-5-methylpyrido[1,2-c]pyrimidine-1,3-dione;

6-(3-Amino-4-methoxyiminopyrrolidin-1-yl)-4-cyclopropyl-7-fluoro-5-methylpyrido[1,2-c]pyrimidine-1,3-dione;

4-cyclopropyl-7-fluoro-5-methyl-6-(3-methylaminomethylpyrrolidin-1-yl)pyrido[1,2-c]pyrimidine-1,3-dione;

6-(5-Aminomethylthiophen-3-yl)-4-cyclopropyl-7-fluoro-5-methylpyrido[1,2-c]pyrimidine-1,3-dione;

6-[3-(1-Aminoethyl)-3-fluoropyrrolidin-1-yl]-4-cyclopropyl-7-fluoro-5-methylpyrido[1,2-c]pyrimidine-1,3-dione;

6-(5-Aminomethylthiophen-3-yl)-4-cyclopropyl-7-fluoro-5-methylpyrido[1,2-c]pyrimidine-1,3-dione;

6-(5-Aminomethylthiophen-2-yl)-4-cyclopropyl-7-fluoro-5-methylpyrido[1,2-c]pyrimidine-1,3-dione;

6-(4-Aminomethylthiophen-2-yl)-4-cyclopropyl-7-fluoro-5-methylpyrido[1,2-c]pyrimidine-1,3-dione;

6-(4-Aminomethylthiophen-3-yl)-4-cyclopropyl-7-fluoro-5-methylpyrido[1,2-c]pyrimidine-1,3-dione;

4-Cyclopropyl-6-(5,6-dihydro-4H-thieno[2,3-c]pyrrol-3-yl)-7-fluoro-5-methylpyrido[1,2-c]pyrimidine-1,3-dione;

4-Cyclopropyl-6-(5,6-dihydro-4H-thieno[2,3-c]pyrrol-2-yl)-7-fluoro-5-methylpyrido[1,2-c]pyrimidine-1,3-dione;

4-Cyclopropyl-7-fluoro-5-methyl-6-(6-methyl-5,6-dihydro-4H-thieno[2,3-c]pyrrol-2-yl)pyrido[1,2-c]pyrimidine-1,3-dione;

4-Cyclopropyl-7-fluoro-5-methyl-6-(6-methyl-5,6-dihydro-4H-thieno[2,3-c]pyrrol-3-yl)pyrido[1,2-c]pyrimidine-1,3-dione;

4-Cyclopropyl-7-fluoro-5-methyl-6-(5-pyridin-4-ylthiophen-3-yl)pyrido[1,2-c]pyrimidine-1,3-dione;

4-Cyclopropyl-7-fluoro-5-methyl-6-(5-pyridin-3-ylthiophen-3-yl)pyrido[1,2-c]pyrimidine-1,3-dione;

4-Cyclopropyl-7-fluoro-5-methyl-6-(5-pyridin-2-ylthiophen-3-yl)pyrido[1,2-c]pyrimidine-1,3-dione;

4-Cyclopropyl-7-fluoro-5-methyl-6-(4-pyridin-4-ylthiophen-3-yl)pyrido[1,2-c]pyrimidine-1,3-dione;

4-Cyclopropyl-7-fluoro-5-methyl-6-(4-pyridin-3-ylthiophen-3-yl)pyrido[1,2-c]pyrimidine-1,3-dione;

4-Cyclopropyl-7-fluoro-5-methyl-6-(4-pyridin-2-ylthiophen-3-yl)pyrido[1,2-c]pyrimidine-1,3-dione;

4-Cyclopropyl-7-fluoro-5-methyl-6-pyridin-4-ylpyrido[1,2-c]pyrimidine-1,3-dione;

6-(4-Aminomethylpyridin-2-yl)-4-cyclopropyl-7-fluoro-5-methylpyrido[1,2-c]pyrimidine-1,3-dione;

6-(5-Aminomethylpyridin-2-yl)-4-cyclopropyl-7-fluoro-5-methylpyrido[1,2-c]pyrimidine-1,3-dione;

6-(6-Aminomethylpyridin-2-yl)-4-cyclopropyl-7-fluoro-5-methylpyrido[1,2-c]pyrimidine-1,3-dione;

6-(5-Aminomethylpyrimidin-2-yl)-4-cyclopropyl-7-fluoro-5-methylpyrido[1,2-c]pyrimidine-1,3-dione;

4-Cyclopropyl-7-fluoro-5-methyl-6-pyrimidin-2-ylpyrido[1,2-c]pyrimidine-1,3-dione;

6-(2-Aminomethylpyrimidin-5-yl)-4-cyclopropyl-7-fluoro-5-methylpyrido[1,2-c]pyrimidine-1,3-dione;

4-Cyclopropyl-7-fluoro-5-methyl-6-pyrimidin-5-ylpyrido[1,2-c]pyrimidine-1,3-dione;

4-Cyclopropyl-7-fluoro-5-methyl-6-pyrazin-2-ylpyrido[1,2-c]pyrimidine-1,3-dione;

6-(6-Aminomethylpyrazin-2-yl)-4-cyclopropyl-7-fluoro-5-methylpyrido[1,2-c]pyrimidine-1,3-dione;

6-[3-(6-Aminomethylpyridin-2-yl)pyrrolidin-1-yl]-4-cyclopropyl-7-fluoro-5-methylpyrido[1,2-c]pyrimidine-1,3-dione;

6-[3-(2-Aminomethylpyridin-3-yl)pyrrolidin-1-yl]-4-cyclopropyl-7-fluoro-5-methylpyrido[1,2-c]pyrimidine-1,3-dione;

6-[5-(2-Aminomethylpyridin-3-yl)thiophen-3-yl]-4-cyclopropyl-7-fluoro-5-methylpyrido[1,2-c]pyrimidine-1,3-dione;

6-[5-(2-Aminomethylpyridin-3-yl)thiophen-2-yl]-4-cyclopropyl-7-fluoro-5-methylpyrido[1,2-c]pyrimidine-1,3-dione;

6-[5-(6-Aminomethylpyridin-2-yl)thiophen-2-yl]-4-cyclopropyl-7-fluoro-5-methylpyrido[1,2-c]pyrimidine-1,3-dione;

6-[5-(6-Aminomethylpyridin-2-yl)thiophen-3-yl]-4-cyclopropyl-7-fluoro-5-methylpyrido[1,2-c]pyrimidine-1,3-dione;

6-[4-(2-Aminomethylpyridin-3-yl)thiophen-2-yl]-4-cyclopropyl-7-fluoro-5-methylpyrido[1,2-c]pyrimidine-1,3-dione;

6-[3-(2-Aminomethylpyridin-3-yl)thiophen-2-yl]-4-cyclopropyl-7-fluoro-5-methylpyrido[1,2-c]pyrimidine-1,3-dione;

6-[4-(6-Aminomethylpyridin-2-yl)thiophen-3-yl]-4-cyclopropyl-7-fluoro-5-methylpyrido[1,2-c]pyrimidine-1,3-dione;

4-Cyclopropyl-7-fluoro-5-methyl-6-(4-pyridin-4-ylthiophen-2-yl)pyrido[1,2-c]pyrimidine-1,3-dione; and 6-[4-(1-Aminoethyl)thiophen-2-yl]-4-cyclopropyl-7-fluoro-5-methylpyrido[1,2-c]pyrimidine-1,3-dione;

4-Cyclopropyl-7-fluoro-5-methoxy-6-[3-(1-methylaminoethyl)pyrrolidin-1-yl]pyrido[1,2-c]pyrimidine-1,3-dione;

4-Cyclopropyl-7-fluoro-5-methoxy-6-pyrrolidin-1-ylpyrido[1,2-c]pyrimidine-1,3-dione;

4-Cyclopropyl-7-fluoro-6-[3-(1-hydroxyethyl)pyrrolidin-1-yl]-5-methoxypyrido[1,2-c]pyrimidine-1,3-dione;

6-[(R)-3-((R)-1-Aminoethyl)-pyrrolidin-1-yl]-4-cyclopropyl-7-fluoro-5-methoxypyrido[1,2-c]pyrimidine-1,3-dione;

6-[(R)-3-((S)-1-Aminoethyl)-pyrrolidin-1-yl]-4-cyclopropyl-7-fluoro-5-methoxypyrido[1,2-c]pyrimidine-1,3-dione;

6-[4-(1-Aminoethyl)-3,3-dimethylpyrrolidin-1-yl]-4-cyclopropropyl-7-fluoro-5-methoxypyrido[1,2-c]pyrimidine-1,3-dione;

6-(3-Aminopyrrolidin-1-yl)-4-cyclopropyl-7-fluoro-5-methoxypyrido[1,2-c]pyrimidine-1,3-dione;

6-[3-(1-Aminoethyl)-4-methylpyrrolidin-1-yl]-4-cyclopropyl-7-fluoro-5-methoxypyrido[1,2-c]pyrimidine-1,3-dione;

6-[3-(1-Amino-1-phenylmethyl)pyrrolidin-1-yl]-4-cyclopropyl-7-fluoro-5-methoxypyrido[1,2-c]pyrimidine-1,3-dione;

6-{3-[1-Amino-1-(2-fluorophenyl)methyl]pyrrolidin-1-yl}-4-cyclopropyl-7-fluoro-5-methoxypyrido[1,2-c]pyrimidine-1,3-dione;

6-{3-[1-Amino-1-(4-fluorophenyl)methyl]pyrrolidin-1-yl}-4-cyclopropyl-7-fluoro-5-methoxypyrido[1,2-c]pyrimidine-1,3-dione;

6-{3-[1-Amino-1-(2,4-difluorophenyl)methyl]pyrrolidin-1-yl}-4-cyclopropyl-7-fluoro-5-methoxypyrido[1,2-c]pyrimidine-1,3-dione;

6-{3-[1-Amino-1-(2,6-difluorophenyl)methyl]pyrrolidin-1-yl}-4-cyclopropyl-7-fluoro-5-methoxypyrido[1,2-c]pyrimidine-1,3-dione;

6-{3-[1-Amino-1-(2,4,6-trifluorophenyl)methyl]pyrrolidin-1-yl}-4-cyclopropyl-7-fluoro-5-methoxypyrido[1,2-c]pyrimidine-1,3-dione;

6-[3-(1-Aminopropyl)pyrrolidin-1-yl]-4-cyclopropyl-7-fluoro-5-methoxypyrido[1,2-c]pyrimidine-1,3-dione;

6-[3-(1-Amino-2-methylpropyl)pyrrolidin-1-yl]-4-cyclopropyl-7-fluoro-5-methoxypyrido[1,2-c]pyrimidine-1,3-dione;

6-[3-(1-Amino-2-cyclopropylmethyl)pyrrolidin-1-yl]-4-cyclopropyl-7-fluoro-5-methoxypyrido[1,2-c]pyrimidine-1,3-dione;

6-[3-(1-Aminocyclopropyl)pyrrolidin-1-yl]-4-cyclopropyl-7-fluoro-5-methoxypyrido[1,2-c]pyrimidine-1,3-dione;

6-[3-(1-Aminocyclopropyl)-4-fluoropyrrolidin-1-yl]-4-cyclopropyl-7-fluoro-5-methoxypyrido[1,2-c]pyrimidine-1,3-dione;

6-[3-(1-Amino-1-phenylmethyl)-4-fluoropyrrolidin-1-yl]-4-cyclopropyl-7-fluoro-5-methoxypyrido[1,2-c]pyrimidine-1,3-dione;

6-[3-(1-Amino-2-fluoroethyl)pyrrolidin-1-yl]-4-cyclopropyl-7-fluoro-5-methoxypyrido[1,2-c]pyrimidine-1,3-dione;

6-[3-(1-Amino-2,2-difluorocyclopropyl)pyrrolidin-1-yl]-4-cyclopropyl-7-fluoro-5-methoxypyrido[1,2-c]pyrimidine-1,3-dione;

6-[3-(1-Aminoethyl)pyrrolidin-1-yl]-4-cyclopropyl-7-fluoro-5-methoxypyrido[1,2-c]pyrimidine-1,3-dione;

6-[3-(1-Amino-2-fluorocyclopropyl)pyrrolidin-1-yl]-4-cyclopropyl-7-fluoro-5-methoxypyrido[1,2-c]pyrimidine-1,3-dione;

6-[3-(1-Amino-1-methylethyl)pyrrolidin-1-yl]-4-cyclopropyl-7-fluoro-5-methoxypyrido[1,2-c]pyrimidine-1,3-dione;

6-[3-(1-Aminoethyl)-4-fluoropyrrolidin-1-yl]-4-cyclopropyl-7-fluoro-5-methoxypyrido[1,2-c]pyrimidine-1,3-dione;

6-[3-(1-Amino-1-pyridin-2-ylmethyl)pyrrolidin-1-yl]-4-cyclopropyl-7-fluoro-5-methoxypyrido[1,2-c]pyrimidine-1,3-dione;

6-[3-(1-Amino-2-fluorocyclopropyl)-4-fluoropyrrolidin-1-yl]-4-cyclopropyl-7-fluoro-5-methoxypyrido[1,2-c]pyrimidine-1,3-dione;

6-[3-(1-Amino-1-pyridin-3-ylmethyl)pyrrolidin-1-yl]-4-cyclopropyl-7-fluoro-5-methoxypyrido[1,2-c]pyrimidine-1,3-dione;

6-[3-(1-Amino-1-pyridin-4-ylmethyl)pyrrolidin-1-yl]-4-cyclopropyl-7-fluoro-5-methoxypyrido[1,2-c]pyrimidine-1,3-dione;

6-(4-Aminohexahydrocyclopenta[c]pyrrol-2-yl)-4-cyclopropyl-7-fluoro-5-methoxypyrido[1,2-c]pyrimidine-1,3-dione;

6-(4-Amino-5-fluorohexahydrocyclopenta[c]pyrrol-2-yl)-4-cyclopropyl-7-fluoro-5-methoxypyrido[1,2-c]pyrimidine-1,3-dione;

4-Cyclopropyl-7-fluoro-5-methoxy-6-(3-phenylpyrrolidin-1-yl)pyrido[1,2-c]pyrimidine-1,3-dione;

4-Cyclopropyl-7-fluoro-5-methoxy-6-(3-pyridin-2-ylpyrrolidin-1-yl)pyrido[1,2-c]pyrimidine-1,3-dione;

4-Cyclopropyl-7-fluoro-5-methoxy-6-(3-pyridin-3-ylpyrrolidin-1-yl)pyrido[1,2-c]pyrimidine-1,3-dione;

4-Cyclopropyl-7-fluoro-5-methoxy-6-(3-pyridin-4-ylpyrrolidin-1-yl)pyrido[1,2-c]pyrimidine-1,3-dione;

4-Cyclopropyl-7-fluoro-5-methoxy-6-(piperazin-1-yl)pyrido[1,2-c]pyrimidine-1,3-dione;

4-Cyclopropyl-7-fluoro-5-methoxy-6-(4-methylpiperazin-1-yl)pyrido[1,2-c]pyrimidine-1,3-dione;

N-{1-[1-(4-Cyclopropyl-7-fluoro-5-methoxy-1,3-dioxo-2,3-dihydro-1H-pyrido[1,2-c]pyrimidin-6-yl)pyrrolidin-3-yl]ethyl}methanesulfonamide, 4-Cyclopropyl-7-fluoro-5-methoxy-6(octahydropyrrolo[3,4-b]pyridin-6-yl)pyrido[1,2-c]pyrimidine-1,3-dione;

6-(7-Amino-5-azaspiro[2.4]hept-5-yl)-4-cyclopropyl-7-fluoro-5-methoxypyrido[1,2-c]pyrimidine-1,3-dione;

4-Cyclopropyl-7-fluoro-5-methoxy-6-(thiophen-3-yl)pyrido[1,2-c]pyrimidine-1,3-dione;

4-Cyclopropyl-7-fluoro-5-methoxy-6-(1-methyl-2,3-dihydro-1H-isoindol-5-yl)pyrido[1,2-c]pyrimidine-1,3-dione;

4-Cyclopropyl-7-fluoro-6-(7-hydroxymethyl-5-azaspiro[2.4]hept-5-yl)-5-methoxypyrido[1,2-c]pyrimidine-1,3-dione;

6-(3-Amino-4-methoxyiminopyrrolidin-1-yl)-4-cyclopropyl-7-fluoro-5-methoxypyrido[1,2-c]pyrimidine-1,3-dione;

4-cyclopropyl-7-fluoro-5-methoxy-6-(3-methylaminomethylpyrrolidin-1-yl)pyrido[1,2-c]pyrimidine-1,3-dione;

6-(5-Aminomethylthiophen-3-yl)-4-cyclopropyl-7-fluoro-5-methoxypyrido[1,2-c]pyrimidine-1,3-dione;

6-[3-(1-Aminoethyl)-3-fluoropyrrolidin-1-yl]-4-cyclopropyl-7-fluoro-5-methoxypyrido[1,2-c]pyrimidine-1,3-dione;

6-(5-Aminomethylthiophen-3-yl)-4-cyclopropyl-7-fluoro-5-methoxypyrido[1,2-c]pyrimidine-1,3-dione;

6-(5-Aminomethylthiophen-2-yl)-4-cyclopropyl-7-fluoro-5-methoxypyrido[1,2-c]pyrimidine-1,3-dione;

6-(4-Aminomethylthiophen-2-yl)-4-cyclopropyl-7-fluoro-5-methoxypyrido[1,2-c]pyrimidine-1,3-dione;

6-(4-Aminomethylthiophen-3-yl)-4-cyclopropyl-7-fluoro-5-methoxypyrido[1,2-c]pyrimidine-1,3-dione;

4-Cyclopropyl-6-(5,6-dihydro-4H-thieno[2,3-c]pyrrol-3-yl)-7-fluoro-5-methoxypyrido[1,2-c]pyrimidine-1,3-dione;

4-Cyclopropyl-6-(5,6-dihydro-4H-thieno[2,3-c]pyrrol-2-yl)-7-fluoro-5-methoxypyrido[1,2-c]pyrimidine-1,3-dione;

4-Cyclopropyl-7-fluoro-5-methoxy-6-(6-methyl-5,6-dihydro-4H-thieno[2,3-c]pyrrol-2-yl)pyrido[1,2-c]pyrimidine-1,3-dione;

4-Cyclopropyl-7-fluoro-5-methoxy-6-(6-methyl-5,6-dihydro-4H-thieno[2,3-c]pyrrol-3-yl)pyrido[1,2-c]pyrimidine-1,3-dione;

4-Cyclopropyl-7-fluoro-5-methoxy-6-(5-pyridin-4-ylthiophen-3-yl)pyrido[1,2-c]pyrimidine-1,3-dione;

4-Cyclopropyl-7-fluoro-5-methoxy-6-(5-pyridin-3-ylthiophen-3-yl)pyrido[1,2-c]pyrimidine-1,3-dione;

4-Cyclopropyl-7-fluoro-5-methoxy-6-(5-pyridin-2-ylthiophen-3-yl)pyrido[1,2-c]pyrimidine-1,3-dione;

4-Cyclopropyl-7-fluoro-5-methoxy-6-(4-pyridin-4-ylthiophen-3-yl)pyrido[1,2-c]pyrimidine-1,3-dione;

4-Cyclopropyl-7-fluoro-5-methoxy-6-(4-pyridin-3-ylthiophen-3-yl)pyrido[1,2-c]pyrimidine-1,3-dione;

4-Cyclopropyl-7-fluoro-5-methoxy-6-(4-pyridin-2-ylthiophen-3-yl)pyrido[1,2-c]pyrimidine-1,3-dione;

4-Cyclopropyl-7-fluoro-5-methoxy-6-pyridin-4-ylpyrido[1,2-c]pyrimidine-1,3-dione;

6-(4-Aminomethylpyridin-2-yl]-4-cyclopropyl-7-fluoro-5-methoxypyrido[1,2-c]pyrimidine-1,3-dione;

6-(5-Aminomethylpyridin-2-yl]-4-cyclopropyl-7-fluoro-5-methoxypyrido[1,2-c]pyrimidine-1,3-dione;

6-(6-Aminomethylpyridin-2-yl]-4-cyclopropyl-7-fluoro-5-methoxypyrido[1,2-c]pyrimidine-1,3-dione;

6-(5-Aminomethylpyrimidin-2-yl]-4-cyclopropyl-7-fluoro-5-methoxypyrido[1,2-c]pyrimidine-1,3-dione;

4-Cyclopropyl-7-fluoro-5-methoxy-6-pyrimidin-2-ylpyrido[1,2-c]pyrimidine-1,3-dione;

6-(2-Aminomethylpyrimidin-5-yl]-4-cyclopropyl-7-fluoro-5-methoxypyrido[1,2-c]pyrimidine-1,3-dione;

4-Cyclopropyl-7-fluoro-5-methoxy-6-pyrimidin-5-ylpyrido[1,2-c]pyrimidine-1,3-dione;

4-Cyclopropyl-7-fluoro-5-methoxy-6-pyrazin-2-ylpyrido[1,2-c]pyrimidine-1,3-dione;

6-(6-Aminomethylpyrazin-2-yl]-4-cyclopropyl-7-fluoro-5-methoxypyrido[1,2-c]pyrimidine-1,3-dione;

6-[3-(6-Aminomethylpyridin-2-yl)pyrrolidin-1-yl]-4-cyclopropyl-7-fluoro-5-methoxypyrido[1,2-c]pyrimidine-1,3-dione;

6-[3-(2-Aminomethylpyridin-3-yl)pyrrolidin-1-yl]-4-cyclopropyl-7-fluoro-5-methoxypyrido[1,2-c]pyrimidine-1,3-dione;

6-[5-(2-Aminomethylpyridin-3-yl)thiophen-3-yl]-4-cyclopropyl-7-fluoro-5-methoxypyrido[1,2-c]pyrimidine-1,3-dione;

6-[5-(2-Aminomethylpyridin-3-yl)thiophen-2-yl]-4-cyclopropyl-7-fluoro-5-methoxypyrido[1,2-c]pyrimidine-1,3-dione;

6-[5-(6-Aminomethylpyridin-2-yl)thiophen-2-yl]-4-cyclopropyl-7-fluoro-5-methoxypyrido[1,2-c]pyrimidine-1,3-dione;

6-[5-(6-Aminomethylpyridin-2-yl)thiophen-3-yl]-4-cyclopropyl-7-fluoro-5-methoxypyrido[1,2-c]pyrimidine-1,3-dione;

6-[4-(2-Aminomethylpyridin-3-yl)thiophen-2-yl]-4-cyclopropyl-7-fluoro-5-methoxypyrido[1,2-c]pyrimidine-1,3-dione;

6-[3-(2-Aminomethylpyridin-3-yl)thiophen-2-yl]-4-cyclopropyl-7-fluoro-5-methoxypyrido[1,2-c]pyrimidine-1,3-dione;

6-[4-(6-Aminomethylpyridin-2-yl)thiophen-3-yl]-4-cyclopropyl-7-fluoro-5-methoxypyrido[1,2-c]pyrimidine-1,3-dione;

6-[3-(1-Aminoethyl)pyrrolidin-1-yl]-4-cyclopropyl-7-fluoro-5,8-dimethylpyrido[1,2-c]pyrimidine-1,3-dione;

6-[3-(1-Aminoethyl)pyrrolidin-1-yl]-4-cyclopropyl-7-fluoro-5-methoxy-8-methylpyrido[1,2-c]pyrimidine-1,3-dione;

8-Amino-6-[3-(1-aminoethyl)pyrrolidin-1-yl]-4-cyclopropyl-7-fluoro-5-methylpyrido[1,2-c]pyrimidine-1,3-dione;

8-Amino-6-(3-aminomethyl-4-fluoropyrrolidin-1-yl)-4-cyclopropyl-7-fluoro-5-methylpyrido[1,2-c]pyrimidine-1,3-dione;

6-(3-Aminomethyl-4-fluoropyrrolidin-1-yl)-4-cyclopropyl-7-fluoro-5,8-dimethylpyrido[1,2-c]pyrimidine-1,3-dione;

6-[3-(1-Amino-2,2-difluoroethyl)pyrrolidin-1-yl]-4-cyclopropyl-7-fluoro-5,8-dimethylpyrido[1,2-c]pyrimidine-1,3-dione;

6-[3-(1-Amino-2,2-difluoroethyl)pyrrolidin-1-yl]-4-cyclopropyl-7-fluoro-5-methoxy-8-methylpyrido[1,2-c]pyrimidine-1,3-dione;

6-(4-Aminomethyl-4,5,6,7-tetrahydrobenzo[b]thiophen-2-yl)-4-cyclopropyl-7-fluoro-5-methoxy-8-methylpyrido[1,2-c]pyrimidine-1,3-dione;

6-(4-Aminomethyl-4,5,6,7-tetrahydrobenzo[b]thiophen-2-yl)-4-cyclopropyl-7-fluoro-5,8-dimethylpyrido[1,2-c]pyrimidine-1,3-dione;

6-(4-Aminomethyl-4,5,6,7-tetrahydrobenzo[b]thiophen-2-yl)-4-cyclopropyl-7-fluoro-5-methylpyrido[1,2-c]pyrimidine-1,3-dione;

4-Cyclopropyl-6-[3-(1,2-dihydroxyethyl)pyrrolidin-1-yl]-7-fluoro-5-methoxy-8-methylpyrido[1,2-c]pyrimidine-1,3-dione;

4-Cyclopropyl-6-[3-(1,2-dihydroxyethyl)pyrrolidin-1-yl]-7-fluoro-5,8-dimethylpyrido[1,2-c]pyrimidine-1,3-dione;

4-Cyclopropyl-6-[3-(1,2-dihydroxyethyl)pyrrolidin-1-yl]-7-fluoro-5-methylpyrido[1,2-c]pyrimidine-1,3-dione;

4-Cyclopropyl-6-[3-(1,2-dihydroxyethyl)pyrrolidin-1-yl]-7-fluoro-5-methoxypyrido[1,2-c]pyrimidine-1,3-dione;

6-[3-(1-Amino-2-hydroxyethyl)pyrrolidin-1-yl]-4-cyclopropyl-7-fluoro-5-methoxypyrido[1,2-c]pyrimidine-1,3-dione;

6-[3-(1-Amino-2-hydroxyethyl)pyrrolidin-1-yl]-4-cyclopropyl-7-fluoro-5-methoxy-8-methylpyrido[1,2-c]pyrimidine-1,3-dione;

6-[3-(1-Amino-2-hydroxyethyl)pyrrolidin-1-yl]-4-cyclopropyl-7-fluoro-5,8-dimethylpyrido[1,2-c]pyrimidine-1,3-dione;

4-Cyclopropyl-7-fluoro-5-methoxy-6-(4-pyridin-4-ylthiophen-2-yl)pyrido[1,2-c]pyrimidine-1,3-dione; and 6-[4-(1-Aminoethyl)thiophen-2-yl]-4-cyclopropyl-7-fluoro-5-methoxypyrido[1,2-c]pyrimidine-1,3-dione; or a pharmaceutically acceptable salt thereof.

The invention also provides a pharmaceutical composition comprising a compound of one of the above-mentioned Formulas admixed with a carrier, diluent, or excipient.

The invention also provides a method of treating a bacterial infection in a mammal comprising administering to the mammal in need thereof an antibacterial effective amount of a compound of one of the above-mentioned Formulas.

The invention also provides a method of inhibiting a bacterial topoisomerase in a mammal comprising administering to the mammal in need thereof an effective amount of a compound of one of the above-mentioned Formulas.

The invention also provides a method of inhibiting a bacterial DNA gyrase in a mammal comprising administering to the mammal in need thereof an effective amount of a compound of one of the above-mentioned Formulas.

The invention also provides a method of inhibiting a bacterial topoisomerase IV in a mammal comprising administering to the mammal in need thereof an effective amount of a compound of one of the above-mentioned Formulas.

The invention also provides a method of inhibiting a quinolone-resistant bacteria in a mammal comprising administering to the mammal an effective amount of a compound of one of the above-mentioned Formulas.

The invention also provides a process for preparing a compound of Formula I wherein $R_2$ is H or $NH_2$ and $R_6$ is $C_1$–$C_7$ alkyl and substituted alkyl, comprising:

(a) reacting amide 2 with a carbon monoxide equivalent such as phosgene to form bicyclic compound 3;

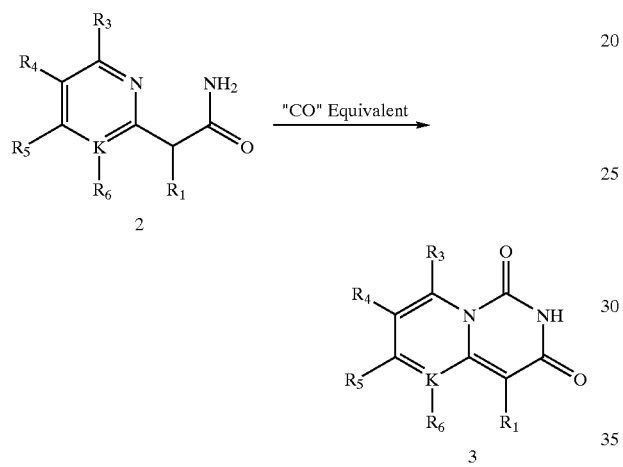

(b) coupling an amine to bicyclic compound 3 to form compound C1;

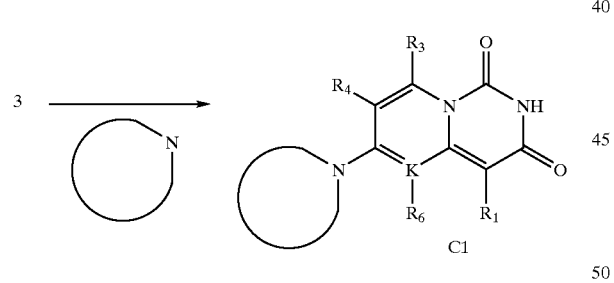

and optionally (c) aminating bicyclic compound 3 to form compound B1.

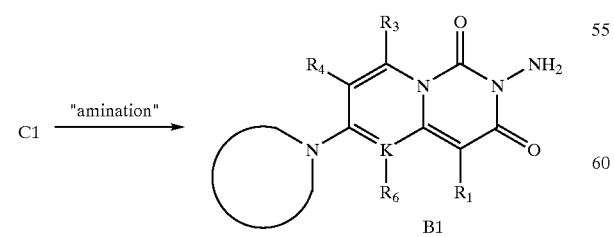

The invention also provides a process for preparing a compound of Formula I wherein $R_2$ is H or $NH_2$ and $R_6$ is $C_1$–$C_7$ alkoxy and substituted alkoxy, comprising:

(a) reacting substituted pyridine compound 6 with hydrazine to from hydrazine derivative 7;

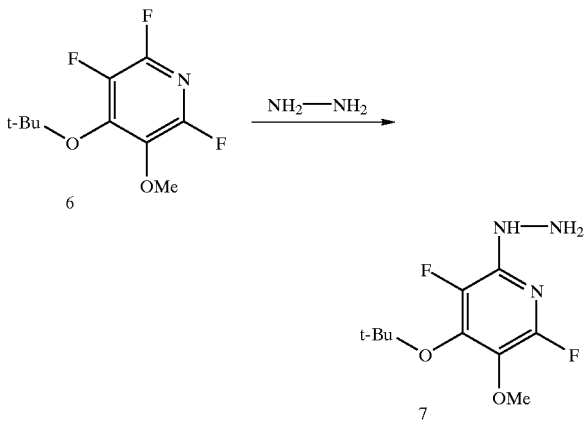

(b) reacting hydrazine derivative 7 with oxygen in the presence of base to form compound 8;

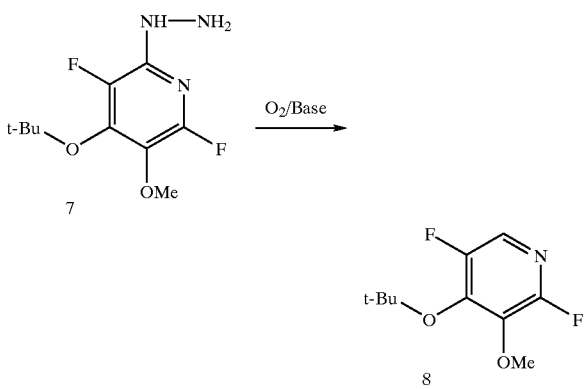

(c) reacting compound 8 with the anion of cyclopropyl acetonitrile to form compound 9;

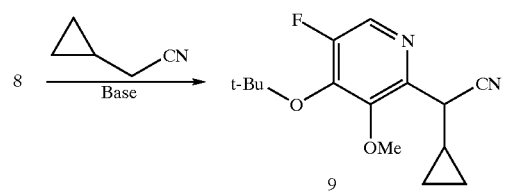

(d) converting the nitrile moiety in compound 10 to an amide and cyclizing according to step a in the previous process.

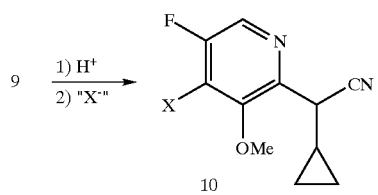

(e) converting the nitrile moiety in compound 10 to an amide and cyclizing as described for step (a) of the previous process.

DETAILED DESCRIPTION OF THE INVENTION

The following definitions are used, unless otherwise described: "Ph" is phenyl; halo is fluoro, chloro, bromo, or iodo. Alkyl, alkoxy, alkenyl, alkynyl, etc. denote both straight and branched groups; but reference to an individual radical such as "propyl" embraces only the straight chain radical, a branched chain isomer such as "isopropyl" being specifically referred to.

The term "alkyl" means a straight or branched hydrocarbon radical having from 1 to 7 carbon atoms and includes, for example, methyl, ethyl, n-propyl, isopropyl, n-butyl, sec-butyl, isobutyl, tert-butyl, n-pentyl, n-hexyl, n-heptyl, and the like.

The term "$C_2$–$C_7$ alkenyl" means a straight or branched hydrocarbon radical having from 1 to 3 double bonds. Examples include ethenyl, 2-propen-1-yl, 1,3-butadien-1-yl, 3-hexen-1-yl, 5-octen-2-yl, 2-isopropyl-3,5-octadien-1-yl, cis-3-hexen-1-yl, and trans-2-hepten-1-yl, and the like. Preferred alkenyl groups include $C_2$–$C_6$ alkenyls such as ethenyl, 2-propen-1-yl, 2-buten-1-yl, and 3-penten-1-yl, and the like.

The term "$C_2$–$C_7$ alkynyl" means a straight or branched hydrocarbon radical having from 1 to 3 triple-bonds. Examples include ethynyl, propynyl, 3-butyn-1-yl, 4-hexyn-1-yl, and 5-heptyn-3-yl, and the like. Preferred alkynyl groups are $C_2$–$C_6$ alkynyls such as ethynyl, propynyl, 3-butyn-1-yl, and 5-hexyn-1-yl, and the like.

The alkyl, alkenyl, and alkynyl groups can be substituted with one or more groups selected from halo, hydroxy, cyano, $C_1$–$C_6$ alkoxy, nitro, nitroso, amino, $C_1$–$C_6$ alkylamino, di-$C_1$–$C_6$ alkylamino, carboxy, $C_1$–$C_6$ alkoxycarbonyl, aminocarbonyl, halomethyl, dihalomethyl, trihalomethyl, haloethyl, dihaloethyl, trihaloethyl, tetrahaloethyl, pentahaloethyl, thiol, ($C_1$–$C_4$)alkylsulfanyl, ($C_1$–$C_4$) alkylsulfinyl, and aminosulfonyl, —NH—$SO_2$—$NH_2$, —O—$SO_2$—NH—,

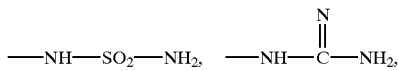

($C_1$–$C_6$)dialkylthio, —NH—$SO_2$—R, where R is ($C_1$–$C_6$) alkyl. Examples of substituted alkyl groups include fluoromethyl, difluoromethyl, trifluoromethyl, tribromomethyl, hydroxymethyl, 3-methoxypropyl, 3-carboxypentyl, 3,5-dibromo-6-aminocarbonyldecyl, and 4-ethylsulfinyloctyl. Examples of substituted alkenyl groups include 2-bromoethenyl, 1-amino-2-propen-1-yl, 3-hydroxypent-2-en-1-yl, 4-methoxycarbonyl-hex-2-en-1-yl, and 2-nitro-3-bromo-4-iodo-oct-5-en-1-yl. Typical substituted alkynyl groups include 2-hydroxyethynyl, 3-dimethylamino-hex-5-yn-1-yl, and 2-cyano-hept-3-yn-1-yl.

The term "cycloalkyl" means a hydrocarbon ring containing from 3 to 12 carbon atoms, for example, cyclopropyl, cyclobutyl, cyclopentyl, cyclohexyl, cycloheptyl, cyclooctyl, decalinyl, norpinanyl, and adamantyl. Where possible, the cycloalkyl group may contain double bonds, for example, 3-cyclohexen-1-yl. The cycloalkyl ring may be unsubstituted or substituted by one or more substituents selected from alkyl, alkoxy, thioalkoxy, hydroxy, thiol, nitro, halogen, amino, alkyl and dialkylamino, formyl, carboxyl, CN, —NH—CO—R, —CO—NHR, —$CO_2$R, —COR, wherein R is defined as above, aryl, heteroaryl, wherein alkyl, aryl, and heteroaryl are as defined herein, or as indicated above for alkyl, alkenyl, and alkynyl substitutents. Examples of substituted cycloalkyl groups include fluorocyclopropyl, 2-iodocyclobutyl, 2,3-dimethylcyclopentyl, 2,2-dimethoxycyclohexyl, and 3-phenylcyclopentyl.

The term "heterocyclic" means a monocyclic, fused, bridged, or spiro bicyclic heterocyclic ring systems. Monocyclic heterocyclic rings contain from about 3 to 12 ring atoms, with from 1 to 5 heteroatoms selected from N, O, and S, and preferably from 3 to 7 member atoms, in the ring. Bicyclic heterocyclics contain from about 5 to about 17 ring atoms, preferably from 5 to 12 ring atoms. Bicyclic heterocyclic rings may be fused, spiro, or bridged ring systems. Examples of heterocyclic groups include cyclic ethers (oxiranes) such as ethyleneoxide, tetrahydrofuran, dioxane, and substituted cyclic ethers, wherein the substituents are those described above for the alkyl and cycloalkyl groups. Typical substituted cyclic ethers include propyleneoxide, phenyloxirane (styrene oxide), cis-2-butene-oxide (2,3-dimethyloxirane), 3-chlorotetrahydrofuran, 2,6-dimethyl-1,4-dioxane, and the like. Heterocycles containing nitrogen are groups such as pyrrolidine, piperidine, piperazine, tetrahydrotriazine, tetrahydropyrazole, and substituted groups such as 3-aminopyrrolidine, 4-methylpiperazin-1-yl, and the like. Typical sulfur containing heterocycles include tetrahydrothiophene, dihydro-1,3-dithiol-2-yl, and hexahydrothiophen-4-yl and substituted groups such as aminomethyl thiophene. Other commonly employed heterocycles include dihydro-oxathiol-4-yl, dihydro-1H-isoindole, tetrahydro-oxazolyl, tetrahydro-oxadiazolyl, tetrahydrodioxazolyl, tetrahydrooxathiazolyl, hexahydrotriazinyl, tetrahydro-oxazinyl, morpholinyl, thiomorpholinyl, tetrahydropyrimidinyl, dioxolinyl, octahydrobenzofuranyl, octahydrobenzimidazolyl, and octahydrobenzothiazolyl. For heterocycles containing sulfur, the oxidized sulfur heterocycles containing SO or $SO_2$ groups are also included. Examples include the sulfoxide and sulfone forms of tetrahydrothiophene.

The term "aryl" means a cyclic or polycyclic aromatic ring having from 5 to 12 carbon atoms, and being unsubstituted or substituted with one or more of the substituent groups recited above for alkyl, alkenyl, and alkynyl groups. Examples of aryl groups include phenyl, 2,6-dichlorophenyl, 3-methoxyphenyl, naphthyl, 4-thionaphthyl, tetralinyl, anthracinyl, phenanthrenyl, benzonaphthenyl, fluorenyl, 2-acetamidofluoren-9-yl, and 4'-bromobiphenyl.

The term "heteroaryl" means an aromatic cyclic or polycyclic ring system having from 1 to 4 heteroatoms selected from N, O, and S. Typical heteroaryl groups include 2- or 3-thienyl, 2- or 3-furanyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2-, 3-, or 4-pyridinyl, 3-, 4-, or 5-pyridazinyl, 2-pyrazinyl, 2-, 4-, or 5-pyrimidinyl, 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, 2-, 4-, 5-, 6-, or 7-benzoazolyl, 2-, 4-, 5-, 6-, or 7-benzimidazolyl, 2-, 4-, 5-, 6-, or 7-benzothiazolyl. The heteroaryl groups may be unsubstituted or substituted by 1 to 3 substituents selected from those described above for alkyl, alkenyl, and alkynyl, for example, cyanothienyl and formylpyrrolyl.

Preferred aromatic fused heterocyclic rings of from 8 to 10 atoms include but are not limited to 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b] thienyl, 2-, 4-, 5-, 6-, or 7-benzoxazolyl, 2-, 4-, 5-, 6-, or 7-benzimidazolyl, 2-, 4-, 5-, 6-, or 7-benzothiazolyl. Heteroaryl also includes 2- and 3-aminomethylfuran, 2- and 3-aminomethylthiophene and the like.

It will be appreciated by those skilled in the art that compounds of the invention having one or more chiral centers may exist in and be isolated in optically active and racemic forms. Some compounds may exhibit polymorphism. It is to be understood that the present invention encompasses any racemic, optically-active, polymorphic, geometric, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine activity or cytotoxicity using the standard tests described herein, or using other similar tests which are well known in the art.

A "prodrug" is an inactive derivative of a drug molecule that requires a chemical or an enzymatic biotransformation in order to release the active parent drug in the body.

Specific and preferred values for compounds of Formula I are listed below for radicals, substituents, and ranges are for illustration purposes only, and they do not exclude other defined values or other values within defined ranges for the radicals and substituents.

A specific value for J is C. Another specific value for J is N.

A specific value for K is C. Another specific value for K is N.

A specific value for $R_1$ is methyl. Another specific value for $R_1$ is ethyl, isopropyl, cyclopropyl, t-butyl, 2-fluorocyclopropyl, 1- or 2-methylcyclopropyl, cyclopropylmethyl, vinyl, phenyl or substituted phenyl, heteroaryl or substituted heteroaryl.

A specific value for $R_2$ is H. Another specific value for $R_2$ is OH. Another specific value for $R_2$ is $NH_2$. Another specific value for $R_2$ is $C_1-C_7$ alkyl and substituted alkyl, $C_2-C_7$ alkenyl and substituted alkenyl, $C_2-C_7$ alkynyl and substituted alkynyl, $C_3-C_7$ cycloalkyl and substituted cycloalkyl, aryl and substituted aryl, heterocyclic and substituted heterocyclic, heteroaryl and substituted heteroaryl, halo, $NO_2$, NO, CN, $OR_a$, $—CO_2R_a$, wherein $R_a$ is H, $C_1-C_7$ alkyl and substituted alkyl, $C_1-C_7$ alkenyl and substituted alkenyl, $C_3-C_7$ cycloalkyl and substituted cycloalkyl, aryl and substituted aryl, heteroaryl and substituted heteroaryl, heterocycloalkyl and substituted heterocycloalkyl; $—CO_2R_b$,

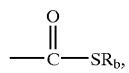

O=C—$SR_b$, —$COR_b$, wherein $R_b$ is H, $C_1-C_7$ alkyl and substituted alkyl, $C_1-C_7$ alkenyl and substituted alkenyl, $C_3-C_7$ cycloalkyl and substituted cycloalkyl, aryl and substituted aryl, heteroaryl and substituted heteroaryl, heterocycloalkyl and substituted heterocycloalkyl; —$CO_2NR_cR_d$, wherein $R_d$ and $R_d$ are independently H, $C_1-C_7$ alkyl and substituted alkyl, $C_1-C_7$ alkenyl and substituted alkenyl, $C_3-C_7$ cycloalkyl and substituted cycloalkyl, aryl and substituted aryl, heteroaryl and substituted heteroaryl, heterocycloalkyl and substituted heterocycloalkyl; $NR_eR_f$, wherein $R_d$ and $R_f$ are each independently H, $C_1-C_7$ alkyl and substituted alkyl, $C_3-C_7$ cycloalkyl and substituted cycloalkyl, aryl and substituted aryl, or —$CO_2R_b$,

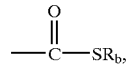

—$COR_b$, wherein $R_b$ is defined as above; —$CONR_cR_d$, wherein $R_c$ and $R_d$ are defined as above; aryl and substituted aryl, heteroaryl and substituted heteroaryl, heterocycloalkyl and substituted heterocycloalkyl, or $R_e$ and $R_f$ are taken together with the nitrogen to which they are attached to form a 3 to 7 membered ring, said ring being substituted or unsubstituted with 1, 2, 3, or 4 substituent groups.

A specific value for each of $R_3$, $R_4$, and $R_6$ is H, OH, $(O)_nC_1-C_7$ alkyl and substituted alkyl, $(O)_nC_2-C_7$ alkenyl and substituted alkenyl, $(O)_nC_2-C_7$ alkynyl and substituted alkynyl, wherein n is 0 or 1; halo, $NO_2$, CN, $NR_gR_h$, wherein $R_g$ and $R_h$ independently are H, $C_1-C_7$ alkyl and substituted alkyl, $C_2-C_7$ alkenyl and substituted alkenyl, $C_2-C_7$ alkynyl and substituted alkynyl, —CO—$C_1-C_7$ alkyl and substituted alkyl, or $R_g$ and $R_h$ taken together with the nitrogen to which they are attached form a 3- to 7-membered ring containing from 1 to 3 heteroatoms selected from N, O, and S, said ring being unsubstituted or substituted with 1, 2, 3, or 4 substituent groups.

A specific value for $R_5$ is $C_1-C_7$ alkyl and substituted alkyl, $C_2-C_7$ alkenyl and substituted alkenyl, $C_2-C_7$ alkynyl and substituted alkynyl, —$CO_2R_a$, wherein $R_a$ is defined as above, —$CO_2R_b$,

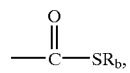

—$COR_b$, wherein $R_b$ is defined as above, —$CONR_cR_d$, wherein $R_c$ and $R_d$ are defined as above; halo, $NO_2$, CN, $NR_iR_j$, wherein $R_i$ and $R_j$ independently are H, $C_1-C_7$ alkyl and substituted alkyl, $C_2-C_7$ alkenyl and substituted alkenyl, $C_2-C_7$ alkynyl and substituted alkynyl, CO—$C_1-C_7$ alkyl and substituted alkyl, or $R_i$ and $R_j$ taken together with the nitrogen to which they are attached form a 3- to 7-membered ring containing from 1 to 3 heteroatoms selected from N, O, and S, said ring being unsubstituted or substituted with 1, 2, 3, or 4 substituent groups; aryl, fused aryl, heterocyclic, fused heterocyclic, bicyclic heterocyclic, or spiro heterocyclic, wherein fused aryl, fused heterocyclic, bicyclic heterocyclic, or spiro heterocyclic can be substituted.

Further examples of typical heterocycles, fused bicyclic or spiro heterocycles, and heteroaryl groups that are specific values for $R_5$ are listed below in Table 1. In Table 1, "〰" indicates the point of attachment.

TABLE 1

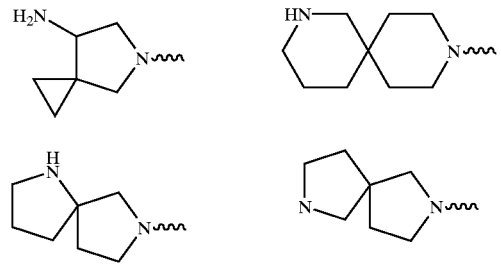

TABLE 1-continued
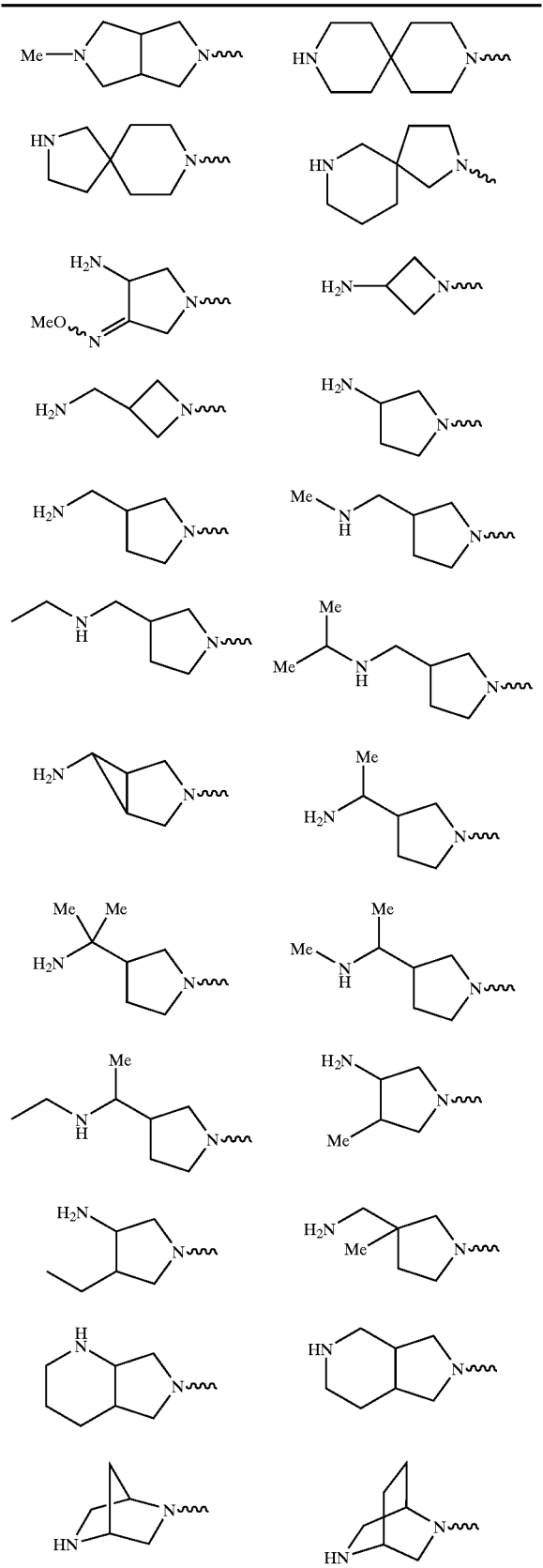
TABLE 1-continued
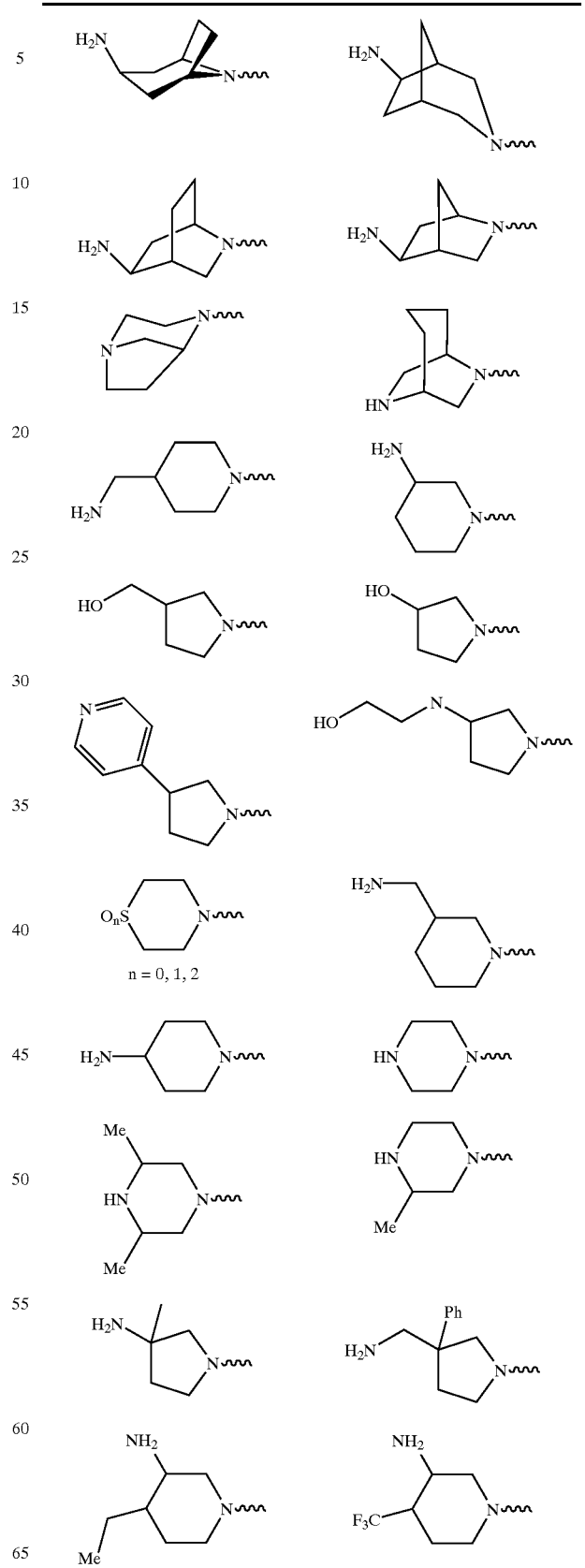

TABLE 1-continued
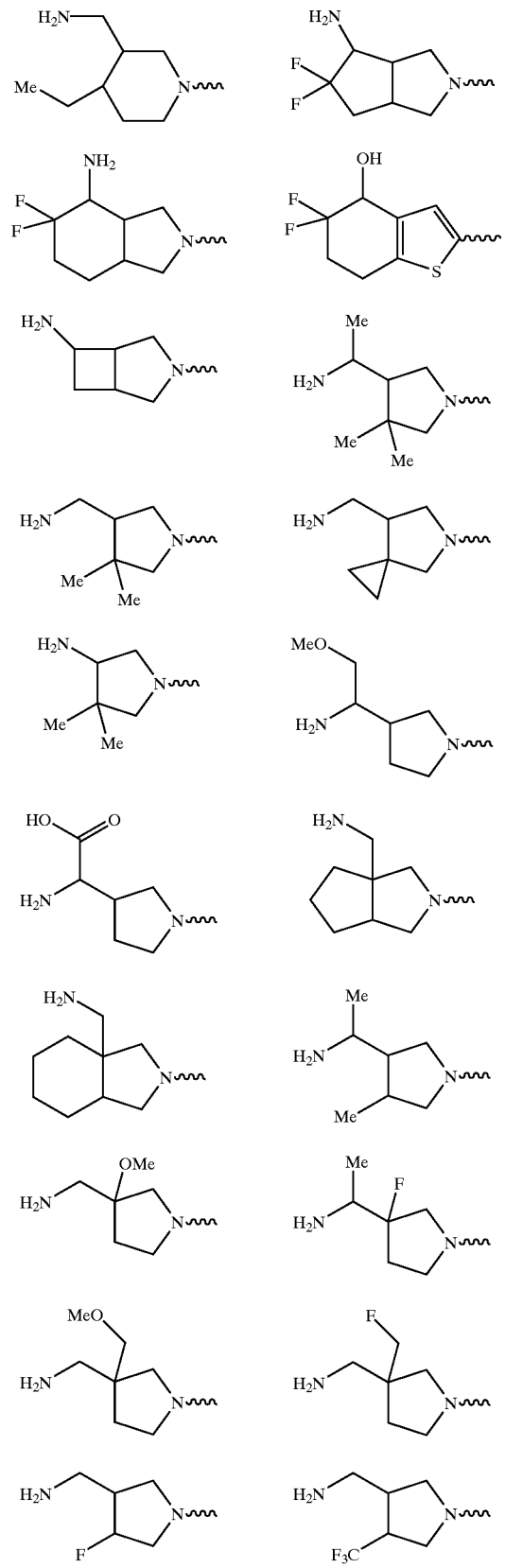
TABLE 1-continued
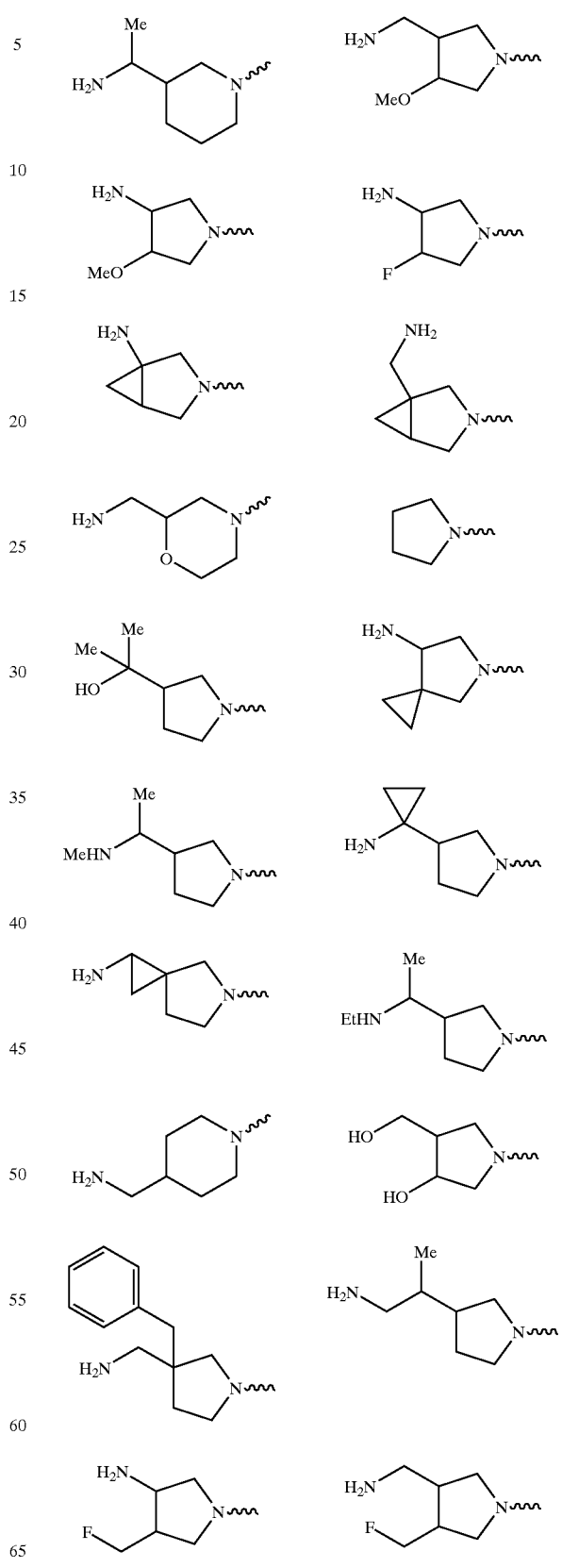

TABLE 1-continued
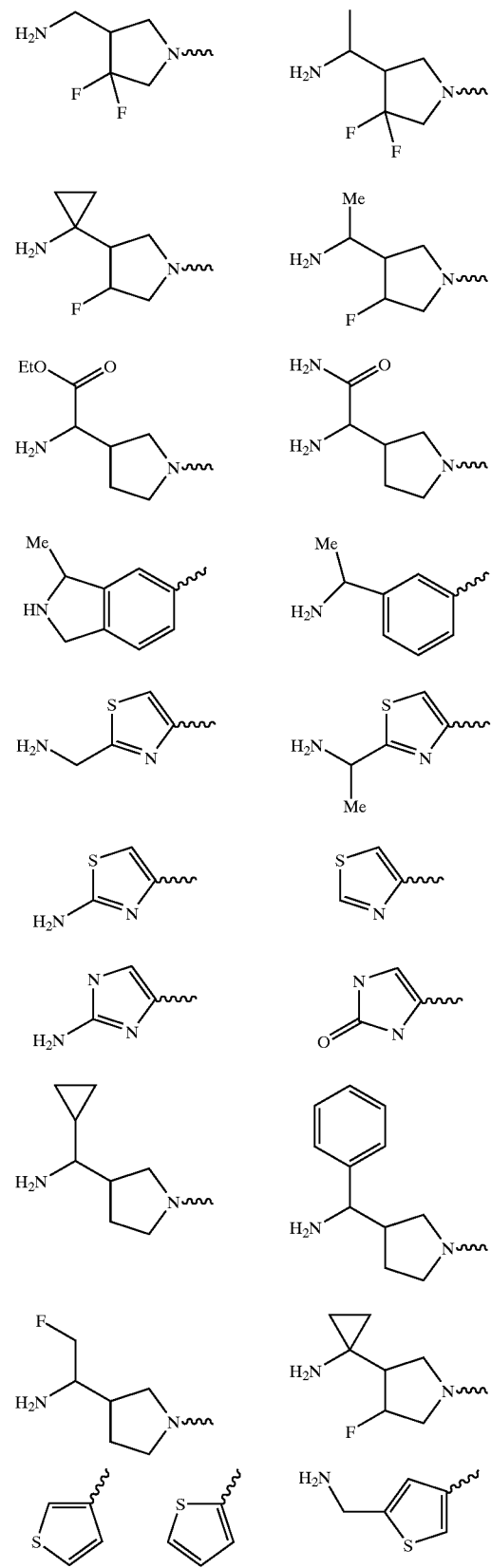
TABLE 1-continued
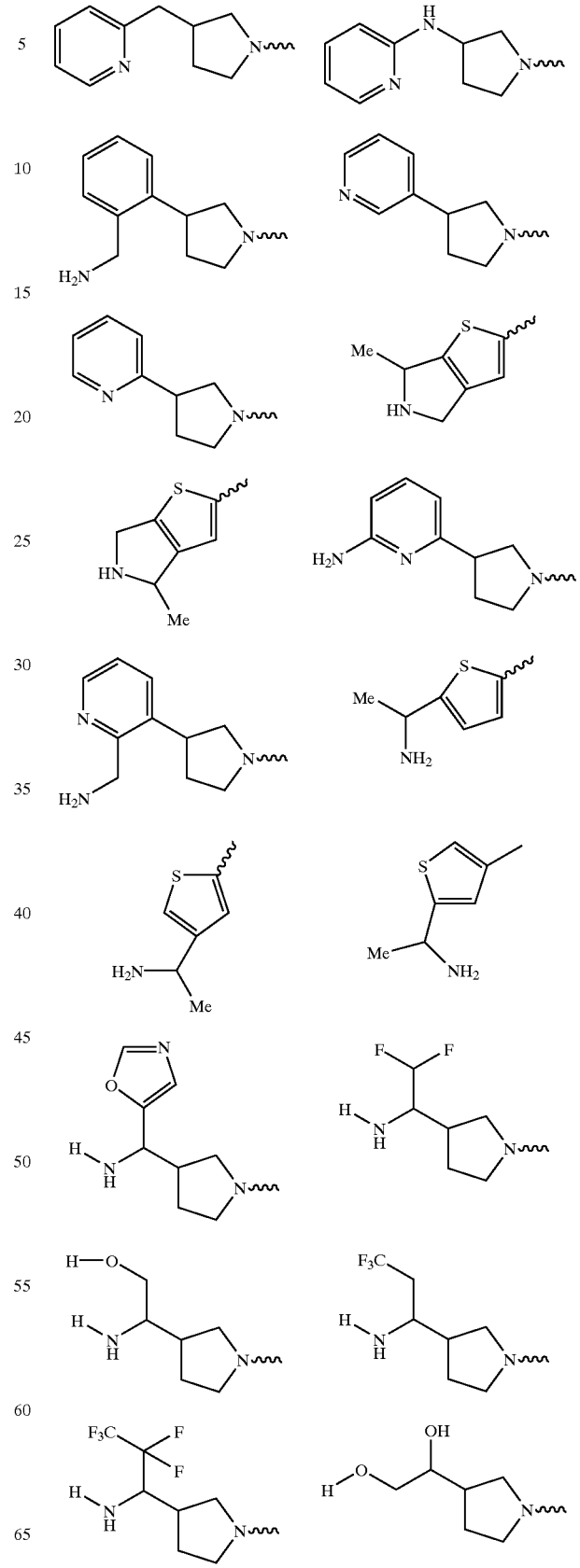

TABLE 1-continued

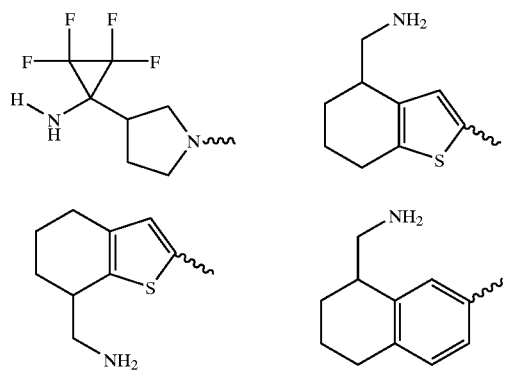

In compounds of Formula 1, a preferred value for J is C. Another preferred value for J is N. A preferred value for K is C. Another preferred value for K is N. A preferred value for $R_1$ is cyclopropyl. Another preferred value for $R_1$ is 2-fluorocyclopropyl, 1- or 2-methylcyclopropyl, or cyclopropylmethyl. A preferred value for $R_2$ is $NH_2$. Another preferred value for $R_2$ is H. Another preferred value for $R_2$ is H. A preferred value for $R_3$ is H. Another preferred value for $R_3$ is methyl. Another preferred value for $R_3$ is methoxy. Another preferred value for $R_3$ is $NH_2$. A preferred value for $R_4$ when J is C is F. Another preferred value for $R_4$ when J is C is Cl. A preferred value for $R_5$ is 1-pyrrolidinyl or substituted 1-pyrrolidinyl. Another preferred value for $R_5$ is 1-piperidinyl or substituted 1-piperidinyl, or 1-piperizinyl or substituted 1-piperizinyl. Other preferred values for $R_5$ include heterocycles and heteroaryl groups such as those known in the quinolone art, for instance, as found in *J. Med. Chem.*, 1992;35:1764; *J. Med. Chem.*, 1996;39:3070; *Synlett.*,1996:1097; and *J. Med. Chem.*, 1986;29:445. A preferred value for $R_6$ when K is C is H. Another preferred value for $R_6$ when K is C is $C_1$–$C_4$ alkyl and substituted alkyl, halo, OH, or —O—$C_1$–$C_4$ alkyl and substituted —O—$C_1$–$C_4$ alkyl, $OCF_3$, $OCHF_2$, $OCH_2F$, $OCH_2CF_3$, $OCH_2CHF_2$, or $OCH_2CH_2F$.

A preferred group of compounds of Formula I are compounds wherein J and K are C; $R_1$ is methyl, ethyl, cyclopropyl, t-butyl, 2-fluorocyclopropyl; $R_2$ is H, OH, or $NH_2$; $R_3$ is H; $R_4$ is F or Cl; $R_5$ is 1-pyrrolidinyl or substituted 1-pyrrolidinyl, 1-piperidinyl or substituted 1-piperidinyl, 1-piperizinyl or substituted 1-piperizinyl or

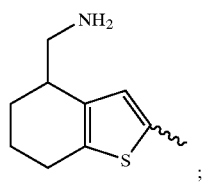
;

and $R_6$ is F, Cl, methyl, methoxy, $OCF_3$, $OCHF_2$, $OCH_2F$, $OCH_2CF_3$, $OCH_2CHF_2$, or $OCH_2CH_2F$.

Another preferred group of compounds of Formula I are compounds wherein J is N, K is C; $R_1$ is cyclopropyl; $R_2$ is H or $NH_2$; $R_3$ is H; $R_5$ is 1-pyrrolidinyl or substituted 1-pyrrolidinyl, 1-piperidinyl or substituted 1-piperidinyl, 1-piperizinyl or substituted 1-piperizinyl; and $R_6$ is methyl, methoxy, $OCF_3$, $OCHF_2$, $OCH_2F$, $OCH_2CF_3$, $OCH_2CHF_2$, or $OCH_2CH_2F$.

Another preferred group of compounds of Formula I are compounds wherein J is C; K is N; $R_1$ is cyclopropyl; $R_2$ is H or $NH_2$; $R_3$ is H; $R_4$ is F or Cl; and $R_5$ is 1-pyrrolidinyl or substituted 1-pyrrolidinyl, 1-piperidinyl or substituted 1-piperidinyl, 1-piperizinyl or substituted 1-piperizinyl.

Another preferred group of compounds of Formula I are compounds wherein J is N; K is N; $R_1$ is cyclopropyl; $R_2$ is H or $NH_2$; $R_3$ is H; and $R_5$ is 1-pyrrolidinyl or substituted 1-pyrrolidinyl, 1-piperidinyl or substituted 1-piperidinyl, 1-piperizinyl or substituted 1-piperizinyl.

Representative compounds of the invention which are compounds of Formula 1 are shown below in Table 2-I.

TABLE 2-I

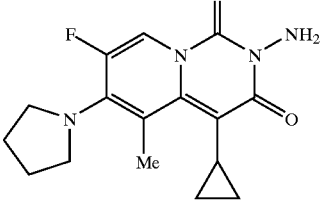

Example 4g

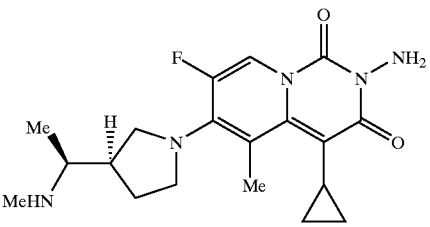

Example 4f

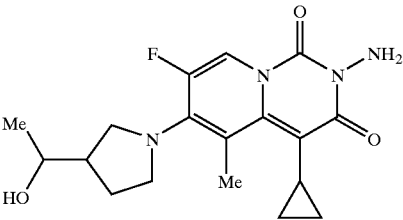

Example 4h

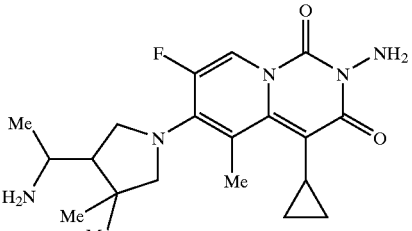

Example 5c

Representative compounds of the present invention, which are encompassed by Formula I include, but are not limited to the compounds in Table 2-I and their pharmaceutically acceptable acid or base addition salts, or amide or prodrugs thereof.

In compounds of Formula II, a preferred value for $R_1$ is cyclopropyl. Another preferred value for $R_1$ is 2-fluorocyclopropyl, 1- or 2-methylcyclopropyl, or cyclopropylmethyl. A preferred value for $R_2$ is $NH_2$. Another preferred value for $R_2$ is H. Another preferred value for $R_2$ is OH. A preferred value for $R_3$ is H. Another preferred value for $R_3$ is methyl. Another preferred value for $R_3$ is methoxy. Another preferred value for $R_3$ is $NH_2$. A preferred value for $R_4$ is F Another preferred value for $R_4$ is Cl. A preferred value for $R_5$ is 1-pyrrolidinyl or substituted 1-pyrrolidinyl. Another preferred value for $R_5$ is 1-piperidinyl or substituted 1-piperidinyl, or 1-piperizinyl or substituted 1-piperizinyl. Other preferred values for $R_5$ include heterocycles and heteroaryl groups such as those known in the quinolone art, for instance, as described above for compounds of Formula I. A preferred value for $R_6$ is H. Another preferred value for $R_6$ is $C_1$-$C_4$ alkyl and substituted alkyl, halo, OH, or —O—$C_1$-$C_4$ alkyl and substituted —O—$C_1$-$C_4$ alkyl, $OCF_3$, $OCHF_2$, $OCH_2F$, $OCH_2CF_3$, $OCH_2CHF_2$, or $OCH_2CH_2F$.

A preferred group of compounds of Formula II are compounds wherein $R_1$ is cyclopropyl; $R_2$ is H, OH or $NH_2$; $R_3$ is H; $R_4$ is F or Cl; $R_5$ is 1-pyrrolidinyl or substituted 1-pyrrolidinyl, 1-piperidinyl or substituted 1-piperidinyl, 1-piperizinyl or substituted 1-piperizinyl; and $R_6$ is F, Cl, methyl, methoxy, $OCF_3$, $OCHF_2$, $OCH_2F$, $OCH_2CF_3$, $OCH_2CHF_2$, or $OCH_2CH_2F$.

Another preferred group of compounds of Formula II are compounds wherein $R_1$ is cyclopropyl; $R_2$ is H or $NH_2$; $R_3$ is H; $R_4$ is F; $R_5$ is 1-pyrrolidinyl or substituted 1-pyrrolidinyl, 1-piperidinyl or substituted 1-piperidinyl; and $R_6$ is methyl, methoxy, $OCF_3$, $OCHF_2$, $OCH_2F$, $OCH_2CF_3$, $OCH_2CHF_2$, or $OCH_2CH_2F$.

Another preferred group of compounds of Formula II are compounds wherein $R_1$ is cyclopropyl; $R_2$ is H or $NH_2$; $R_3$ is H; $R_4$ is F; $R_5$ is 1-pyrrolidinyl or substituted 1-pyrrolidinyl, or 1-piperidinyl or substituted 1-piperidinyl; and $R_6$ is methyl, methoxy, $OCF_3$, $OCHF_2$, $OCH_2F$, $OCH_2CF_3$, or $OCH_2CHF_2$.

Another preferred group of compounds of Formula II are compounds wherein $R_1$ is cyclopropyl; $R_2$ is H or $NH_2$; $R_3$ is H; $R_4$ is F; $R_5$ is 1-pyrrolidinyl or substituted 1-pyrrolidinyl, 1-piperidinyl or substituted 1-piperidinyl, 1-piperizinyl or substituted 1-piperizinyl; and $R_6$ is methyl, methoxy, $OCF_3$, $OCHF_2$, $OCH_2F$, or $OCH_2CF_3$.

Representative compounds of the invention which are compounds of Formula 1 are also shown in Table 2-I.

In compounds of Formula III, a preferred value for $R_1$ is cyclopropyl. Another preferred value for $R_1$ is 2-fluorocyclopropyl, 1- or 2-methylcyclopropyl, or cyclopropylmethyl. A preferred value for $R_2$ is $NH_2$. Another preferred value for $R_2$ is H. Another preferred value for $R_2$ is OH. A preferred value for $R_4$ is F. Another preferred value for $R_4$ is Cl. A preferred value for $R_5$ is 1-pyrrolidinyl or substituted 1-pyrrolidinyl. Another preferred value for $R_5$ is 1-piperidinyl or substituted 1-piperidinyl, or 1-piperizinyl or substituted 1-piperizinyl. Other preferred values for $R_5$ include heterocycles and heteroaryl groups such as those known in the quinolone art, for instance, as described above for compounds of Formula I.

A preferred group of compounds of Formula III are compounds wherein $R_1$ is cyclopropyl; $R_2$ is H, OH, or $NH_2$; $R_3$ is H; $R_4$ is F or Cl; and $R_5$ is 1-pyrrolidinyl or substituted 1-pyrrolidinyl, 1-piperidinyl or substituted 1-piperidinyl, 1-piperizinyl or substituted 1-piperizinyl.

Another preferred group of compounds of Formula III are compounds wherein $R_1$ is cyclopropyl; $R_2$ is H OH, or $NH_2$; $R_3$ is H; $R_4$ is F; and $R_5$ is 1-pyrrolidinyl or substituted 1-pyrrolidinyl, 1-piperidinyl or substituted 1-piperidinyl, 1-piperizinyl or substituted 1-piperizinyl.

Another preferred group of compounds of Formula III are compounds wherein $R_1$ is cyclopropyl; $R_2$ is H or $NH_2$; $R_3$ is H; $R_4$ is F; and $R_5$ is 1-pyrrolidinyl or substituted 1-pyrrolidinyl, or 1-piperidinyl or substituted 1-piperidinyl.

Another preferred group of compounds of Formula III are compounds wherein $R_1$ is cyclopropyl; $R_2$ is H or $NH_2$; $R_3$ is H; $R_4$ is F; and $R_5$ is 1-pyrrolidinyl or substituted 1-pyrrolidinyl.

Representative compounds of the invention which are compounds of Formula III are shown below in Table 2-III.

TABLE 2-III

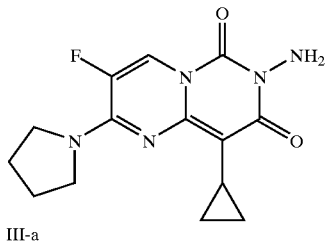

III-a

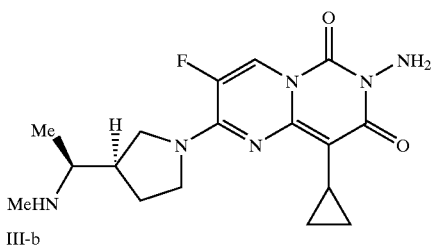

III-b

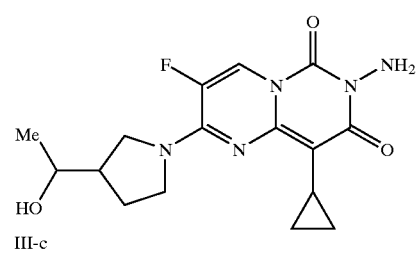

III-c

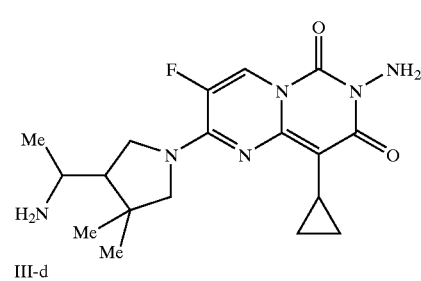

III-d

Representative compounds of the present invention, which are encompassed by Formula III include, but are not limited to the compounds in Table 2-III and their pharmaceutically acceptable acid or base addition salts, or amide or prodrugs thereof.

In compounds of Formula IV, a preferred value for $R_1$ is cyclopropyl. Another preferred value for $R_1$ is 2-fluorocyclopropyl, 1- or 2-methylcyclopropyl, or cyclopropylmethyl. A preferred value for $R_2$ is $NH_2$. Another preferred value for $R_2$ is H. Another preferred value for $R_2$ is OH. A preferred value for $R_5$ is 1-pyrrolidinyl or substituted 1-pyrrolidinyl. Another preferred value for $R_5$ is 1-piperidinyl or substituted 1-piperidinyl, or 1-piperizinyl or substituted 1-piperizinyl. Other preferred values for $R_5$ include heterocycles and heteroaryl groups such as those known in the quinolone art, for instance, as described above for compounds of Formula I. A preferred value for $R_6$ is H.

Another preferred value for $R_6$ is $C_1$–$C_4$ alkyl and substituted alkyl, halo, OH, or —O—$C_1$–$C_4$ alkyl and substituted —O—$C_1$–$C_4$ alkyl, $OCF_3$, $OCHF_2$, $OCH_2F$, $OCH_2CF_3$, $OCH_2CHF_2$, or $OCH_2CH_2F$.

A preferred group of compounds of Formula IV are compounds wherein $R_1$ is cyclopropyl; $R_2$ is H, OH, or $NH_2$; $R_5$ is 1-pyrrolidinyl or substituted 1-pyrrolidinyl, 1-piperidinyl or substituted 1-piperidinyl, 1-piperizinyl or substituted 1-piperizinyl; and $R_6$ is F, Cl, methyl, methoxy, $OCF_3$, $OCHF_2$, $OCH_2F$, $OCH_2CF_3$, $OCH_2CHF_2$, or $OCH_2CH_2F$.

Another preferred group of compounds of Formula IV are compounds wherein $R_1$ is cyclopropyl; $R_2$ is H or $NH_2$; $R_5$ is 1-pyrrolidinyl or substituted 1-pyrrolidinyl, 1-piperidinyl or substituted 1-piperidinyl, 1-piperizinyl or substituted 1-piperizinyl; and $R_6$ is methyl, methoxy, $OCF_3$, $OCHF_2$, $OCH_2F$, $OCH_2CF_3$, $OCH_2CHF_2$, or $OCH_2CH_2F$.

Another preferred group of compounds of Formula IV are compounds wherein $R_1$ is cyclopropyl; $R_2$ is H, OH, or $NH_2$; and $R_5$ is 1-pyrrolidinyl or substituted 1-pyrrolidinyl, or 1-piperidinyl or substituted 1-piperidinyl; and $R_6$ is methyl, methoxy, $OCF_3$, $OCHF_2$, $OCH_2F$, $OCH_2CF_3$, $OCH_2CHF_2$, or $OCH_2CH_2F$.

Another preferred group of compounds of Formula IV are compounds wherein $R_1$ is cyclopropyl; $R_2$ is H or $NH_2$; $R_5$ is 1-pyrrolidinyl or substituted 1-pyrrolidinyl, or 1-piperidinyl or substituted 1-piperidinyl and $R_6$ is methyl, methoxy, $OCF_3$, $OCHF_2$, $OCH_2F$, or $OCH_2CF_3$.

Representative compounds of the invention which are compounds of Formula 1 are shown below in Table 2-IV.

TABLE 2-IV

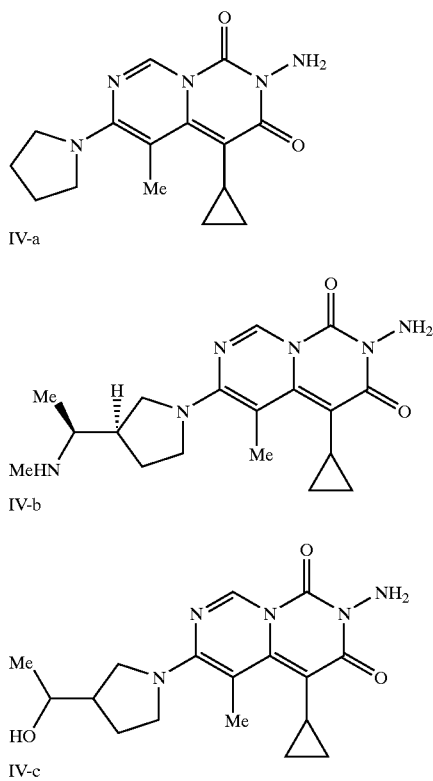

TABLE 2-IV-continued

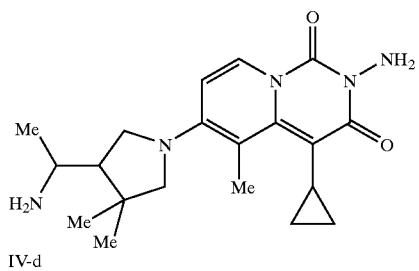

Representative compounds of the present invention, which are encompassed by Formula IV include, but are not limited to the compounds in Table 2-IV and their pharmaceutically acceptable acid or base addition salts, or amide or prodrugs thereof.

In compounds of Formula V, a preferred value for $R_1$ is cyclopropyl. Another preferred value for $R_1$ is 2-fluorocyclopropyl, 1- or 2-methylcyclopropyl, or cyclopropylmethyl. A preferred value for $R_2$ is $NH_2$. Another preferred value for $R_2$ is H. Another preferred value for $R_2$ is OH. A preferred value for $R_5$ is 1-pyrrolidinyl or substituted 1-pyrrolidinyl. Another preferred value for $R_5$ is 1-piperidinyl or substituted 1-piperidinyl, or 1-piperizinyl or substituted 1-piperizinyl. Other preferred values for $R_5$ include heterocycles and heteroaryl groups such as those known in the quinolone art, for instance, as described above for compounds of Formula I.

A preferred group of compounds of Formula V are compounds wherein $R_1$ is cyclopropyl; $R_2$ is H, OH, or $NH_2$; and $R_5$ is 1-pyrrolidinyl or substituted 1-pyrrolidinyl, 1-piperidinyl or substituted 1-piperidinyl, 1-piperizinyl or substituted 1-piperizinyl.

Another preferred group of compounds of Formula V are compounds wherein $R_1$ is cyclopropyl; $R_2$ is H or $NH_2$; and $R_5$ is 1-pyrrolidinyl or substituted 1-pyrrolidinyl, or 1-piperidinyl or substituted 1-piperidinyl.

Another preferred group of compounds of Formula V are compounds wherein $R_1$ is cyclopropyl; $R_2$ is H or $NH_2$; and $R_5$ is 1-pyrrolidinyl or substituted 1-pyrrolidinyl.

Another preferred group of compounds of Formula V are compounds wherein $R_1$ is cyclopropyl; $R_2$ is H or $NH_2$; and $R_5$ is substituted 1-pyrrolidinyl.

Representative compounds of the invention which are compounds of Formula V are shown below in Table 2-V.

TABLE 2-V

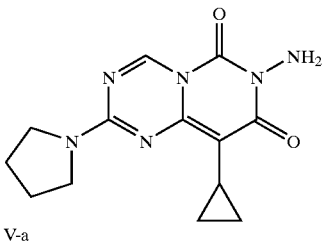

TABLE 2-V-continued

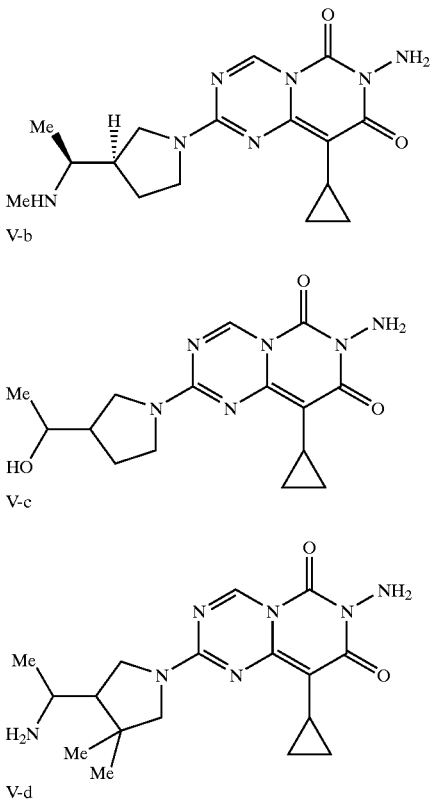

V-b

V-c

V-d

Representative compounds of the present invention, which are encompassed by Formula IV include, but are not limited to the compounds in Table 2-V and their pharmaceutically acceptable acid or base addition salts, or amide or prodrugs thereof.

In compounds of Formula VI, a preferred value for $R_1$ is cyclopropyl. Another preferred value for $R_1$ is 2-fluorocyclopropyl, 1- or 2-methylcyclopropyl, or cyclopropylmethyl. A preferred value for $R_2$ is $NH_2$. Another preferred value for $R_2$ is H. Another preferred value for $R_2$ is OH. A preferred value for $R_3$ is H. Another preferred value for $R_3$ is methyl. Another preferred value for $R_3$ is methoxy. Another preferred value for $R_3$ is $NH_2$. A preferred value for $R_4$ is F. Another preferred value for $R_4$ is Cl. A preferred value for $R_g$ and $R_h$, together with the nitrogen to which they are attached, is 1-pyrrolidinyl or substituted 1-pyrrolidinyl. Another preferred value for $R_g$ and $R_h$, together with the nitrogen to which they are attached, is 1-piperidinyl or substituted 1-piperidinyl, or 1-piperizinyl or substituted 1-piperizinyl. Other preferred values for $R_g$ and $R_h$, together with the nitrogen to which they are attached, include heterocycles and heteroaryl groups such as those known in the quinolone art, for instance, as described above for compounds of Formula I. A preferred value for $R_6$ is H. Another preferred value for $R_6$ is $C_1$–$C_4$ alkyl and substituted alkyl, halo, OH, or —O—$C_1$–$C_4$ alkyl and substituted —O—$C_1$–$C_4$ alkyl, $OCF_3$, $OCHF_2$, $OCH_2F$, $OCH_2CF_3$, $OCH_2CHF_2$, or $OCH_2CH_2F$.

A preferred group of compounds of Formula VI are compounds wherein $R_1$ is cyclopropyl; $R_2$ is H, OH, or $NH_2$; $R_3$ is H; $R_4$ is F or Cl; $R_g$ and $R_h$, together with the nitrogen to which they are attached, are 1-pyrrolidinyl or substituted 1-pyrrolidinyl, 1-piperidinyl or substituted 1-piperidinyl, 1-piperizinyl or substituted 1-piperizinyl; and $R_6$ is F, Cl, methyl, methoxy, $OCF_3$, $OCHF_2$, $OCH_2F$, $OCH_2CF_3$, $OCH_2CHF_2$, or $OCH_2CH_2F$.

Another preferred group of compounds of Formula VI are compounds wherein $R_1$ is cyclopropyl; $R_2$ is H or $NH_2$; $R_3$ is H; $R_4$ is F; $R_g$ and $R_h$, together with the nitrogen to which they are attached, are 1-pyrrolidinyl or substituted 1-pyrrolidinyl, 1-piperidinyl or substituted 1-piperidinyl, 1-piperizinyl or substituted 1-piperizinyl; and $R_6$ is methyl, methoxy, $OCF_3$, $OCHF_2$, $OCH_2F$, $OCH_2CF_3$, $OCH_2CHF_2$, or $OCH_2CH_2F$.

Another preferred group of compounds of Formula VI are compounds wherein $R_1$ is cyclopropyl; $R_2$ is H or $NH_2$; $R_3$ is H; $R_4$ is F; $R_g$ and $R_h$, together with the nitrogen to which they are attached, are 1-pyrrolidinyl or substituted 1-pyrrolidinyl, or 1-piperidinyl or substituted 1-piperidinyl; and $R_6$ is methyl, methoxy, $OCF_3$, $OCHF_2$, $OCH_2F$, $OCH_2CF_3$, $OCH_2CHF_2$, or $OCH_2CH_2F$.

Another preferred group of compounds of Formula VI are compounds wherein $R_1$ is cyclopropyl; $R_2$ is H or $NH_2$; $R_3$ is H; $R_4$ is F; $R_g$ and $R_h$, together with the nitrogen to which they are attached, are 1-pyrrolidinyl or substituted 1-pyrrolidinyl, or 1-piperidinyl or substituted 1-piperidinyl; and $R_6$ is methyl, methoxy, $OCF_3$, $OCHF_2$, $OCH_2F$, $OCH_2CF_3$, or $OCH_2CHF_2$.

Representative compounds of the invention which are compounds of Formula VI are shown in Table 2-I.

In compounds of Formula VII, a preferred value for $R_1$ is cyclopropyl. Another preferred value for $R_1$ is 2-fluorocyclopropyl, 1- or 2-methylcyclopropyl, or cyclopropylmethyl. A preferred value for $R_2$ is $NH_2$. Another preferred value for $R_2$ is H. Another preferred value for $R_2$ is OH. A preferred value for $R_3$ is H. Another preferred value for $R_3$ is methyl. Another preferred value for $R_3$ is methoxy. Another preferred value for $R_3$ is $NH_2$. A preferred value for $R_4$ is F Another preferred value for $R_4$ is Cl. A preferred value for $R_g$ and $R_h$, together with the nitrogen to which they are attached, is 1-pyrrolidinyl or substituted 1-pyrrolidinyl. Another preferred value for $R_g$ and $R_h$, together with the nitrogen to which they are attached, is 1-piperidinyl or substituted 1-piperidinyl, or 1-piperizinyl or substituted 1-piperizinyl. Other preferred values for $R_g$ and $R_h$, together with the nitrogen to which they are attached, include heterocycles and heteroaryl groups such as those known in the quinolone art, for instance, as described above for compounds of Formula I.

A preferred group of compounds of Formula VII are compounds wherein $R_1$ is cyclopropyl; $R_2$ is H, OH, or $NH_2$; $R_3$ is H; $R_4$ is F; and $R_g$ and $R_h$, together with the nitrogen to which they are attached, are 1-pyrrolidinyl or substituted 1-pyrrolidinyl, 1-piperidinyl or substituted 1-piperidinyl, 1-piperizinyl or substituted 1-piperizinyl.

Another preferred group of compounds of Formula VII are compounds wherein $R_1$ is cyclopropyl; $R_2$ is H, OH, or $NH_2$; $R_3$ is H; $R_4$ is F; and $R_g$ and $R_h$, together with the nitrogen to which they are attached, are 1-pyrrolidinyl or substituted 1-pyrrolidinyl, or 1-piperidinyl or substituted 1-piperidinyl.

Another preferred group of compounds of Formula VII are compounds wherein $R_1$ is cyclopropyl; $R_2$ is H or $NH_2$; $R_3$ is H; $R_4$ is F; and $R_g$ and $R_h$, together with the nitrogen to which they are attached, are 1-pyrrolidinyl or substituted 1-pyrrolidinyl.

Another preferred group of compounds of Formula VII are compounds wherein $R_1$ is cyclopropyl; $R_2$ is H or $NH_2$; $R_3$ is H; $R_4$ is F; $R_g$ and $R_h$, together with the nitrogen to which they are attached, are substituted 1-pyrrolidinyl.

Representative compounds of the invention which are compounds of Formula VI are shown in Table 2-III.

In compounds of Formula VIII, a preferred value for m is 0 or 1. A preferred value for X is O. Another prefered value for X is CH$_2$ or CH(C$_1$–C$_7$ alkyl). A preferred value for Y is CH$_2$ or CH(C$_1$–C$_7$ alkyl). Another preferred value for Y is NH or N(C$_1$–C$_7$ alkyl). A preferred value for R$_j$ is C$_1$–C$_7$ alkyl. A preferred value for R$_2$ is NH$_2$. Another preferred value for R$_2$ is H. Another preferred value for R$_2$ is OH. A preferred value for R$_3$ is H. Another preferred value for R$_3$ is methyl. Another preferred value for R$_3$ is methoxy. Another preferred value for R$_3$ is NH$_2$. A preferred value for R$_4$ is F. Another preferred value for R$_4$ is Cl. A preferred value for R$_5$ is 1-pyrrolidinyl or substituted 1-pyrrolidinyl. Another preferred value for R$_5$ is 1-piperidinyl or substituted 1-piperidinyl, or 1-piperizinyl or substituted 1-piperizinyl. Other preferred values for R$_5$ include heterocycles and heteroaryl groups such as those known in the quinolone art, for instance, as described above for compounds of Formula I.

A preferred group of compounds of Formula VIII are compounds wherein m is 1; X is O or CH$_2$; Y is CH$_2$, CH(C$_1$–C$_7$ alkyl), NH, or N(C$_1$–C$_7$ alkyl); R$_j$ is methyl; R$_2$ is H, OH, or NH$_2$; R$_3$ is H; R$_4$ is F or Cl; and R$_5$ is 1-pyrrolidinyl or substituted 1-pyrrolidinyl, 1-piperidinyl or substituted 1-piperidinyl, 1-piperizinyl or substituted 1-piperizinyl.

Another preferred group of compounds of Formula VIII are compounds wherein X is O or CH$_2$; Y is CH$_2$, CH(C$_1$–C$_7$ alkyl), NH, or N(C$_1$–C$_7$ alkyl); R$_j$ is methyl; R$_2$ is H or NH$_2$; R$_3$ is H; and R$_5$ is 1-pyrrolidinyl or substituted 1-pyrrolidinyl, or 1-piperidinyl or substituted 1-piperidinyl.

Another preferred group of compounds of Formula VIII are compounds wherein X is O or CH$_2$; Y is CH$_2$, CH(C$_1$–C$_7$ alkyl), NH, or N(C$_1$–C$_7$ alkyl); R$_j$ is methyl; R$_2$ is H or NH$_2$; R$_3$ is H; R$_4$ is F or Cl; and R$_5$ is 1-pyrrolidinyl or substituted 1-pyrrolidinyl.

Another preferred group of compounds of Formula VIII are compounds wherein X is O or CH$_2$; Y is CH$_2$, CH(C$_1$–C$_7$ alkyl), NH, or N(C$_1$–C$_7$ alkyl); R$_j$ is methyl; R$_2$ is H or NH$_2$; R$_3$ is H; and R$_5$ is substituted 1-pyrrolidinyl.

Representative compounds of the invention which are compounds of Formula VIII are shown below in Table 2-VIII.

TABLE 2-VIII

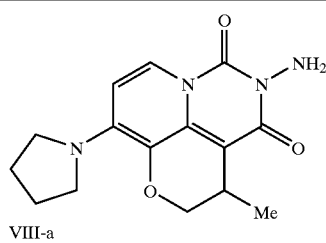

VIII-a

VIII-b

TABLE 2-VIII-continued

VIII-c

VIII-d

Representative compounds of the present invention, which are encompassed by Formula 2-VIII include, but are not limited to the compounds in Table 2-VIII and their pharmaceutically acceptable acid or base addition salts, or amide or prodrugs thereof.

Processes and novel intermediates for preparing compounds of Formula I–VIII are provided as further embodiments of the invention and are illustrated by the following procedures in which the meanings of the generic radicals are as given above unless otherwise qualified. In some cases, protecting groups may have been used to allow synthetic manipulation of one functional group in the presence of other functional groups. It is therefore to be noted that, although not specifically noted in Schemes 1–7, the appropriate use and choice of protecting groups is well-known by one skilled in the art, and is not limited to the specific examples below. It is also to be understood that such groups not only serve to protect chemically reactive sites, but also to enhance solubility or otherwise change physical properties. A good general reference for protecting group preparation and deprotection is Greene, Theodora, *Protective Groups in Organic Synthesis;* Wiley: New York, USA, 1991.

Further in regards to Schemes 1–7, a number of general reactions such as oxidations and reductions, etc. are not shown in detail but can be done by methods understood by one skilled in the art. General transformations are well-reviewed in Larock, Richard. *Comprehensive Organic Transformations;* Wsiley: New York, USA, 1999, and the series "Compendium of Organic Synthetic Methods" published by Wiley-Interscience. In general, the starting materials are obtained from commercial sources unless otherwise indicated.

Structures encompassed by Formula I wherein J is C and K is C or N can be prepared as described in Scheme 1. It is to be understood that when K is N in any of the compounds shown in Scheme 1, R$_6$ is absent. When K is C in Scheme 1, R$_6$ can be as defined above. It is additionally to be understood that compounds shown in Scheme 1 wherein K is N can be prepared according to the method disclosed in WO 91/16894. Thus, nitrile 1 (Qun Li et al. Heterocycles (1999), 51(6), 1345–1353.) can be converted into amide 2 by partial hydrolysis using any number of methods known by those skilled in the art. Treatment of amide 2 with a carbon monoxide equivalent such as phosgene provides a pyrido[1,2-c]pyrimidine ring system 3. The amination of the 2-position NH of 3 can be achieved using any number of aminating reagents as described by Kloetzer (*Sci. Pharm.,* 1984; 52: 46–50). The intermediate wherein $R_5$ is Cl or F (Compound A1), can be coupled with various heterocyclic amines to produce the desired derivatives. Alternatively, if $R_5$ is a bromo, iodo or triflate group, various carbocyclic and aryl moieties may be introduced at $R_5$ using palladium-catalyzed coupling procedures using appropriately substituted tin or boronate reagents.

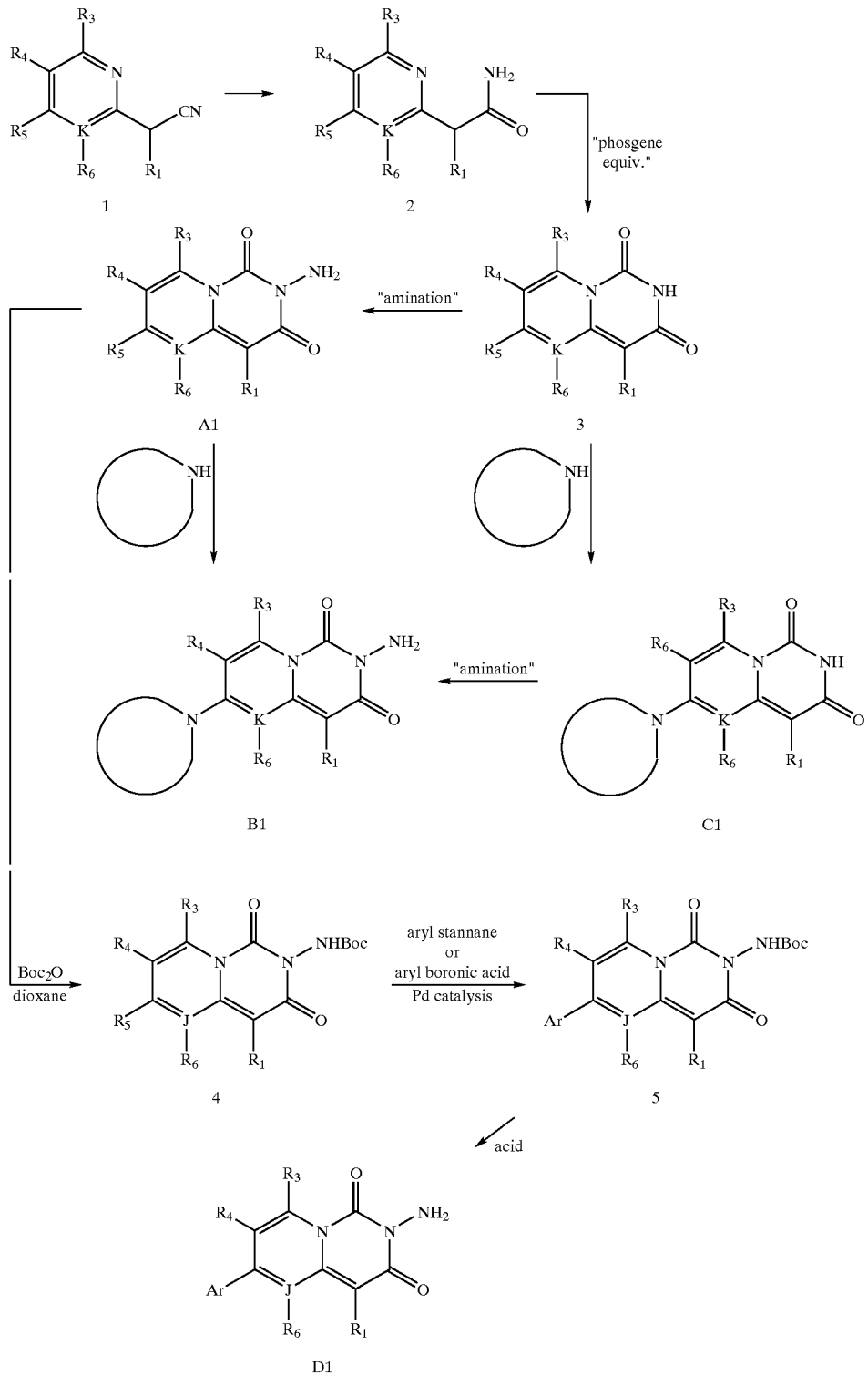

Scheme 1

It is to be recognized from Scheme 1 that $R_1$ and $R_6$, taken together, may form a ring having substituents, providing chiral centers that may give rise to R and S enantiomers as well as diastereomers. It is also to be recognized that $R_5$ sidechains (Compounds B1, C1, and D1) may also, with appropriate substitution, have chiral centers giving R and S enantiomers and diastereomers. Such enantiomers or diastereomers may be separated by any of the methods indicated above at any stage. Resolution of any intermediate may also be accomplished by fractional crystallization using mandelic acid, tartaric acid, or other chiral, optically pure acid or base bearing resolving agents. The isomers can then be separated and the chiral amide hydrolyzed.

An additional approach to the synthesis of an intermediate useful in the preparation of compounds of Formula I wherein J and K are C is summarized in Scheme 2. Thus, substituted pyridine 6 (Qun Li et al. *J. Med. Chem.* 1996, 39(16), 3070–3088) is converted into 11 (A1 in Scheme 1) in a fashion similar to that described above. (Qun Li et al. *Heterocycles* 1999, 51(6), 1345–1353.). Intermediate 6 is then treated with hydrazine in alcoholic solvent to provide 7. Treatment of 7 with oxygen in the presence of a base such as NaOH provides compound 8. Upon treatment with metalated cyclopropyl acetonitrile, compound 8 generates compound 9. Reaction of compound 10 with an acid-for example, HCl or trifluoacetic acid—and subsequent conversion of the resulting phenol to the triflate or alternatively, treatment with a source of Br, Cl, such as phosphorous oxychloride, or the like, provides 11. This intermediate may then be converted into 11(A1) as described in Scheme 1.

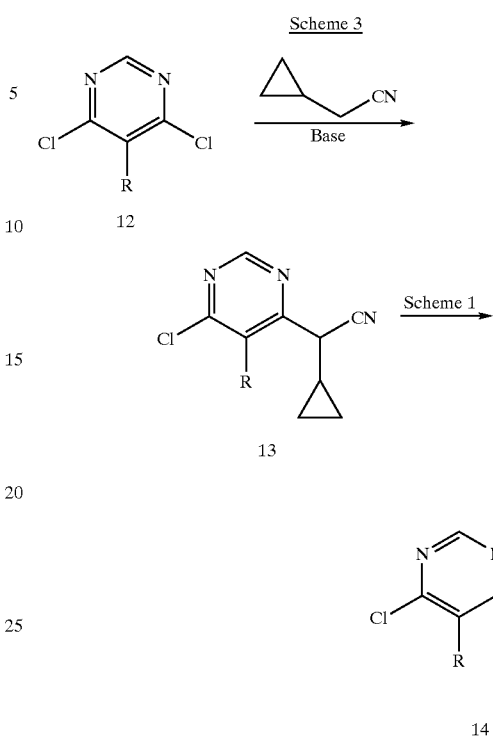

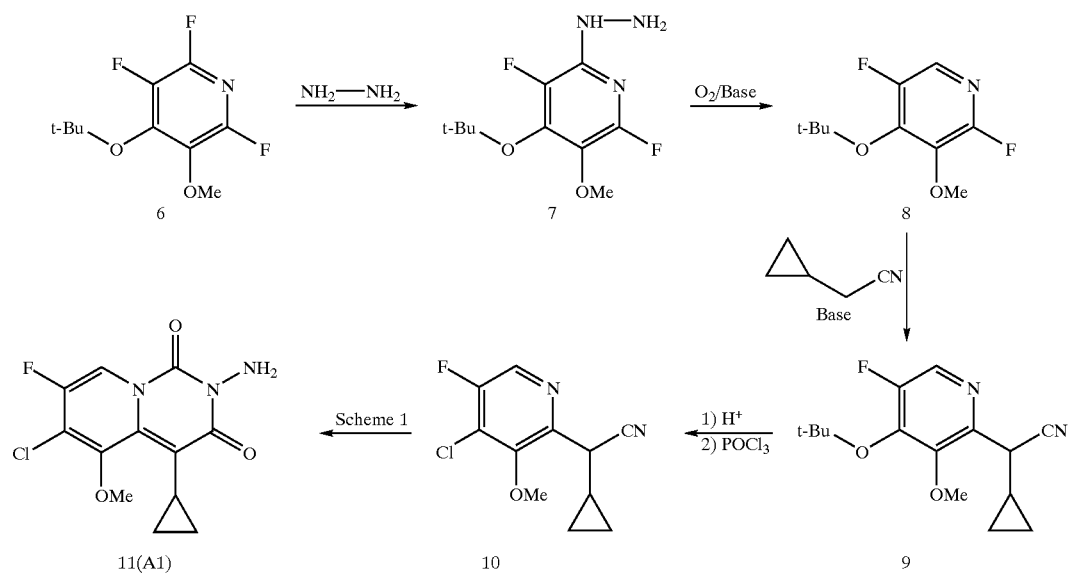

Structures encompassed by Formula I wherein J is N and K is C can be prepared as described in Scheme 3. It is to be understood that when J is N in any of the compounds shown in Scheme 3, $R_4$ is absent. Thus, dichorodiazine 12 can undergo reaction with metalated cyclopropyl acetonitrile to provide compound 13. Using the methodology summarized in Scheme 1, compound 13 can undergo cyclization using a carbon monoxide equivalent to provide bicyclic system 14. Compound 14 can be converted to various compounds of the invention bearing an $R_5$ substituent, also according to Scheme 1.

Structures encompassed by Formula I wherein J is N and K is N can be prepared as described in Scheme 4. It is to be understood that when J is N in any of the compounds shown in Scheme 3, $R_4$ is absent. Thus, dichlorotriazine 15 [*Agric. Biol. Chem.* 1982, 46(6), 1439] can undergo reaction with metalated cyclopropyl acetonitrile to provide compound 16. Using the methodology summarized in Scheme 1, compound 16 can undergo cyclization using a carbon monoxide equivalent to provide bicyclic system 17. Compound 17 can be converted to various compounds of the invention bearing an $R_5$ substituent, also according to Scheme 1.

Scheme 4

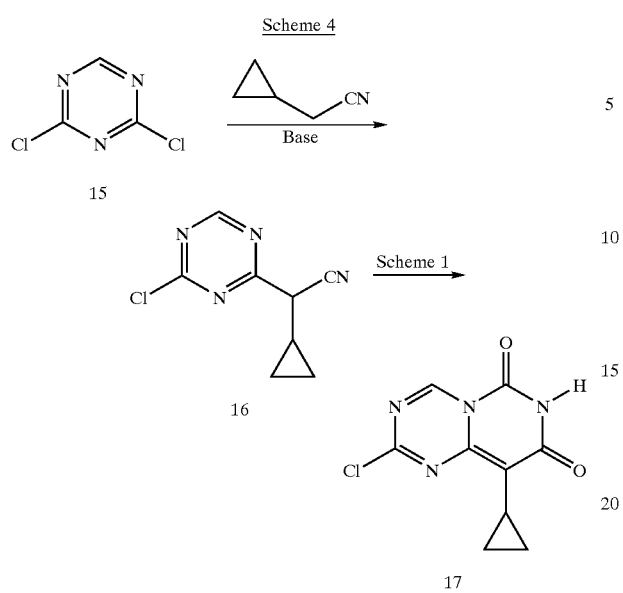

Structures encompassed by Formula VIII can be prepared as summarized in Schemes 5 and 6. Scheme 5 provides an approach to Formula VIII compounds wherein m is 1, X is O or CH₂, and Y is CH—Me. Compound 25a wherein X and Y are CH₂ can be prepared from compound 18a. Thus, compound 18a can be metallated according to methods known to those skilled in the art via deprotonation using an alkyl lithium reagent, followed by "quenching" with a borane, stannane, zinc, or copper reagent, or the like, to provided metallated intermediate 19a wherein V is a borane, stannane, or other organometallic moiety known in the art. Intermediate 19a can undergo reaction with a compound such as with commercially available 2-methyl-2-vinyl oxirane 20a (Aldrich Handbook of Fine Chemicals and Laboratory Equipment, 2002) under palladium catalyzed conditions or in a $S_N2'$ fashion to provide vinyl compound 21a. Hydrogenation of the double bond in compound 21a gives rise to the butanol derivative 22a. Conversion of the alcohol moiety in compound 22a to a leaving group such as a halide, mesylate, tostlate, triflate, etc., followed by treatment with cyanide, will provide the nitrile compound 23a. Base treatment of nitrile 23a can give rise to the bicylic intermediate 24a, which can be converted to the compound of Formula VIII 25a as provided earlier in the instant application.

Scheme 5

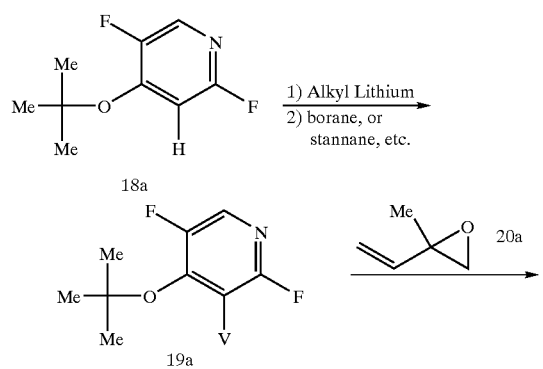

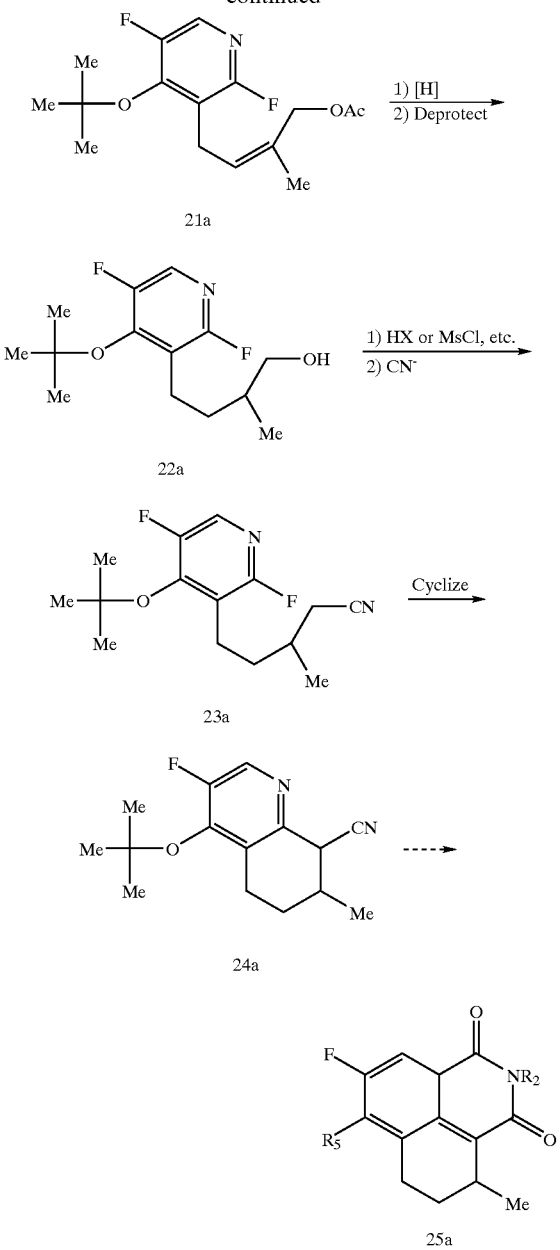

As summarized in Scheme 6, compounds of formula VIII wherein X is O can be prepared in a similar fashion. Treatment of phenol 18b with base can provide the phenoxide 19b. Reaction of compound 19b with a compound such as 20b can give rise to the vinyl derivative 21b. Hydrogenation of the double bond in compound 21b followed by the series of steps provided in Schem 5e provides 25b.

Scheme 6

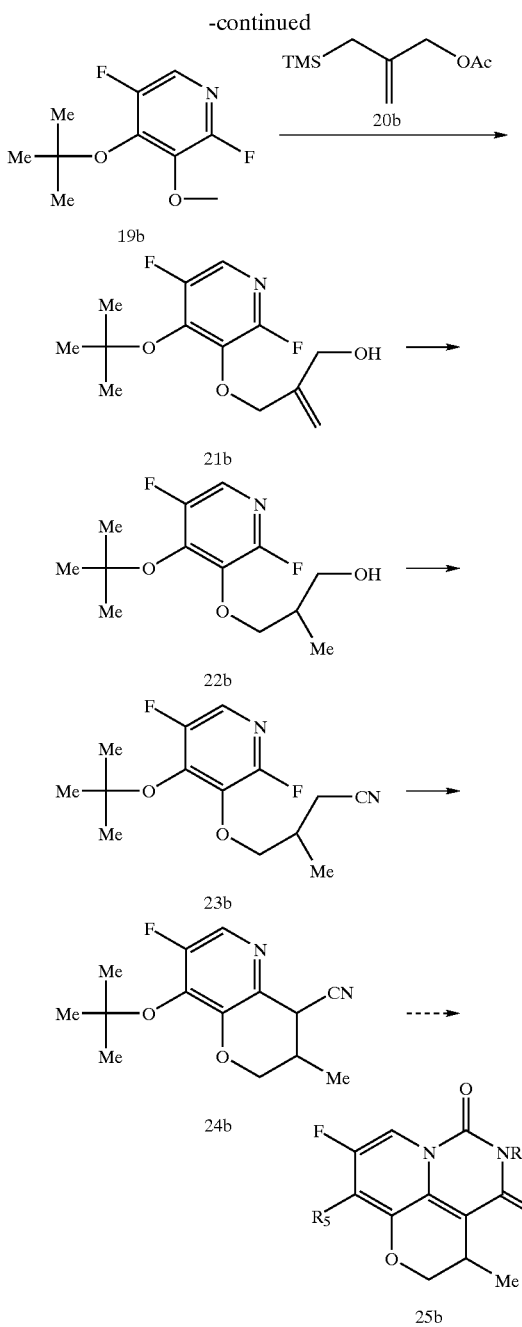

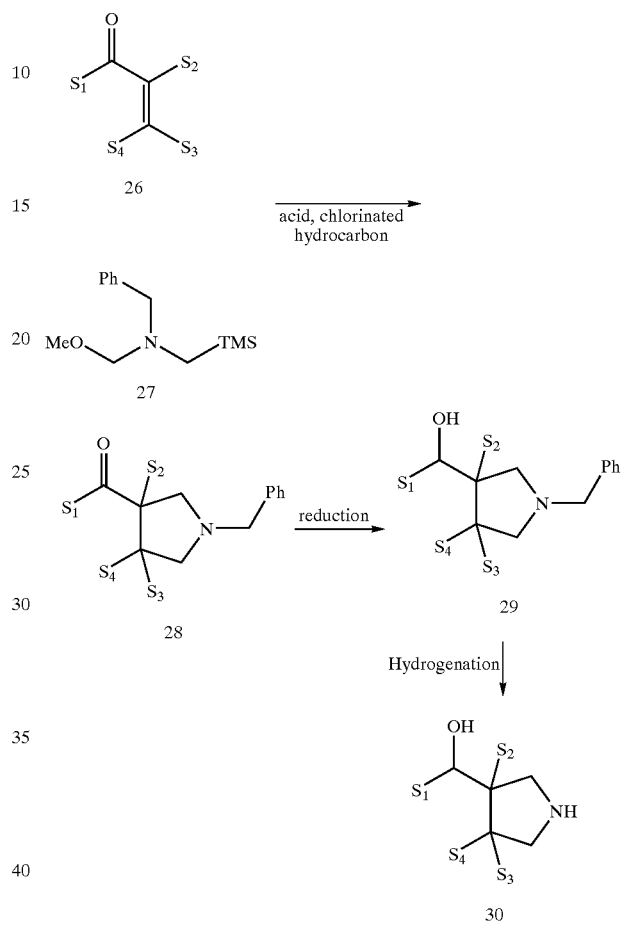

Schemes 7–9 summarize the preparation of $R_5$ sidechains for compounds of Formula I wherein $R_5$ is a variously substituted nitrogen-containing heterocycle, wherein the point of attachment is the nitrogen of the heterocycle. According to Scheme 7, appropriately activated enones can undergo [3+2] cycloadditions under the conditions described by Tsuge et al. (See Recent advances in azomethine ylid chemistry: Advances in Heterocyclic Chemistry (Katritsky, A. ed.) Academic Press; San Diego USA, 231–349). Thus, compound 26 can undergo reaction with compound 27 in a chlorinated hydrocarbon such as dichloromethane, chloroform, dichloroethane or the like, in the presence of a catalytic acid such as trifluoacetic acid, to provide a substituted pyrrolidine 28, wherein $S_1$, $S_2$, $S_3$, $S_4$ are each independently alkyl, substituted alkyl, or aryl. Pyrrolidine 28 can then be reduced using sodium borohydride or a similar reducing agent under a variety of conditions known to those skilled in the art to provide alcohol-substituted pyrrolidine 29. Pyrrolidine 29 subsequently can be deprotected by hydrogenation and the resulting pyrrolidine 30 can be used in the preparation of 2-aminopyrido[1,2-c]pyrimidines and congeners as shown in Scheme 1.

In Scheme 8, a 3-carboxypyrrolidinone 31 [Culbertson, Townley P.; Domagala, John M.; Nichols, Jeffery B.; Priebe, Stephen; Skeean, Richard W. *J. Med. Chem.* 1987, 30(10), 1711] can be converted into an acid chloride or Weinreb amide 32 [Nahm, Steven; Weinreb, Steven M. *Tetrahedron Lett.* 1981, 22(39), 3815]. Acid chlorides and Weinreb amides 32 can be converted into ketones 33 ($S_1$ is defined as in Scheme 2) by treatment with an organocopper reagent or Grignard reagent, respectively. These intermediates 33 can then be treated with hydroxylamine or any O-alkylated or -arylated hydroxylamine under a variety of conditions known to those skilled in the art to provide oximated substituted pyrrolidines 34. The oximes 34 can then be reduced to amines 35 with lithium aluminum hydride, diisobutylaluminum hydride, borane or by selective catalytic hydrogenation by those skilled in the art. The resulting primary amines can then be protected using a number of methods as decribed in *Protective Groups in Organic Synthesis* by Green and Wuts. The benzylic pyrrolidine 35 can then be deprotected by hydrogenation and the resulting pyrrolidine 36 used in the preparation of pyrido[1,2-c] pyrimidines and congeners as shown in Scheme 1. The use of S-methylbenzyl (or R-methylbenzyl) as a protecting group for the pyrrolidine nitrogen allows for the separation of enantiomers and diastereomers at any step in the reaction sequence.

Scheme 8

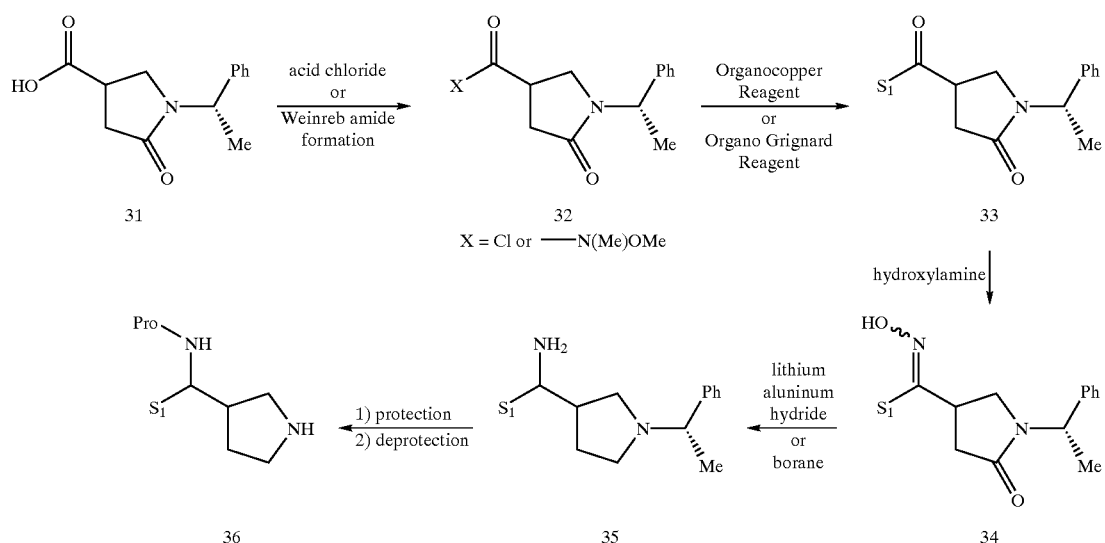

Scheme 9 provides a synthesis for an additional pyrrolidinyl sidechain, compound 42, using techniques known to those skilled in the art. In one approach, acid 37 was treated with isobutyl cholorformate in the presence of base to form the mixed anhydride. Conversion of the mixed anhydride to the diazomethyl compound using 1-methyl-3-nitro-1-nitrosoguanidine and KOH, followed by treatment with HBr/HOAc, gave rise to α-bromomethyl ketone 38. Alpha-bromomethyl ketone 38 was readily converted to the fluoromethyl ketone 39 using a fluorine source such as KF. Reductive amination of 39 using benzylamine and a reducing agent such as sodium triacetoxyborohydride provided fluoroethylamino derivative 40. Reduction of the amide moiety in compound 40, followed by hydrogenolysis to remove the benzyl moieties provided the target compound 41.

Scheme 9

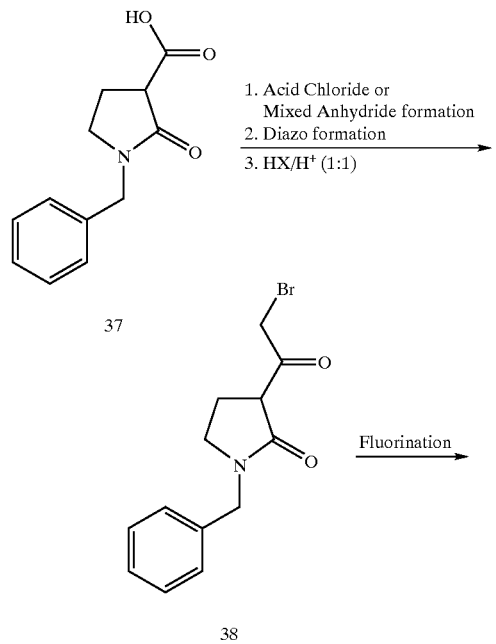

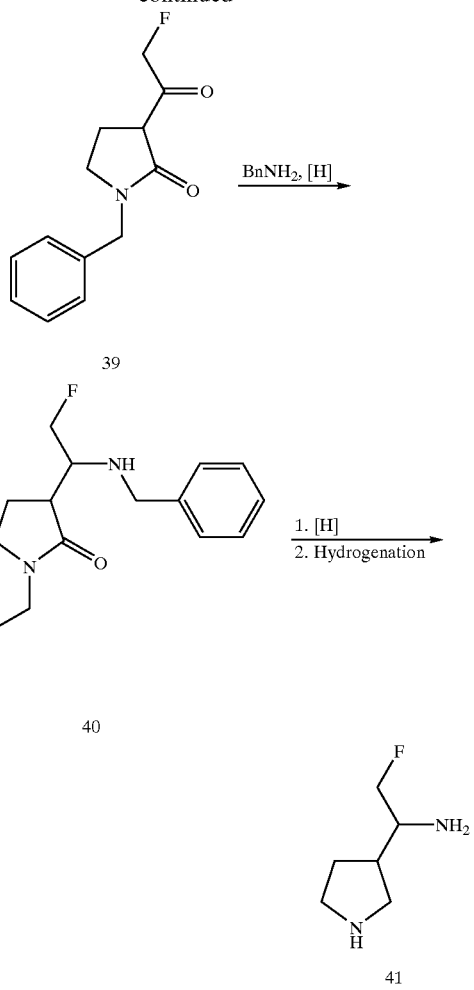

Certain compounds of Formula I are also useful as intermediates for preparing other compounds of Formula I. Thus, a compound wherein $R_2$ is $NR_2$, can be metabolized to form another compound of the invention wherein $R_2$ is H. This conversion can occur under physiological conditions. To that end, both the non-metabolized compound of the invention and the metabolized compound of the invention— that is, the compound wherein $R_2$ is $NR_2$ and the compound wherein $R_2$ is H—can have antibacterial activity.

Some of the compounds of Formula I are capable of further forming pharmaceutically acceptable acid-addition and/or base salts. All of these forms are within the scope of the present invention. Thus, pharmaceutically acceptable acid addition salts of the compounds of Formula I include salts derived from nontoxic inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, acetate, trifluoroacetate, propionate, caprylate, isobutyrate, oxalate, malonate, succinates suberate, sebacate, fumarate, maleate, mandelate, benzoate, chlorobenzoate, methylbenzoate, dinitrobenzoate, phthalate, benzensoulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge S. M. et al., "Pharmaceutical Salts," *Journal of Pharmaceutical Science,* 1977;66:1–19).

The acid addition salt of said basic compounds are prepared by contacting the free base form with a sufficient amount of the desired acid to produce the salt in the conventional manner.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge S. M., supra., 1977).

The base addition salts of said acidic compounds are prepared by contacting the free acid form with a sufficient amount of the desired base to produce the salt in the conventional manner.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention possess one or more chiral centers and each center may exist in the R(D) or S(L) configuration. The present invention includes all enantiomeric and epimeric forms, as well as the appropriate mixtures thereof.

The compounds of Formula I can be Formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or Formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of Formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of Formula I can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of Formula I in a liquid composition, such as a lotion, will be from about 0.1–25 wt-%, preferably from about 0.5–10 wt-%. The concentration in a semi-solid or solid composition such as a gel or a powder will be about 0.1–5 wt-%, preferably about 0.5–2.5 wt-%.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound may conveniently be administered in unit dosage form; for example, containing 5 to 1000 mg, conveniently 10 to 750 mg, most conveniently, 50 to 500 mg of active ingredient per unit dosage form.

Ideally, the active ingredient should be administered to achieve peak plasma concentrations of the active compound of from about 0.5 to about 75 $\mu$M, preferably, about 1 to 50 $\mu$M, most preferably, about 2 to about 30 $\mu$M. This may be achieved, for example, by the intravenous injection of a 0.05 to 5% solution of the active ingredient, optionally in saline, or orally administered as a bolus containing about 1–100 mg of the active ingredient. Desirable blood levels may be maintained by continuous infusion to provide about 0.01–5.0 mg/kg/hr or by intermittent infusions containing about 0.4–15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The ability of a compound of the invention to inhibit bacterial growth is demonstrated using pharmacological models that are well known to the art, for example, using models such as the tests described below.

Test A—Antibacterial Assay

The compounds of the present invention were tested against an assortment of Gram-negative and Gram-positive organisms using standard microtitration techniques (Cohen, et al., *Antimicrob. Agents Chemother.,* 1985;28:766; Heifetz, et al., *Antimicrob. Agents Chemother.,* 1974;6:124). The results of the evaluation are shown in Table 3 and are compared to ciprofloxacin.

TABLE 3

Antibacterial and *E. coli* gyrase Activities

Minimum Inhibitory Concentrations $\mu$g/mL

| Compound Number or Structure | Gram Negatives | | | Gram Positives | | | *E. coli* gyrase IC$_{50}$ ($\mu$M) |
|---|---|---|---|---|---|---|---|
| | *E. coli* MC 4100 | *E. coli* B90 | *E. coli* Tol C | *E. faecalis* RB1 | *S. aureus* 29213 | *S. pyogenes* C203 | |
| 4f | 2.0 | 0.13 | 0.03 | 0.06 | 0.25 | 0.015 | 1.0 |
| 4g | 16.0 | 0.25 | <0.06 | 2.0 | 1.0 | 1.0 | 1.7 |
| 4h | 16.0 | 0.13 | <0.06 | 2.0 | 0.5 | 2.0 | 1.2 |
| 4i | 0.5 | 0.03 | 0.015 | 0.06 | 0.06 | 0.015 | 0.64 |
| 4j | 2.0 | 0.25 | 0.13 | 0.5 | | 0.03 | 1.5 |
| 5b | 0.5 | 0.06 | 0.03 | 0.13 | 0.25 | 0.008 | 0.5 |
| 5c | 16.0 | 2.0 | 0.5 | 2.0 | 2.0 | 0.5 | 0.7 |
| Ciprofloxacin | <0.02 | <0.01 | <0.01 | 0.5 | 0.5 | 0.5 | 0.2 |

Test B—DNA Gyrase Assay

The effects of test agents on the activity of DNA gyrase was determined by the supercoiling inhibition assay, following reaction conditions recommended by the enzyme supplier (Lucent, Ltd., Leicester, UK), as follows: Reactions are performed in buffer G (35 mM Tris-HCl (pH 7.5), 24 mM KCl, 4 mM $MgCl_2$, 2 mM DTT, 1.8 mM spermidine, 1 mM ATP, 0.1 mg/mL bovine serum albumin). Relaxed plasmid pBR322 (0.25 μg, Lucent, Ltd., Leicester, UK) is reacted with 1 U E. coli gyrase (Lucent, Ltd., Leicester, UK), in the absence or presence of drugs, for 30 minutes at 37° C. Reactions were stopped by the addition of SDS and proteinase K to respective final concentrations of 1% and 0.5 mg/mL. After an additional 30 minutes at 37° C., one-tenth volume of 10x loading buffer (0.3% bromophenol blue, 16% Ficoll, 10 mM $Na_2HPO_4$) was added, and reactions were loaded onto agarose gels and electrophoresed as described for intercalation assays (Y. Pommier et al. *Nucleic Acids Research* 1987, 15, 6713–6731.). The concentration of drug inhibiting 50% of the supercoiling activity of DNA gyrase was measured and is given as an $IC_{50}$ in Table 4. The in vivo activity was obtained when the compounds were tested according to the procedure of Miller, et al. (*Proc. Soc. Exp. Biol. Med.*, 1944;57:261). The median protective dose ($PD_{50}$) was determined in mice given lethal systemic infections, as depicted in Table 4. Compound 4f is compared to ciprofloxacin.

TABLE 4

In Vivo Median Protective Dose ($PD_{50}$) in Mice (PO)

| Compound Number or Structure | Organism | $PD_{50}$ (mg/kg) |
|---|---|---|
| 4f | S. pyogenes | 1.2 |
| 4i | S. pyogenes | 2.1 |
| Ciprofloxacin | S. pyogenes | >100 |

Test C—Cross Resistance Antibacterial Assay

The compounds of the present invention were tested against an assortment of ciprofloxacin resistant E. coli and S. aureus organisms described below using standard microtitration techniques (Cohen, et al., *Antimicrob. Agents Chemother.*, 1985;28:766; Heifetz, et al., *Antimicrob. Agents Chemother.*, 1974;6:124). The results of the evaluation are shown in Table 5 compared to ciprofloxacin.

N. gonorrhoeae and S. aureus Organisms:

N. gonorrhoeae 2637 (N.g. 2637) is a derivative of *Neisseria gonorrhoeae* MS11 containing a TAC-LAC recA to allow for control of homologous recombination [Tonjum T. et al. *Molecular Microbiology* 1995, 16, 451–64].

N. gonorrhoeae 2709 (N.g. 2709): Isogenic to N. gonorrhoeae 2637 contains gyrA quinolone—resistant determining region (QRDR) mutations (S91F D95G).

N. gonorrhoeae 2693 (N.g. 2693): Isogenic to N. gonorrhoeae 2709 containing parC QRDR mutations [P88S and E91K].

S. aureus UC-76: Typical sensitive laboratory strain (Wild type).

S. aureus 2552: Isogenic to S. aureus UC-76, with upregulated norA pump.

S. aureus 2554: Isogenic to S. aureus 2552, with point mutation at position 80 of grlA subunit.

S. aureus 2558: Isogenic to S. aureus 2554, with point mutation at position 84 of gyrA subunit.

TABLE 5

Antibacterial Activities Against Ciprofloxacin Resistant Strains

| Compound Number or Structure | Minimum Inhibitory Concentrations μg/mL | | | | | | |
|---|---|---|---|---|---|---|---|
| | N. g. 2637 | N. g. 2709 | N. g. 2693 | S. aureus UC-76 | S. aureus 2552 | S. aureus 2554 | S. aureus 2558 |
| 4f | 0.25 | 0.5 | 1.0 | 0.06 | 0.5 | 0.13 | 0.5 |
| 4h | | | | 0.5 | 1 | 1 | 1 |
| 4i | 0.03 | 0.13 | 0.13 | 0.06 | 0.06 | 0.06 | 0.13 |
| 5b | 0.13 | 0.25 | 0.25 | 0.06 | 0.25 | 0.13 | 1 |
| Ciprofloxacin | 0.002 | 0.06 | 2.0 | 0.13 | 2 | 2 | 64 |

The antibacterial agents described in this invention display Gram-negative and Gram-positive activity. The compounds also show inhibition of bacterial DNA gyrase.

Finally, the compounds demonstrate in vivo protective activity in mice and are not highly cytotoxic to mammalian cells indicating selectivity for bacteria.

The invention will now be demonstrated by the following non-limiting examples.

EXAMPLE 1

2-(4-Chloro-5-fluoro-3-methylpyridin-2-yl)-2-cyclopropylacetamide

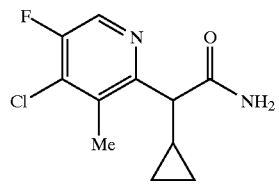

2-(4-Chloro-5-fluoro-3-methyl-2-pyridinyl)cyclopropylacetonitrile (10.0 g, 44.5 mmol, [Qun Li et al. *Heterocycles* 1999, 51(6), 1345–1353]) was added to a stirred solution of sulfuric acid (10 mL) and acetic acid (30 mL). The resulting mixture was heated for 2 hours at 100° C. The mixture was then cooled and made alkaline with ammonia to pH 9. The product was extracted with chloroform (3×60 mL). The extracts were combined, dried over sodium sulfate and evaporated to afford the title compound (8.6 g). MSCI: m/z=243 ($MH^+$).

EXAMPLE 2

6-Chloro-4-cyclopropyl-7-fluoro-5-methyl-pyrido[1,2-c]pyrimidine-1,3-dione

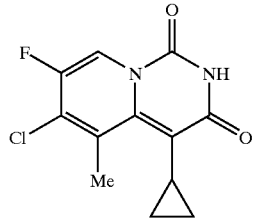

To a −60° C. solution of 2-(4-chloro-5-fluoro-3-methylpyridin-2-yl)-2-cyclopropylacetamide (2.7 g, 11.0 mmol (Example 1)) and triphosgene (7.2 g, 24.0 mmol) in dichloromethane (250 mL) was added portionwise potassium tert-butoxide (4.5 g, 40.0 mmol). After the addition was complete, the mixture was stirred at −50° C. for 30 minutes. Water was then added at this temperature. The organic layer was separated, washed with brine (3×), dried over sodium sulfate, filtered, and evaporated. The residue was purified by column chromatography (7:3 ethyl acetate/hexanes) to afford the title compound (2 g). $^1$H NMR (200 MHz, CDCl$_3$) δ 8.95 (bs, 1H), 8.16 (d, 1H), 2.66 (s, 3H), 1.75–1.71 (m, 1H), 1.11–1.01 (m, 2H), 0.46–0.37 (m, 2H). MSCI: m/z=269 (MH$^+$).

EXAMPLE 3

2-Amino-6-chloro-4-cyclopropyl-7-fluoro-5-methylpyrido[1,2-c]pyrimidine-1,3-dione

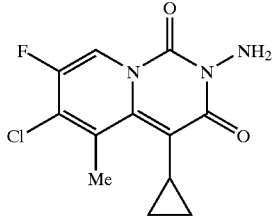

To a 5° C. solution of 6-chloro-4-cyclopropyl-7-fluoro-5-methyl-pyrido[1,2-c]pyrimidine-1,3-dione (0.76 g, 2.8 mmol (Example 2)) in a mixture of dry tetrahydrofuran (20 mL) and dry dimethylformamide (10 mL) was added sodium hydride (0.12 g, 3.0 mmol, 60% mineral dispersion) portionwise. After stirring at room temperature for 30 minutes, 2,4-dinitrophenylhydroxylamine (0.65 g, 3.00 mmol) was added. The mixture was then heated at 80° C. for 45 minutes, cooled to ambient temperature, poured into ice water, and extracted with dichloromethane. The combined extracts were washed with brine, dried with sodium sulfate and concentrated. The residue was purified by column chromatography (9:1 ethyl acetate/hexanes) to afford the title compound (0.635 g). MSCI: m/z=284 (MH$^+$).

EXAMPLE 4
General Procedure

A solution of 2-amino-6-chloro-4-cyclopropyl-7-fluoro-5-methyl-pyrido[1,2-c]pyrimidine-1,3-dione (Example 3) and a substituted pyrrolidine (3 eq.) in dimethyl sulfoxide was heated at 60° C. for 5 hours. The mixture was cooled to ambient temperature, diluted with water and filtered. The product was purified by column chromatography to afford each of the following title compounds:

(a) {(R)-1-[(R)-1-(2-Amino-4-cyclopropyl-7-fluoro-5-methyl-1,3-dioxo-2,3-dihydro-1H-pyrido[1,2-c]pyrimidin-6-yl)-pyrrolidin-3-yl]ethyl}carbamic acid, tert-butyl ester (MSCI: m/z=462 (MH$^+$)) from ((R)—(R)-1-pyrrolidinin-3-yl-ethyl)carbamic acid, tert-butyl ester [D. R Johnson et al. *J. Heterocycl. Chem.* 1992, 29(6), 1481–8].

(b) {(S)-1-[(R)-1-(2-Amino-4-cyclopropyl-7-fluoro-5-methyl-1,3-dioxo-2,3-dihydro-1H-pyrido[1,2-c]pyrimidin-6-yl)-pyrrolidin-3-yl]ethyl}carbamic acid, tert-butyl ester (MSCI: m/z=462(MH$^+$)) from ((S)—(R)-1-pyrrolidinin-3-yl-ethyl)carbamic acid, tert-butyl ester [ester [Don R Johnson et al. *J. Heterocycl. Chem.* 1992, 29(6), 1481–8].

(c) {1-[1-(2-Amino-4-cyclopropyl-7-fluoro-5-methyl-1,3-dioxo-2,3-dihydro-1-H-pyrido[1,2-c]pyrimidine-6-yl)-4,4-dimethylpyrrolidin-3-yl]-ethyl}carbamic acid, tert-butyl ester (MS (EI, M+1) m/z=490) from [1-(4,4-dimethyl-pyrrolidin-3-yl)ethyl]carbamic acid, tert-butyl ester [U.S. Provisional App. Ser. No. 60/241267, filed Oct. 18, 2000, Warner Lambert Docket No. A0000072].

(d) [1-(2-Amino-4-cyclopropyl-7-fluoro-5-methyl-1,3-dioxo-2,3-dihydro-1H-pyrido[1,2-c]pyrimidin-6-yl)pyrrolidin-3-yl]carbamic acid, tert-butyl ester (MSCI: m/z=434(MH$^+$) from pyrrolidin-3-yl-carbamic acid, tert-butyl ester.

(e) {1-[1-(2-Amino-4-cyclopropyl-7-fluoro-5-methyl-1,3-dioxo-2,3-dihydro-1H-pyrido[1,2-c]pyrimidin-6-yl)-4-methylpyrrolidin-3-yl]-ethyl}carbamic acid, tert-butyl ester (MSCI: m/z=476 (MH$^+$)) from [1-(4-methylpyrrolidin-3-yl)-ethyl]carbamic acid tert-butyl ester [U.S. Provisional App. Ser. No. 60/241267, filed Oct. 18, 2000].

(f) 2-Amino-4-cyclopropyl-7-fluoro-5-methyl-6-[3-(1-methylaminoethyl)pyrrolidin-1-yl]pyrido[1,2-c]pyrimidine-1,3-dione (mp=95–97° C.; MSCI: m/z=376 (MH$^+$)) from methyl-(1-pyrrolidin-3-yl-ethyl)amine [J. S. Plummer et al. *Tetrahedron Lett.* 1993, 34(47), 7529–32].

(g) 2-Amino-4-cyclopropyl-7-fluoro-5-methyl-6-pyrrolidin-1-yl-pyrido[1,2-c]pyrimidine-1,3-dione (mp= 202–204° C.; MSCI: m/z=319(MH$^+$)) from pyrrolidine.

(h) 2-Amino-4-cyclopropyl-7-fluoro-6-[3-(1-hydroxyethyl)pyrrolidin-1-yl-5-methylpyrido[1,2-c]pyrimidine-1,3-dione (mp=172–174° C.; MSCI: m/z=363 (MH$^+$)) from 1-pyrrolidin-3-yl-ethanol (Example 6A2).

(i) 2-Amino-6-[(R)-3-(1-aminocyclopropyl)pyrrolidin-1-yl]-4-cyclopropyl-7-fluoro-5-methylpyrido[1,2-c]pyrimidine-1,3-dione ($^1$H NMR (200 MHz, CDCl$_3$) δ 8.20 (d, 1H), 5.42 (bs, 2H), 3.86–3.80 (m, 1H), 3.71–3.63 (m, 1H), 3.52–3.44 (m, 2H), 2.27 (s, 3H), 2.12–2.00 (m, 2H), 1.86–1.72 (m, 2H), 1.62 (bs, 2H), 1.18–1.07 (m, 1H), 0.96–0.83 (m, 1H), 0.67–0.62 (m, 2H), 0.58–0.49 (m, 2H), 0.40–0.29 (m, 2H). MSCI: m/z=374 (MH$^+$).) from (R)-1-pyrrolidin-3-ylcyclopropylamine [*Chem. Pharm. Bull.* 1994, 42, 1442.].

(j) 2-Amino-6-((3S,4S) and (3R,4R)-3-aminomethyl-4-fluoropyrrolidin-1-yl)-4-cyclopropyl-7-fluoro-5-methylpyrido[1,2-c]pyrimidine-1,3-dione ($^1$H NMR (200 MHz, CDCl$_3$) δ 8.21 (d, 1H), 5.42 (bs, 2H), 5.31 (dd, 1H), 4.07 (dd, 1H), 3.84–3.76 (m, 1H), 3.75–3.47 (m, 3H), 3.14–3.08 (m, 1H), 3.02–2.94 (m, 2H), 2.33 (s, 3H), 1.83–1.78 (m, 1H), 1.70 (bs, 2H), 1.22–1.09 (m, 1H), 0.93–0.80 (m, 2H), 0.40–0.29 (m, 1H); MSCI: m/z=366 (MH$^+$)) was prepared from a mixture of (3S,4S) and (3R,4R)-4-fluoropyrrolidin-3-yl)methylamine [*J. Med. Chem.* 1990 33, 1344.].

(k) 2-Amino-6-(3-aminomethylpyrrolidin-1-yl)-4-cyclopropyl-7-fluoro-5-methylpyrido-[1,2-c]pyrimidine-1,3-dione ($^1$H NMR (400 MHz, DMSO) δ 8.19 (d, 1H), 5.71 (bs, 2H), 3.74–3.50 (m, 3H), 3.49–3.38 (m, 1H), 3.31 (bs, 2H), 2.97 (d, 2H), 2.95–2.91 (m, 1H), 2.25 (s, 3H), 2.19–2.09 (m, 2H), 1.72–1.65 (m, 1H), 0.91–0.81 (m, 2H), 0.29–0.22 (m, 2H); MSCI: m/z=348 (MH$^+$)) was prepared from pyrrolidin-3-ylmethylamine [J. Org. Chem. 1961, 26, 4955.].

(l) 2-Amino-6-(3-aminopyrrolidin-1-yl)-4-cyclopropyl-7-fluoro-5-methylpyrido[1,2-c]pyrimidine-1,3-dione ($^1$H NMR (400 MHz, CDCl$_3$) δ 8.20 (d, 1H), 5.40 (bs, 2H), 3.85–3.60 (m, 4H), 3.35–3.30 (m, 1H), 2.35 (s, 3H), 2.30–2.15 (m, 1H), 1.85–1.75 (m, 2H), 1.25 (bs, 2H), 1.00–0.95 (m, 2H), 0.38–0.30 (m, 2H). MSCI: m/z=334 (MH$^+$)) was prepared from pyrrolidin-3-ylamine [JP 03133954, 1991].

(m) 2-Amino-6-(7-amino-5-azaspiro[2.4]hept-5-yl)-4-cyclopropyl-7-fluoro-5-methylpyrido[1,2-c]pyrimidine-1,3-dione ($^1$H NMR (400 MHz, CD$_3$OD) δ 8.20 (d, 1H), 4.90 (bs, 2H), 4.40–4.30 (m, 1H), 4.20–4.13 (m, 1H), 3.75–3.40 (m, 3H), 3.25 (s, 1H), 2.40 (s, 3H), 1.75–1.68 (m, 1H), 1.25 (s, 2H), 1.13–0.70 (m, 7H). MSCI: m/z=360 (MH$^+$)) was prepared using 5-azaspiro[2.4]hept-7-ylamine [PCT Int. Appl. WO 9637470, 1996].

(n) 2-Amino-6-[3-(aminooxazol-4-yl-methyl)pyrrolidin-1-yl]-4-cyclopropyl-7-fluoro-5-methylpyrido[1,2-c]pyrimidine-1,3-dione ($^1$H NMR (400 MHz, CDCl$_3$) δ 8.20 (t, 1H), 7.68 (s, 1H), 7.09 (d, 1H), 5.45 (bs, 2H), 4.12–4.00 (m, 1H), 3.85–3.70 (m, 2H), 3.69–3.45 (m, 2H), 2.80–2.65 (m, 1H), 2.35–2.30 (d, 3H), 2.09–1.95 (m, 5H), 1.10–0.80 (m, 2H), 0.31–0.22 (m, 2H). MSCI: m/z=415 (MH$^+$)) was prepared using oxazol-4-yl-C-pyrrolidin-3-ylmethylamine (Example 6B4).

(o) 2-Amino-6-(4-aminooctahydroisoindol-2-yl)-4-cyclopropyl-7-fluoro-5-methylpyrido[1,2-c]pyrimidine-1,3-dione ($^1$H NMR (400 MHz, d$_4$-MeOH) δ 8.23 (d, 1H), 4.90 (bs, 4H), 4.16–4.01 (m, 2H), 3.60 (m, 1H), 3.35 (s, 2H), 3.20 (d, 1H), 2.85–2.75 (m, 1H), 2.40 (s, 3H), 1.98–1.82 (m, 2H), 1.80–1.60 (m, 3H), 1.58–1.30 (m, 2H), 1.15–1.00 (m, 1H), 0.90–0.78 (m, 1H), 0.40–0.23 (m, 2H). MSCI: m/z=388 (MH$^+$)) was prepared from octahydroisoindol-4-ylamine [M. Ogata et al. Eur. Pat. Appl. (1990), EP 359172].

(p) 2-Amino-6-[3-(1-amino-1-methylethyl)pyrrolidine-1-yl]-4-cyclopropyl-7-fluoro-5-methylpyrido[1,2-c]pyrimidine-1,3-dione ($^1$H NMR (400 MHz, CDCl$_3$) δ 8.18 (d, 1H), 5.40 (s, 2H), 3.91–3.80 (m, 1H), 3.75–3.63 (m, 1H), 3.50–3.39 (m, 3H), 2.40–2.28 (s, 4H), 2.10–1.90 (m, 1H), 1.88–1.73 (m, 2H), 1.32–1.08 (m, 8H), 0.92–0.80 (m, 1H), 0.40–0.25 (m, 2H). MSCI: m/z=376 (MH$^+$)) was prepared using 1-methyl-1-pyrrolidin-3-ylethylamine [WO 01/53273 A1].

EXAMPLE 5

Hydrogen chloride gas was bubbled into ice-cold anhydrous diethyl ether and the resulting saturated diethyl ether solution was added to a solution of a compound of Example 4 in dry dichloromethane to form a suspension. The suspension was sealed and stirred at room temperature for 1 hour. The resulting solids were filtered and washed with diethyl ether/hexanes (2:1). The solid was dried under vacuum to afford the following title compounds:

(a) 2-Amino-6-[(R)-3-((R)-1-amino-ethyl)pyrrolidin-1-yl]-4-cyclopropyl-7-fluoro-5-methylpyrido[1,2-c]pyrimidine-1,3-dione, hydrochloride (mp=218–221° C.; MSCI: m/z=362 (MH$^+$)) from {(R)-1-[(R)-1-(2-amino-4-cyclopropyl-7-fluoro-5-methyl-1,3-dioxo-2,3-dihydro-1H-pyrido[1,2-c]pyrimidin-6-yl)pyrrolidin-3-yl]ethyl}carbamic acid, tert-butyl ester (Example 4a).

(b) 2-Amino-6-[(R)-3-((S)-1-aminoethyl)pyrrolidin-1-yl]-4-cyclopropyl-7-fluoro-5-methyl-pyrido[1,2-c]pyrimidine-1,3-dione, hydrochloride (mp=218–220° C.; MSCI: m/z=362 (MH$^+$)) from {(S)-1-[(R)-1-(2-amino-4-cyclopropyl-7-fluoro-5-methyl-1,3-dioxo-2,3-dihydro-1H-pyrido[1,2-c]pyrimidin-6-yl)-pyrrolidin-3-yl]-ethyl}carbamic acid, tert-butyl ester (Example 4b).

(c) 2-Amino-6-[4-(1-amino-ethyl)-3,3-dimethylpyrrolidin-1-yl]-4-cyclopropyl-7-fluoro-5-methyl-pyrido[1,2-c]pyrimidine-1,3-dione, hydrochloride (mp=238–240° C.; MSCI: m/z=390 (MH$^+$)) from {1-[1-(2-amino-4-cyclopropyl-7-fluoro-5-methyl-1,3-dioxo-2,3-dihydro-1-H-pyrido[1,2-c]pyrimidine-6-yl)-4,4-dimethylpyrrolidin-3-yl]ethyl}carbamic acid, tert-butyl ester (Example 4c).

(d) 2-Amino-6-(3-amino-pyrrolidin-1-yl)-4-cyclopropyl-7-fluoro-5-methylpyrido[1,2-c]pyrimidine-1,3-dione hydrochloride (mp=246–248° C.; MSCI m/z=334 (MH$^+$)) from [1-(2-amino-4-cyclopropyl-7-fluoro-5-methyl-1,3-dioxo-2,3-dihydro-1H-pyrido[1,2-c]pyrimidin-6-yl)-pyrrolidin-3-yl] carbamic acid, tert-butyl ester (Example 4d).

(e) 2-Amino-6-[3-(1-aminoethyl)-4-methylpyrrolidin-1-yl]-4-cyclopropyl-7-fluoro-5-methylpyrido[1,2-c]pyrimidine-1,3-dione, hydrochloride (mp=238–240° C.; MSCI: m/z=376 (MH$^+$)) from {1-[1-(2-amino-4-cyclopropyl-7-fluoro-5-methyl-1,3-dioxo-2,3-dihydro-1H-pyrido[1,2-c]pyrimidin-6-yl)-4-methylpyrrolidin-3-yl]ethyl}carbamic acid, tert-butyl ester (Example 4e).

EXAMPLE 6

Amine Side Chain Synthesis

EXAMPLE 6A1

1-(1-Benzylpyrrolidin-3-yl)ethanol

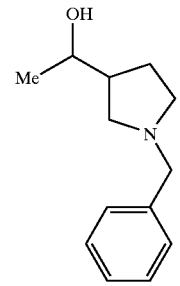

To a 5° C. solution of 3-acetyl-1-benzylpyrrolidine (1 g, 4.9 mmol [L. E. Overman, J. Am. Chem. Soc. 1983, 105, 6622]) in methanol (10 mL) was added portionwise sodium borohydride (0.37 g, 9.8 mmol). After stirring at room temperature for 17 hours, the mixture was concentrated, diluted with ethyl acetate, washed with water, brine, dried with sodium sulfate and concentrated to afford the title compound (0.75 g). MSCI: m/z=206 (MH+).

EXAMPLE 6A2

(1-Pyrrolidin-3-yl)ethanol

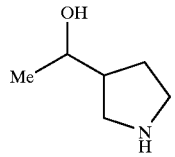

A mixture of 1-(1-benzylpyrrolidin-3-yl)ethanol (4.0 g, 19 mmol), 10% Pd-C (2 g) and ammonium formate (4.8 g, 76 mmol) in methanol (40 mL) was refluxed for 3 hours. The mixture was then allowed to cool and diluted with dichloromethane (80 mL) and filtered. The filtrate was concentrated to afford the title compound (1.97 g). MSCI: m/z=116 (MH+).

EXAMPLE 6B1

4-(Oxazole-4-carbonyl-1-((S)-1-phenylethyl) pyrrolidin-2-one

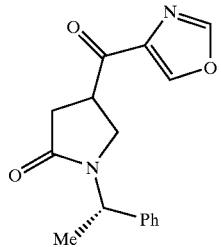

To a cooled solution (−78° C.) of oxazole (10.3 g, 149.1 mmol) in tetrahydrofuran (150 mL) was added n-butyl lithium (2.5 M in hexane, 53.7 mL, 134.2 mmol). The solution was stirred at −78° C. for three hours. To the cold solution was added a solution of 5-oxo-1-((S)-1-phenylethyl)pyrrolidine-3-carboxylic acid, methoxymethylamide (8.2 g, 29.8 mmol [WO 0031062]) in tetrahydrofuran (50 mL). The mixture was warmed to ambient temperature and allowed to stir three hours followed by treatment with water, saturated aqueous ammonium chloride, and extraction with ethyl acetate. The combined organic layers were dried over sodium sulfate, filtered and the solvent removed under reduced pressure. The resulting residue was purified by silica gel column chromatography, eluting with hexane-:ethyl acetate (1:4) to obtain 1.96 g of the title compound as a 1:1 mixture of isomers.

1$^{st}$ Isomer: $^1$H NMR (400 MHz, CDCl$_3$) δ 7.88 (s, 1H), 7.40–7.21 (m, 6H), 5.50 (q, 1H), 4.18–4.10 (m, 1H), 3.66–3.62 (m, 1H), 3.35–3.28 (m, 1H), 2.95–2.75 (m, 2H), 1.52 (d, 3H).

2$^{nd}$ Isomer: $^1$H NMR (400 MHz, CDCl$_3$) δ 7.85 (s, 1H), 7.40–7.21 (m, 6H), 5.50 (q, 1H), 4.30–4.20 (m, 1H), 3.78–3.67 (m, 1H), 3.29–3.18 (m, 1H), 2.95–2.75 (m, 2H), 1.55 (d, 3H).

EXAMPLE 6B2

4-(Benzyloxyiminooxazol-4-ylmethyl)-1-((S)-1-phenylethyl)pyrrolidin-2-one

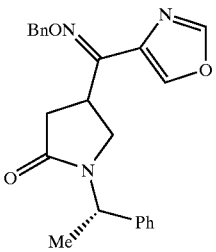

4-(Oxazole-4-carbonyl-1-((S)-1-phenylethyl)pyrrolidin-2-one (0.5 g, 1.76 mmol) [Example 6B1] and O-benzylhydroxylamine, hydrochloride (0.42 g, 2.64 mmol) in pyridine (5 mL) were refluxed for five hours and then cooled to room temperature. The reaction mixture was diluted with water, washed with saturated sodium bicarbonate and extracted with ethyl acetate. The combined organic layers were dried over sodium sulfate, filtered and concentrated under reduced pressure. The resulting residue was purified by silica gel column chromatography eluting with a mixture of 1:2 mixture of hexanes:ethyl acetate to provide 0.41 g of the title compound. $^1$H NMR (400 MHz, CDCl$_3$) δ 7.75–7.60 (m, 1H), 7.40–7.12 (m, 11H), 5.60–5.45 (m, 1H), 5.35–5.23 (m, 1H), 5.20–5.08 (m, 1H), 4.30–4.16 (m, 1H), 3.88–2.60 (m, 4H), 1.50–1.30 (m, 3H).

EXAMPLE 6B3

C-Oxazol-4-yl-C-[1-((S)-phenylethyl)pyrrolidin-3-yl]methylamine

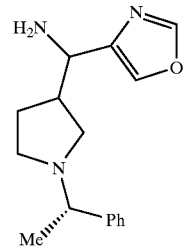

To a cooled solution (0° C.) of 4-(benzyloxyiminooxazol-4-ylmethyl)-1-((S)-1-phenylethyl)pyrrolidin-2-one (3.16 g, 8.11 mmol) [Example 6B2] in tetrahydrofuran (80 mL) was added borane tetrahydrofuran complex (1M, 24 mL). The mixture was warmed to room temperature and stirred for 21 hours. The mixture was concentrated, and the residue was mixed with water (5 mL) and extracted with chloroform. The combined organic extracts were concentrated under reduced pressure, dissolved in 80% aqueous ethanol, treated with triethylamine (20 mL) and then heated under reflux for two hours. The solvent was evaporated, and the residue was extracted with dichloromethane. The combined extracts were then dried over sodium sulfate and the solvent removed in vacuo. The resulting residue was purified by silica gel column chromatography, eluting with 9:1 chloroform-:methanol to give the title compound. (2.5 g). $^1$H NMR (400

MHz, CDCl₃) δ 7.55 (s, 1H), 7.40–7.15 (m, 5H), 7.05 (s, 1H), 4.02–3.88 (m, 1H), 3.25–3.10 (m, 1H), 2.90–2.20 (m, 5H), 2.00–1.50 (m, 4H), 1.35 (m, 3H).

EXAMPLE 6B4

C-Oxazol-4-yl-C-pyrrolidin-3-ylmethylamine

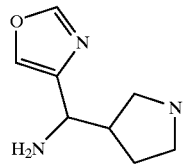

To the solution of C-Oxazol-4-yl-C-[1-((S)-phenylethyl)pyrrolidin-3-yl]methylamine (2.44 g, 8.99 mmol) [example 6B3] and ammonium formate (2.83 g, 44.9 mmol) in methanol (45 mL), was added portionwise 10% palladium/carbon catalyst under a nitrogen atmosphere. The mixture was then refluxed for five hours and filtered through a pad of Celite and washed with methanol. The combined organics were concentrated under reduced pressure to obtain the title compound (0.9 g). ¹H NMR (400 MHz, CDCl₃) δ 7.66 (s, 1H), 7.11 (s, 1H), 5.60–4.50 (bs, 3H) 4.18–4.10 (m, 1H), 3.60–3.25 (m, 3H), 3.08–2.80 (m, 2H), 2.30–1.80 (m, 2H).

EXAMPLE 7

4-tert-Butoxy-2,5-difluoro-3-methoxypyridine

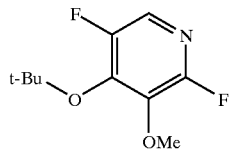

A mixture of 4-tert-butoxy-2,3,6-trifluoro-5-methoxypyridine (1.5 g. 6.4 mmol) and hydrazine monohydrate (1.7 mL, 34 mmol [Qun Li et al. *J. Med. Chem.* 1996, 39(16), 3070–3088]) in n-propanol (10 mL) was heated to reflux for 3 hours. The solvent was removed in vacuo and the residue was dissolved in dichlromethane, washed with water and concentrated to afford crude (4-tert-butoxy-3,6-difluoro-5-methoxypyridin-2-yl)hydrazine (1.4 g, 90%). 1.2 g of the material was redissolved in methanol (12 mL) and 20% aqueous sodium hydroxide (2.5 mL). Oxygen was passed through the solution with vigorous stirring for 20 hours. The deep blue solution was diluted with water (12 mL) and extracted with hexane (2×30 mL). The combined organics were washed with brine, dried over sodium sulfate and concentrated in vacuo. The residue was purified by column chromatography, eluting with ethyl acetate/hexane (1:16) to afford the title compound (0.9 g). ¹H NMR (400 MHz, CDCl₃) δ 7.74 (m, 1H), 3.93 (m, 3H), 1.41 (s, 9H). MSCI: m/z=218 (MH⁺).

EXAMPLE 8

(4-tert-Butoxy-5-fluoro-3-methoxypyridin-2-yl)cyclopropylacetonitrile

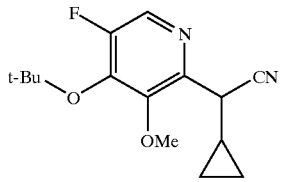

A −78° C. solution of diisopropylamine (1.3 mL, 9.0 mmol), under a nitrogen atmosphere in dry tetrahydrofuran (20 mL), was treated dropwise with 2.5 N n-butyllithium (3.6 mL, 9.0 mmol) and stirred for 10 minutes. The solution was treated dropwise with cyclopropylacetonitrile (0.8 g, 3.5 mmol) and stirred at −78° C. for 15 minutes. A solution of 4-tert-butoxy-2,5-difluoro-3-methoxypyridine (0.8 g, 3.5 mmol)[Example 7] in dry tetrahydrofuran (5 mL) was added and stirred for 1 hour at −78° C. followed by 1 hour at 0° C. The mixture was quenched with saturated ammonium chloride and extracted with diethylether. The combined extracts were washed with brine, dried over sodium sulfate, and the solvent removed in vacuo. The residue was purified by column chromatography, eluting with ethyl acetate/hexanes (1:4) to afford the title compound (0.9 g). ¹H NMR (400 MHz, CDCl₃) δ 8.22 (s, 1H), 3.98 (s, 3H), 3.77 (d, 1H), 1.55–1.48 (m, 1H), 1.42 (s, 9H), 0.62–0.54 (m, 2H), 0.50–0.42 (m, 1H), 0.35–0.30 (m, 1H). MSCI: m/z=279 (MH⁺).

EXAMPLE 9

(4-Chloro-5-fluoro-3-methoxypyridin-2-yl)cyclopropylacetonitrile

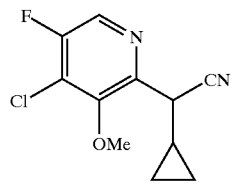

A solution of (4-tert-butoxy-5-fluoro-3-methoxypyridin-2-yl)cyclopropylacetonitrile (0.9 g, 3 mmol) [Example 8] and trifluoroacetic acid (2 mL) in dichloromethane was stirred at room temperature for 25 minutes. The solvent was removed in vacuo and the oily residue dissolved in 15 mL of dichloromethane and 2 mL of dimethylformamide. The resulting solution was cooled in an ice-bath and treated dropwise with phosphoryl chloride (2.4 mL). The solution was allowed to warm to ambient temperature and stirred overnight. The mixture was then poured onto ice and extracted with dichloromethane (2×20 mL). The combined extracts were washed with water, saturated sodium bicarbonate, water, dried over sodium sulfate, and concentrated in vacuo. The residue was purified by column chromatography, eluting with ethyl acetate/hexane (1:4) to provide the title compound (0.4 g, 60%). ¹H NMR (400 MHz, CDCl₃) δ 8.32 (s. 1H), 4.05 (s, 3H), 3.77 (d, 1H), 1.58–1.49 (m 1H), 0.80–0.71 (m, 1H), 0.68–0.55 (m, 2H), 0.52–0.43 (m, 1H). MSCI: m/z=241 (MH⁺).

EXAMPLE 10

(4-Chloro-5-fluoro-3-methoxypyridin-2-yl)-2-cyclopropylacetamide

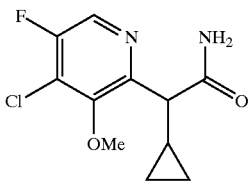

The title compound (0.88 g) was prepared from (4-chloro-5-fluoro-3-methoxypyridin-2-yl)cyclopropylacetonitrile (1.0 g, 4.15 mmol)[Example 9] using the procedure used to prepare Example 1. $^1$H NMR (400 MHz, CDCl$_3$) δ 8.33 (s, 1H), 6.89 (bs, 1H), 5.66 (bs, 1H), 3.94 (s, 3H), 3.26 (d, 1H), 1.46–1.43 (m, 1H), 0.81–0.70 (m, 1H), 0.60–0.44 (m, 2H), 0.31–0.22 (m, 1H). MSCI: m/z=259 (MH$^+$).

EXAMPLE 11

6-Chloro-4-cyclopropyl-7-fluoro-5-methoxypyrido[1,2-c]pyrimidine-1,3-dione

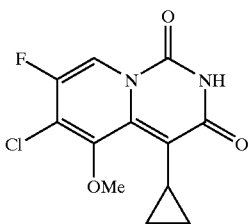

The title compound (0.15 g) was prepared from (4-chloro-5-fluoro-3-methoxypyridin-2-yl)cyclopropylacetamide (0.88 g, 3.40 mmol [Example 10]) and triphosgene (2.10 g, 7.20 mmol) using a similar procedure to that of Example 2. $^1$H NMR (400 MHz, CDCl$_3$) δ 9.12 (bs, 1H), 8.13 (d, 1H), 3.82 (s, 3H), 1.33–1.24 (m, 1H), 1.05–0.98 (m, 2H), 0.71–0.60 (m, 2H). MSCI: m/z 285 (MH$^+$).

EXAMPLE 12

2-Amino-6-chloro-4-cyclopropyl-7-fluoro-5-methoxypyrido[1,2-c]pyrimidine-1,3-dione

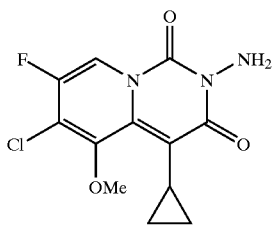

The title compound (0.09 g) was prepared from 6-chloro-4-cyclopropyl-7-fluoro-5-methoxypyrido[1,2-c]pyrimidine-1,3-dione (0.12 g, 0.42 mmol [Example 11]) and 2,4-dinitrophenylhydroxylamine (0.11 g, 0.5 mmol) using the procedure used to prepare Example 3. $^1$H NMR (400 MHz, CDCl$_3$) δ 8.17 (d, 1H), 5.52 (bs, 2H), 3.84 (s, 3H), 1.90–1.82 (m, 1H), 1.07–1.00 (m, 2H), 0.62–0.55 (m, 2H). MSCI: m/z 300 (MH$^+$).

EXAMPLE 13

2-Amino-4-cyclopropyl-7-fluoro-5-methoxy-6-[(R)-3-((S)-1-methylaminoethyl)pyrrolidin-1-yl]pyrido[1,2-c]pyrimidine-1,3-dione

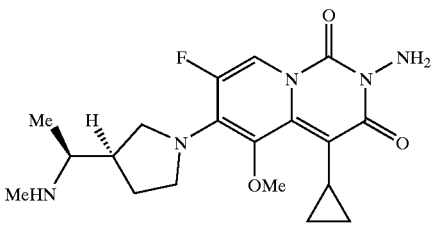

The title compound (0.04 g) was prepared from 2-amino-6-chloro-4-cyclopropyl-7-fluoro-5-methoxypyrido[1,2-c]pyrimidine-1,3-dione (0.09 g, 0.30 mmol [Example 12]), and methyl-((S)—(R)-1-pyrrolidin-3-ylethyl)amine (0.11 g, 0.90 mmol) using the general procedure of Example 4. $^1$H NMR (400 MHz, CDCl$_3$) δ 8.20 (d, 1H), 5.42 (s, 2H), 3.89–3.58 (m, 5H), 3.22 (s, 3H), 2.67–2.58 (m, 1H), 2.46 (s, 3H), 2.22–2.02 (m, 2H), 1.80–1.61 (m, 2H), 1.21 (d, 3H), 1.10–1.00 (m, 1H), 0.84–0.76 (m, 1H), 0.52–0.44 (m, 1H), 0.40–0.32 (m, 1H). MSCI: m/z=392 (MH$^+$).

EXAMPLE 14

1-Benzyl-3-(2-bromoacetyl)pyrrolidin-2-one

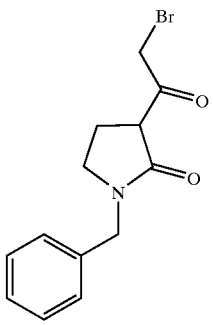

To a solution of 1-benzyl-2-oxopyrrolidine-3-carboxylic acid (10 g, 45.7 mmol [U.S. Pat. No. 5,175,157]) in tetrahydrofuran/dioxane (300 mL/60 mL) at −10° C. was added 4-methylmorpholine (6.5 mL, 59.4 mmol) followed by isobutyl chloroformate (7.10 mL, 54.8 mmol). After 10 minutes, a white precipitate was filtered off and washed with tetrahydrofuran. The filtrate and wash were poured into an Erlenmyer flask and kept at 0° C. To this mixture was added a solution of diazomethane (1.1M in ether, 55 mL). After 15 minutes, a 1:1 hydrobromic acid (48%)/acetic acid solution was added dropwise until gas evolution ceased. After 15 minutes, the reaction mixture was diluted with ethyl acetate and washed with saturated aqueous sodium bicarbonate. The combined organic layers were dried over magnesium sulfate, filtered and concentrated. The crude reaction mixture was then purified by chromatography (99:1 dichloromethane/methanol) to give the title compound (26.6 g). MSCI: m/z=(MH$^+$) 296,298.

EXAMPLE 15

1-Benzyl-3-(2-fluoroacetyl)pyrrolidin-2-one

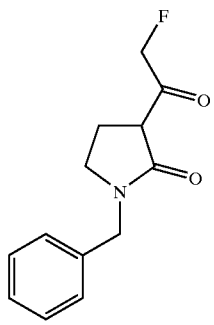

To a solution of 1-benzyl-3-(2-bromoacetyl)pyrrolidin-2-one (2.2 g, 7.43 mmol, Example 14) in acetonitrile (25 mL) was added 18-crown-6 (0.980 g, 3.72 mmol) and potassium fluoride (spray dried) (2.16 g, 37.2 mmol). The reaction mixture was immersed in an oil bath at 80° C. After 1 hour, the mixture was cooled to room temperature and partitioned between water and ethyl acetate. The organic layer was dried over magnesium sulfate, filtered and concentrated. The crude residue was then purified by chromatography (99:1 dichloromethane/methanol then 98:2 dichloromethane/methanol) to afford the title compound (0.515 g): $^1$H NMR (CDCl$_3$) δ 7.36–7.19 (m, 5H), 4.93 (m, 2H), 4.46 (m, 2H), 3.61 (m, 1H), 3.48 (m, 2H), 2.74 (m, 2H).

EXAMPLE 16

1-Benzyl-3-(1-benzylamino-2-fluoroethyl)pyrrolidin-2-one

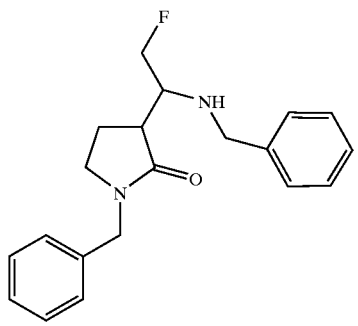

Benzylamine (3.9 mL, 35.7 mmol) was added to a solution of 1-benzyl-3-(2-fluoro-acetyl)pyrrolidin-2-one (7.00 g, 29.8 mmol, Example 15) in dichloroethane (150 mL). The solution was cooled to 0° C. and sodium triacetoxyborohydride (8.20 g, 38.7 mmol) added. The reaction mixture was warmed to room temperature and stirred overnight, then washed with aqueous sodium bicarbonate solution and brine. The organic layer was then dried over magnesium sulfate, filtered and concentrated. The residue was purified by chromatography (99:1 to 97:3 dichloromethane/methanol) to afford the title compound (7.2 g) as a mixture of diastereomers. MSCI: m/z 327 (MH$^+$).

EXAMPLE 17

Benzyl[1-(1-benzylpyrrolidin-3-yl)-2-fluoroethyl]amine

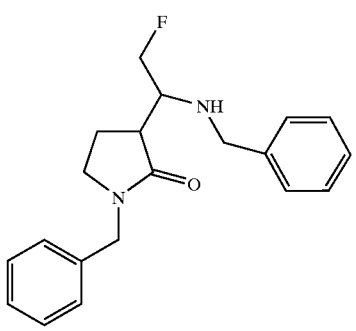

To a solution of 1-benzyl-3-(1-benzylamino-2-fluoroethyl)pyrrolidin-2-one (7.2 g, 22 mmol, Example 16) in tetrahydrofuran (100 mL) at 0° C. was added lithium aluminum hydride (1M in tetrahydrofuran, 22 mL) dropwise. After 1 hour, the mixture was warmed to room temperature and then quenched after 30 minutes with 0.84 mL water, 0.84 mL 15% sodium hydroxide solution and 2.5 mL water. The reaction mixture was then filtered and concentrated. The crude residue was purified by chromatography (97:3 to 90:10 dichloromethane/methanol) to give the title compound (2.5 g) as a mixture of diastereomers. MSCI: m/z=313 (MH$^+$).

EXAMPLE 18

2-Fluoro-1-pyrrolidin-3-ylethylamine

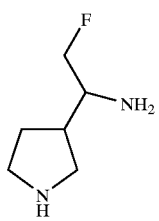

To a solution of benzyl[1-(1-benzylpyrrolidin-3-yl)-2-fluoroethyl]amine (2.5 g, 8.0 mmol, Example 17) in methanol (50 mL) was added 20% palladium on carbon (200 mg). Hydrogen was introduced to the reaction mixture at high pressure (48 psi) for 24 hours, at which time sulfuric acid (3 drops) was added. After an additional 24 hours, the reaction mixture was filtered through Celite, washed with methanol, and the combined filtrates concentrated under vacuum to afford the title compound (1.0 g): MSCI: m/z 133 (MH$^+$).

EXAMPLE 19

The following illustrates representative pharmaceutical dosage forms, containing a compound of Formula I (Compound 4f), for therapeutic or prophylactic use in humans.

| (i) | Tablet | mg/tablet |
|---|---|---|
| | 'Compound 4f' | 25.0 |
| | Lactose | 50.0 |
| | Corn Starch (for mix) | 10.0 |
| | Corn Starch (paste) | 10.0 |
| | Magnesium Stearate (1%) | 3.0 |
| | | 300.0 |

The biphenylsulfonamide, lactose, and corn starch (for mix) are blended to uniformity. The corn starch (for paste) is suspended in 200 mL of water and heated with stirring to form a paste. The paste is used to granulate the mixed powders. The wet granules are passed through a No. 8 hand screen and dried at 80° C. The dry granules are lubricated with the 1% magnesium stearate and pressed into a tablet. Such tablets can be administered to a human from one to four times a day for treatment of pathogenic bacterial infections.

| (ii) | Tablet | mg/capsule |
|---|---|---|
| | 'Compound 4f' | 10.0 |
| | Colloidal Silicon Dioxide | 1.5 |
| | Lactose | 465.5 |
| | Pregelatinized Starch | 120.0 |
| | Magnesium Stearate (1%) | 3.0 |
| | | 600.0 |

| (iii) | Preparation for Oral Solution | Amount | |
|---|---|---|---|
| | 'Compound 4f' | 400 | mg |
| | Sorbitol Soluition (70% N.F.) | 40 | mL |
| | Sodium Benzoate | 20 | mg |
| | Saccharin | 5 | mg |
| | Cherry Flavor | 20 | mg |
| | Distilled Water q.s. | 100 | mL |

The sorbitol solution is added to 40 mL of distilled water, and the biphenylsulfonamide is dissolved therein. The saccharin, sodium benzoate, flavor, and dye are added and dissolved. The volume is adjusted to 100 mL with distilled water. Each milliliter of syrup contains 4 mg of invention compound.

(iv) Parenteral Solution

In a solution of 700 mL of propylene glycol and 200 mL of water for injection is suspended 20 g of 2-Amino-4-cyclopropyl-7-fluoro-5-methyl-6-[3-(1-methylamino-ethyl)-pyrrolidin-1-yl]-pyrido[1,2-c]pyrimidine-1,3-dione (Compound 4f). After suspension is complete, the pH is adjusted to 6.5 with 1 N hydrochloric acid, and the volume is made up to 1000 mL with water for injection. The Formulation is sterilized, filled into 5.0 mL ampoules each containing 2.0 mL, and sealed under nitrogen.

| (v) | Injection 1 (1 mg/mL) | Amount |
|---|---|---|
| | 'Compound 4f' | 1.0 |
| | Dibasic Sodium Phosphate | 12.0 |
| | Monobasic Sodium Phosphate | 0.7 |
| | Sodium Chloride | 4.5 |
| | 1.0 N Sodium hydroxide solution (pH adjustment to 7.0–7.5) | q.s. |
| | Water for injection | q.s. ad 1 mL |

-continued

| (vi) | Injection 2 (10 mg/mL) | Amount |
|---|---|---|
| | 'Compound 4f' | 10.0 |
| | Dibasic Sodium Phosphate | 1.1 |
| | Monobasic Sodium Phosphate | 0.3 |
| | Polyethylene glyco 400 | 200.0 |
| | 0.1 N hydrochloric acid solution (pH adjustment to 7.0–7.5) | q.s. |
| | Water for injection | q.s. ad 1 mL |

| (vii) | Injection 2 (10 mg/mL) | Amount |
|---|---|---|
| | 'Compound 4f' | 20.0 |
| | Oleic Acid | 10.0 |
| | Trichloromonofluoromethane | 5,000.0 |
| | Dichlorodifluoromethane | 10,000.0 |
| | Dichlorotetrafluoroethane | 5,000.0. |

All patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of Formula I:

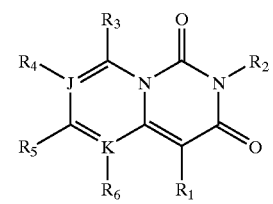

I or a pharmaceutically acceptable salt thereof wherein:

$R_1$ is H, $C_1$–$C_7$ alkyl and substituted alkyl, $C_2$–$C_7$ alkenyl and substituted alkenyl, $C_2$–$C_7$ alkynyl and substituted alkynyl, $C_3$–$C_7$ cycloalkyl and substituted cycloalkyl, aryl and substituted aryl, heterocyclic and substituted heterocyclic, or heteroaryl and substituted heteroaryl;

$R_2$ is H, $C_1$–$C_7$ alkyl and substituted alkyl, $C_2$–$C_7$ alkenyl and substituted alkenyl, $C_2$–$C_7$ alkynyl and substituted alkynyl, $C_3$–$C_7$ cycloalkyl and substituted cycloalkyl, aryl and substituted aryl, heterocyclic and substituted heterocyclic, heteroaryl and substituted heteroaryl, halo, $NO_2$,

NO,

CN, $OR_a$,

wherein $R_a$ is H, $C_1$–$C_7$ alkyl and substituted alkyl, $C_2$–$C_7$ alkenyl and substituted alkenyl,
$C_3$–$C_7$ cycloalkyl and substituted cycloalkyl,
aryl and substituted aryl,
heteroaryl and substituted heteroaryl,
heterocycloalkyl and substituted heterocycloalkyl,

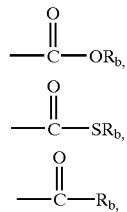

wherein $R_b$ is H,
$C_1$–$C_7$ alkyl and substituted alkyl,
$C_2$–$C_7$ alkenyl and substituted alkenyl,
$C_3$–$C_7$ cycloalkyl and substituted cycloalkyl,
aryl and substituted aryl,
heteroaryl and substituted heteroaryl,
heterocycloalkyl and substituted heterocycloalkyl;

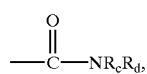

wherein $R_c$ and $R_d$ are independantly H,
$C_1$–$C_7$ alkyl and substituted alkyl,
$C_2$–$C_7$ alkenyl and substituted alkenyl,
$C_3$–$C_7$ cycloalkyl and substituted cycloalkyl,
aryl and substituted aryl,
heteroaryl and substituted heteroaryl,
heterocycloalkyl and substituted heterocycloalkyl;
$NR_eR_f$, wherein
$R_e$ and $R_f$ are each independently H,
$C_1$–$C_7$ alkyl and substituted alkyl,
$C_2$–$C_7$ alkenyl and substituted alkenyl,
$C_2$–$C_7$ alkynyl and substituted alkynyl,
$C_3$–$C_7$ cycloalkyl and substituted cycloalkyl,
$C_5$–$C_8$ cycloalkenyl and substituted cycloalkenyl,
aryl and substituted aryl, or

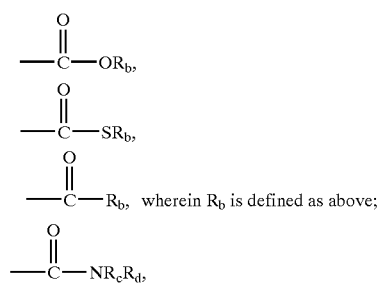

wherein $R_c$ and $R_d$ are defined as above;
aryl and substituted aryl,
heteroaryl and substituted heteroaryl,
heterocycloalkyl and substituted heterocycloalkyl, or
$R_e$ and $R_f$ are taken together with the nitrogen to which they are attached form a 4, 5, 6, 7, or 8 membered ring having from 0 to 3 heteroatoms selected from N, O, and S, wherein said ring is optionally substituted by one or more substituents;

$R_3$, $R_4$, and $R_6$ independently are H,
OH,
$(O)_nC_1$–$C_7$ alkyl and substituted alkyl,
$(O)_nC_2$–$C_7$ alkenyl and substituted alkenyl,
$(O)_nC_2$–$C_7$ alkynyl and substituted alkynyl,
wherein n is 0 or 1,
halo,
$NO_2$,
CN,
$NR_eR_f$, wherein $R_e$ and $R_f$ are defined as above;
$R_5$ is
$C_2$–$C_7$ alkenyl and substituted alkenyl,
$C_2$–$C_7$ alkynyl and substituted alkynyl,
$OR_a$, wherein $R_a$ is defined as above,

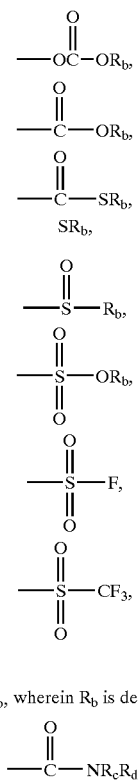

wherein $R_c$ and $R_d$ are defined as above;
halo,
$NO_2$,
CN,
$NR_eR_f$, wherein $R_e$ and $R_f$ are defined as above;
aryl or fused aryl,
heterocyclic or fused heterocyclic,
heteroaryl or fused heteroaryl, or
bicyclic heterocyclic or spiro heterocyclic,
wherein fused aryl, fused heterocyclic, fused heteroaryl, bicyclic heterocyclic, or spiro heterocyclic can be substituted.

2. The compound of claim 1, wherein $R_5$ is:

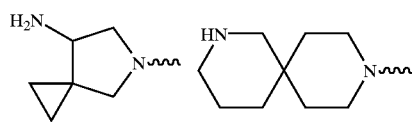

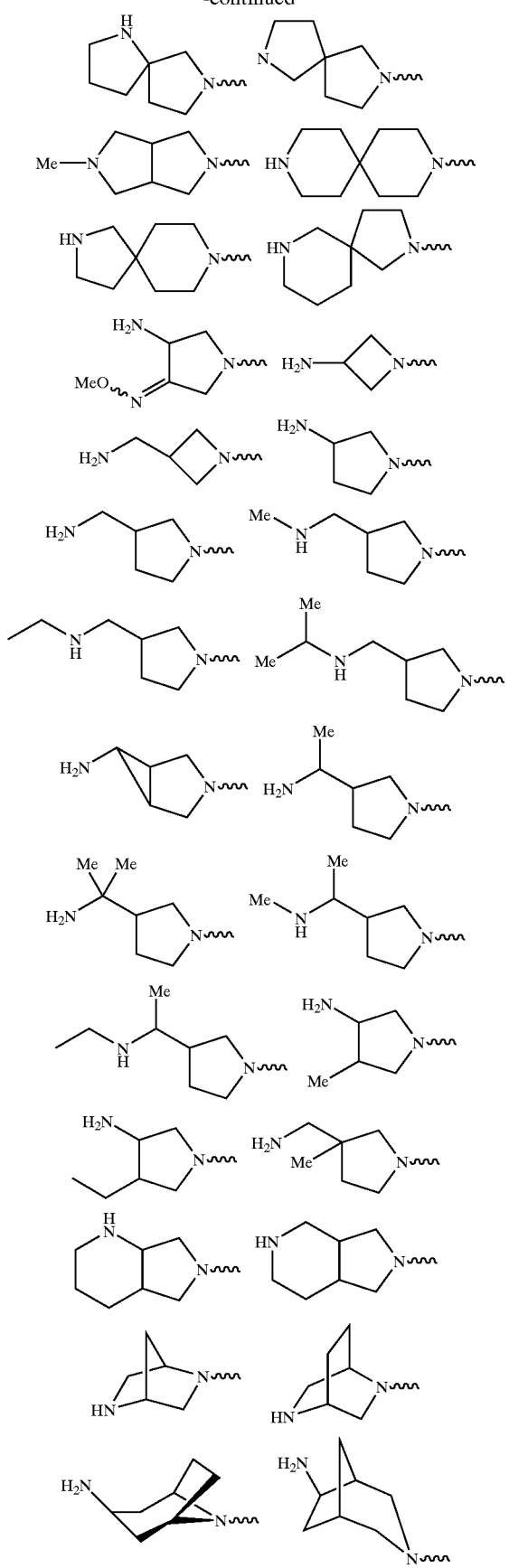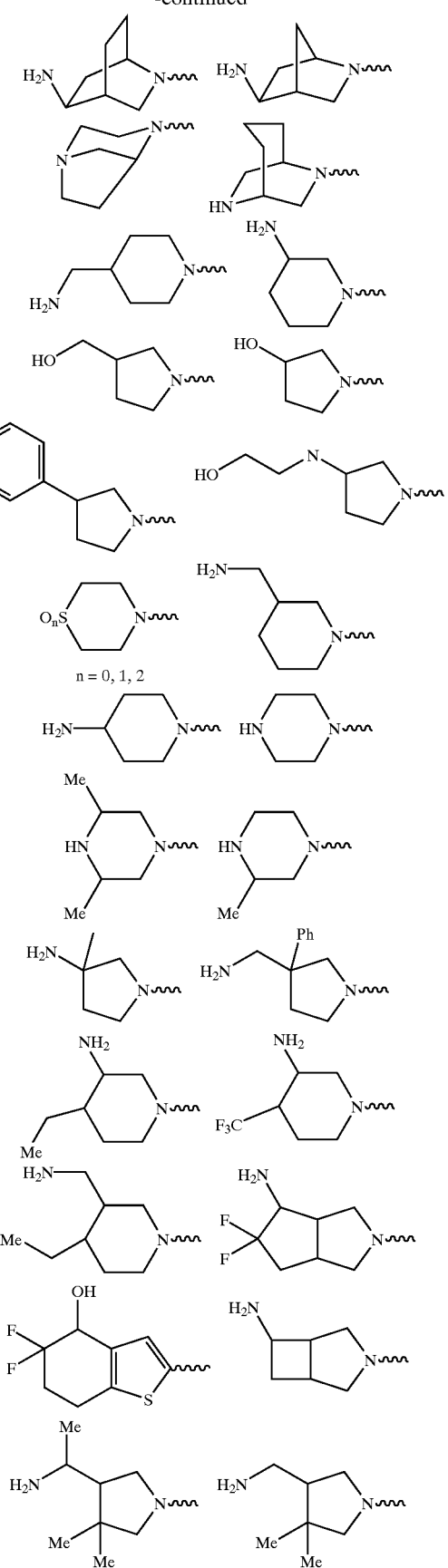

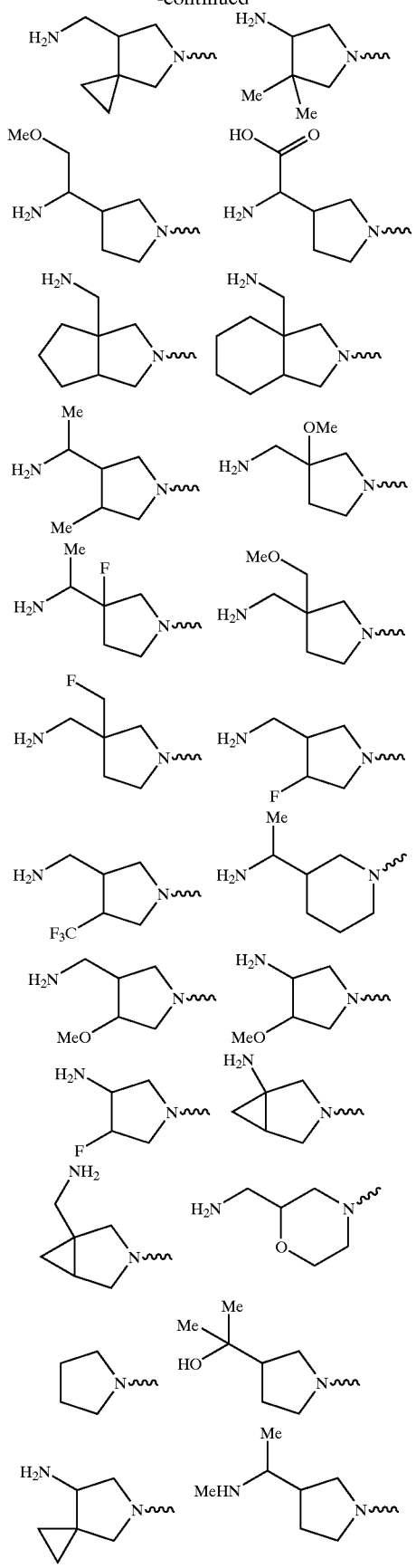
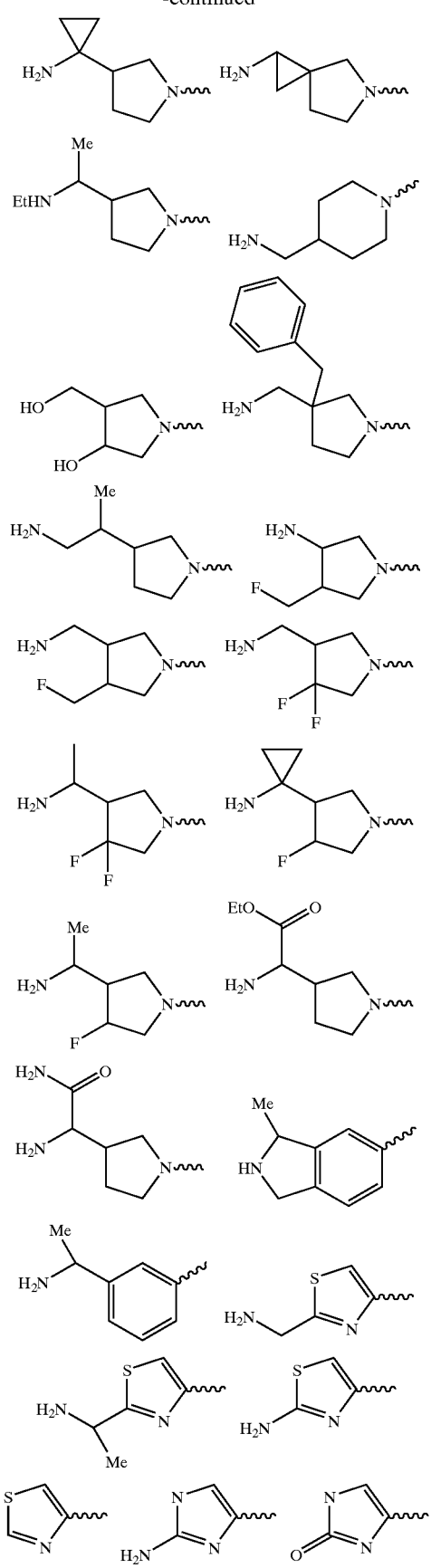

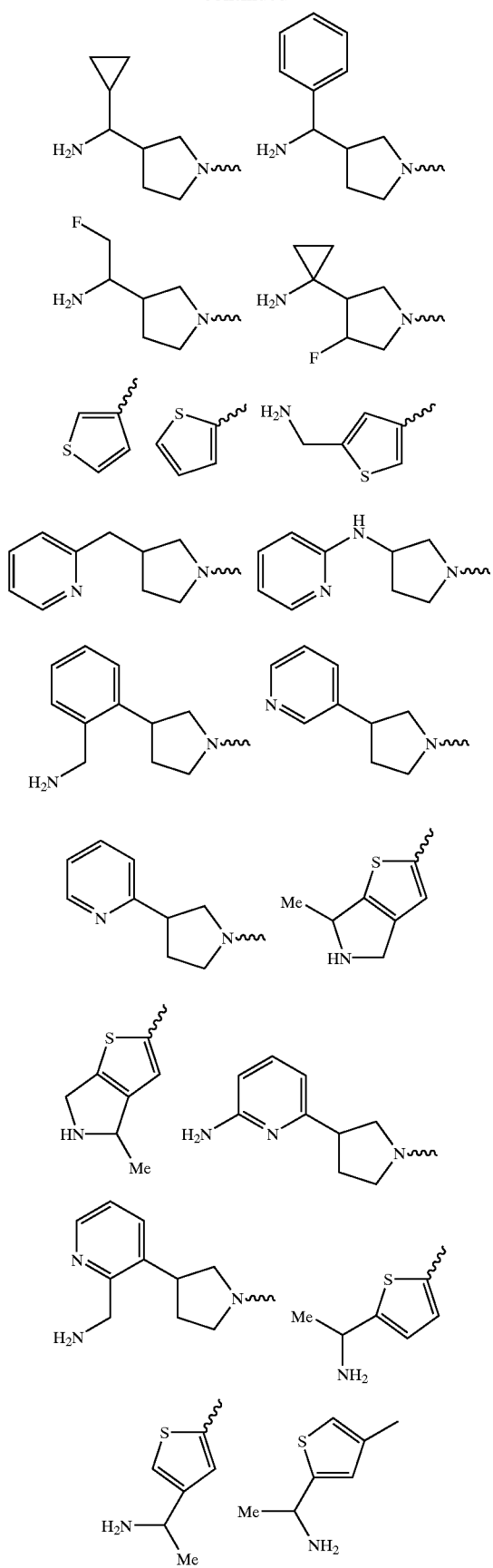

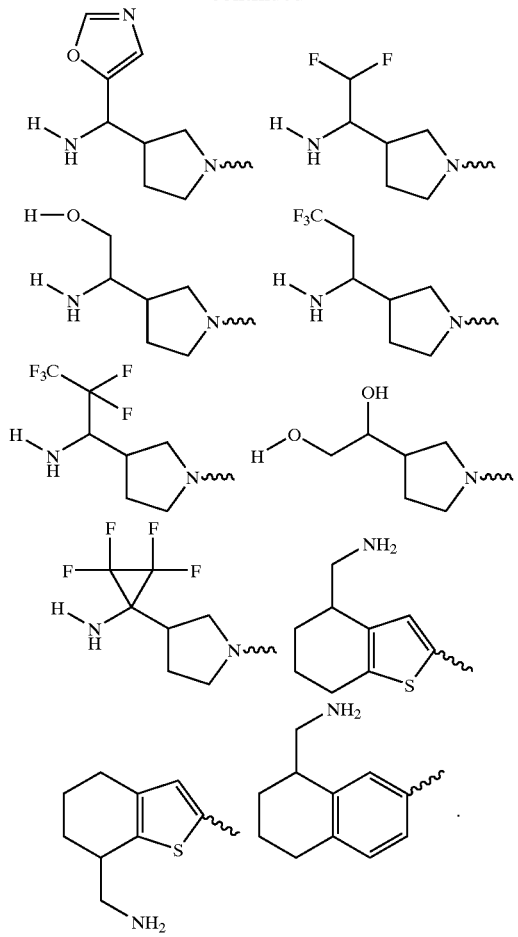

3. The compound of claim 1, wherein:
$R_1$ is methyl, ethyl, cyclopropyl, t-butyl, 2-fluorocyclopropyl;
$R_2$ is H, OH, or $NH_2$;
$R_3$ is H;
$R_4$ is F or Cl;
$R_5$ is 1-pyrrolidinyl or substituted 1-pyrrolidinyl, 1-piperidinyl or substituted 1-piperidinyl, 1-piperizinyl or substituted 1-piperizinyl, or

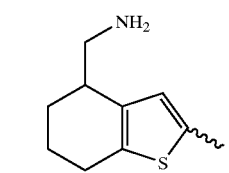

;

and
$R_6$ is F, Cl, methyl, methoxy, $OCF_3$, $OCHF_2$, $OCH_2F$, $OCH_2CF_3$, $OCH_2CHF_2$, or $OCH_2CH_2F$.

4. The compound of claim 2, wherein:
$R_1$ is cyclopropyl;
$R_2$ is H or $NH_2$;
$R_3$ is H;

$R_4$ is F;

$R_5$ is 1-pyrrolidinyl or substituted 1-pyrrolidinyl, 1-piperidinyl or substituted 1-piperidinyl; and $R_6$ is methyl, methoxy, $OCF_3$, $OCHF_2$, $OCH_2F$, $OCH_2CF_3$, $OCH_2CHF_2$, or $OCH_2CH_2F$.

5. The compound of claim 2, wherein:

$R_1$ is cyclopropyl;

$R_2$ is H or $NH_2$;

$R_3$ is H;

$R_4$ is F;

$R_5$ is 1-pyrrolidinyl or substituted 1-pyrrolidinyl, 1-piperidinyl or substituted 1-piperidinyl, or 1-piperizinyl or substituted 1-piperizinyl; and $R_6$ is methyl, methoxy, $OCF_3$, $OCHF_2$, $OCH_2F$, $OCH_2CF_3$, $OCH_2CHF_2$.

6. The compound of claim 2, wherein:

$R_1$ is cyclopropyl;

$R_2$ is H or $NH_2$;

$R_3$ is H; $R_4$ is F;

$R_5$ is 1-pyrrolidinyl or substituted 1-pyrrolidinyl, or 1-piperidinyl or substituted 1-piperidinyl, and $R_6$ is methyl, methoxy, $OCF_3$, $OCHF_2$, $OCH_2F$, or $OCH_2CF_3$.

7. The compound of claim 2, wherein:

$R_1$ is cyclopropyl;
  2-fluorocyclopropyl,
  1- or 2-methylcyclopropyl, or cyclopropylmethyl;

$R_2$ is $NH_2$ OH, or H;

$R_3$ is H;

$R_4$ is F or Cl;

$R_5$ is 1-pyrrolidinyl or substituted 1-pyrrolidinyl, 1-piperidinyl or substituted 1-piperidinyl, or 1-piperizinyl or substituted 1-piperizinyl;

$R_6$ is H,
  $C_1$–$C_4$ alkyl substituted alkyl,
  OH,
  F,
  Cl, or
  —O—$C_1$–$C_4$ alkyl and substituted —O—$C_1$–$C_4$ alkyl.

8. The compound of claim 1, which is:

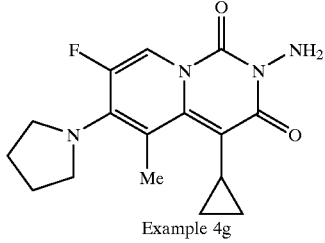

Example 4g

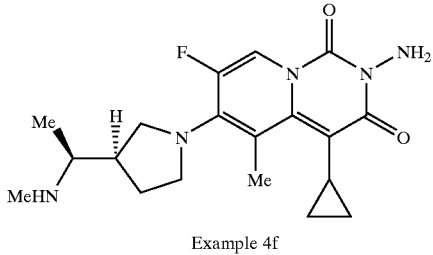

Example 4f

-continued

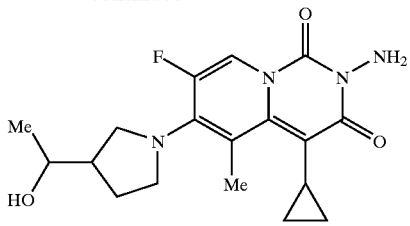

Example 4h

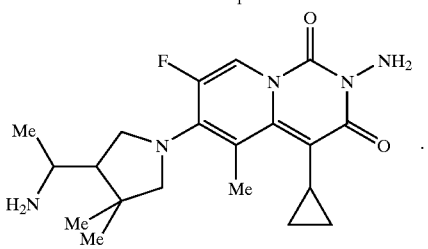

Example 5c

9. A compound of Formula VI:

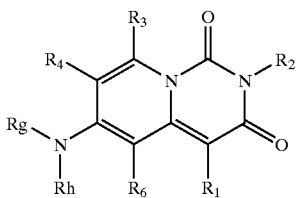

VI or a pharmaceutically acceptable salt thereof wherein:

$R_1$ is H,
  $C_1$–$C_7$ alkyl and substituted alkyl,
  $C_2$–$C_7$ alkenyl and substituted alkenyl,
  $C_2$–$C_7$ alkynyl and substituted alkynyl,
  $C_3$–$C_7$ cycloalkyl and substituted cycloalkyl,
  aryl and substituted aryl,
  heterocyclic and substituted heterocyclic,
  or heteroaryl and substituted heteroaryl;

$R_2$ is H,
  $C_1$–$C_7$ alkyl and substituted alkyl,
  $C_2$–$C_7$ alkenyl and substituted alkenyl,
  $C_2$–$C_7$ alkynyl and substituted alkynyl,
  $C_3$–$C_7$ cycloalkyl and substituted cycloalkyl,
  aryl and substituted aryl,
  heterocyclic and substituted heterocyclic,
  heteroaryl and substituted heteroaryl,
  halo,
  $NO_2$,
  NO,
  CN,
  $OR_a$,

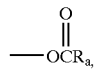

wherein $R_a$ is H,
  $C_1$–$C_7$ alkyl and substituted alkyl,
  $C_2$–$C_7$ alkenyl and substituted alkenyl,
  $C_3$–$C_7$ cycloalkyl and substituted cycloalkyl,
  aryl and substituted aryl, heteroaryl and substituted heteroaryl,
heterocycloalkyl and substituted heterocycloalkyl,

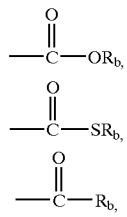

wherein $R_b$ is H,
$C_1$–$C_7$ alkyl and substituted alkyl,
$C_2$–$C_7$ alkenyl and substituted alkenyl,
$C_3$–$C_7$ cycloalkyl and substituted cycloalkyl,
aryl and substituted aryl,
heteroaryl and substituted heteroaryl,
heterocycloalkyl and substituted heterocycloalkyl;

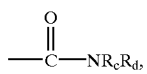

wherein $R_c$ and $R_d$ are independantly H,
$C_1$–$C_7$ alkyl and substituted alkyl,
$C_2$–$C_7$ alkenyl and substituted alkenyl,
$C_3$–$C_7$ cycloalkyl and substituted cycloalkyl,
aryl and substituted aryl,
heteroaryl and substituted heteroaryl,
heterocycloalkyl and substituted heterocycloalkyl;
$NR_eR_f$, wherein
$R_e$ and $R_f$ are each independently H,
$C_1$–$C_7$ alkyl and substituted alkyl,
$C_2$–$C_7$ alkenyl and substituted alkenyl,
$C_2$–$C_7$ alkynyl and substituted alkynyl,
$C_3$–$C_7$ cycloalkyl and substituted cycloalkyl,
$C_5$–$C_8$ cycloalkenyl and substituted cycloalkenyl,
aryl and substituted aryl, or

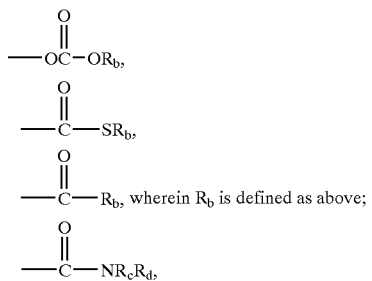

wherein $R_c$ and $R_d$ are defined as above;
aryl and substituted aryl,
heteroaryl and substituted heteroaryl,
heterocycloalkyl and substituted heterocycloalkyl, or
$R_e$ and $R_f$ are taken together with the nitrogen to which they are attached form a 4, 5, 6, 7, or 8 membered ring having from 0 to 3 heteroatoms selected from N, O, and S, wherein said ring is optionally substituted by one or more substituents;
$R_3$, $R_4$, and $R_6$ independently are H,
OH,
$(O)_nC_1$–$C_7$ alkyl and substituted alkyl,
$(O)_nC_2$–$C_7$ alkenyl and substituted alkenyl,
$(O)_nC_2$–$C_7$ alkynyl and substituted alkynyl, wherein n is 0 or 1,
halo,
$NO_2$,
CN,
$NR_eR_f$, wherein $R_e$ and $R_f$ are defined as above; and
$R_g$ and $R_h$ are defined as for $R_e$ and $R_f$ above.

10. The compound of claim 9, wherein $R_g$ and $R_h$, together with the nitrogen to which they are attached, form any of the ring systems as shown below:

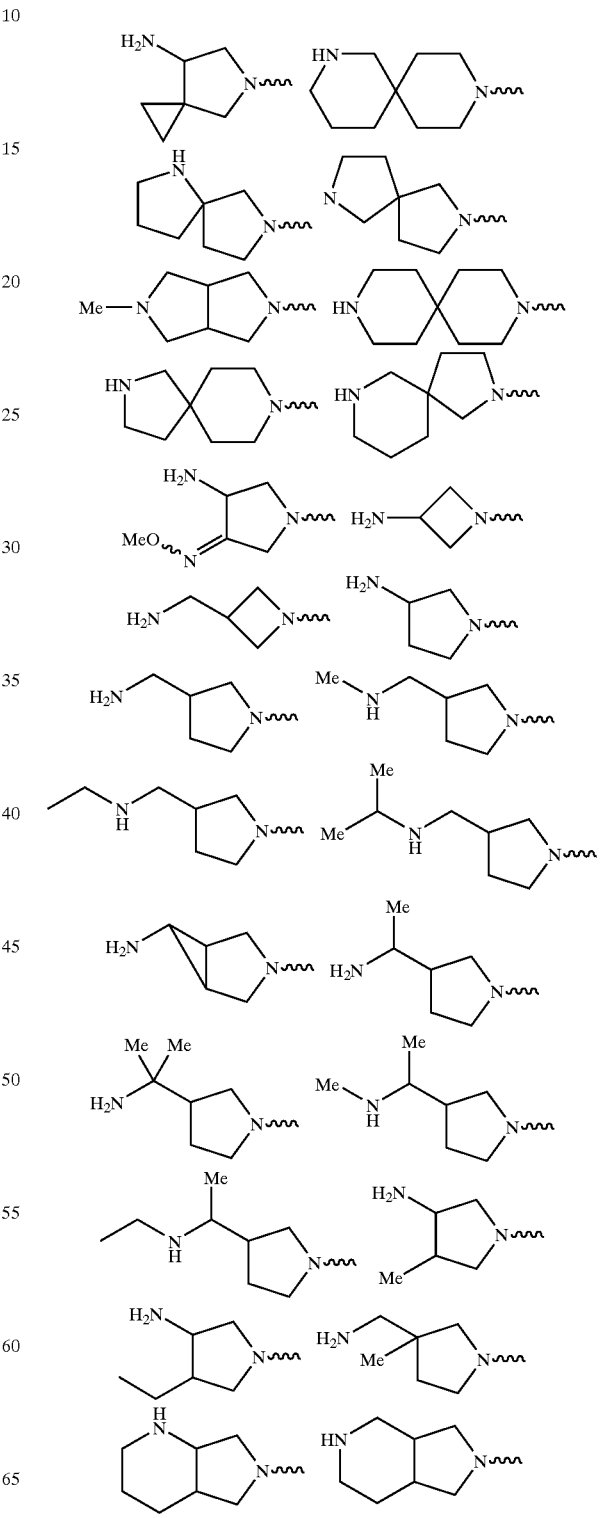

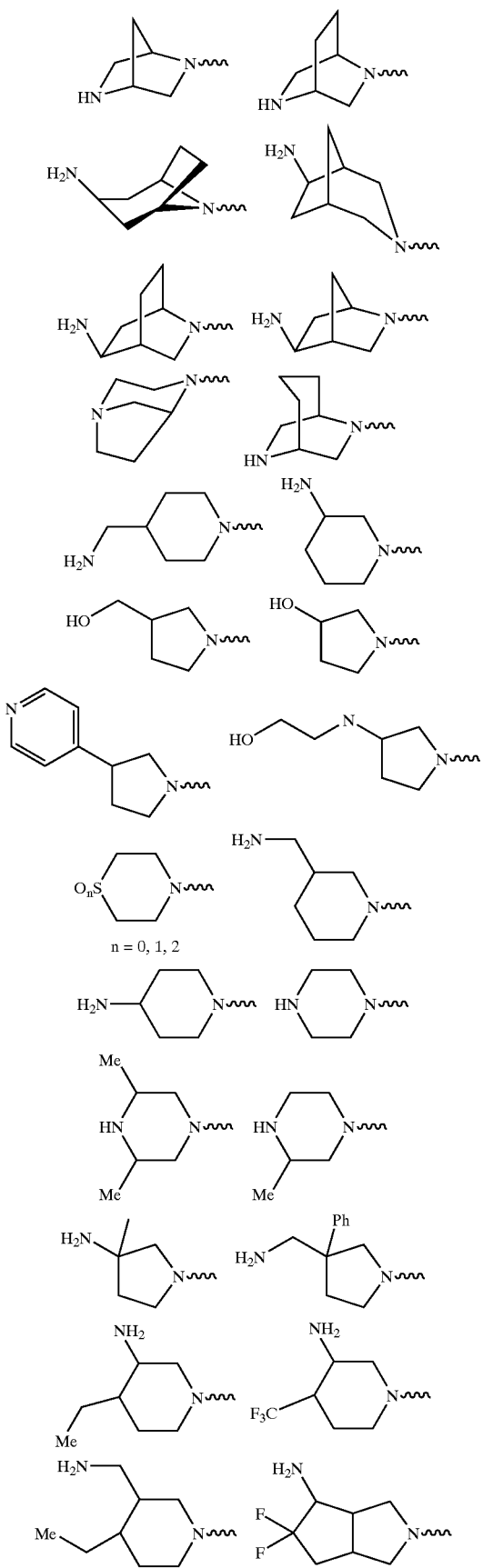
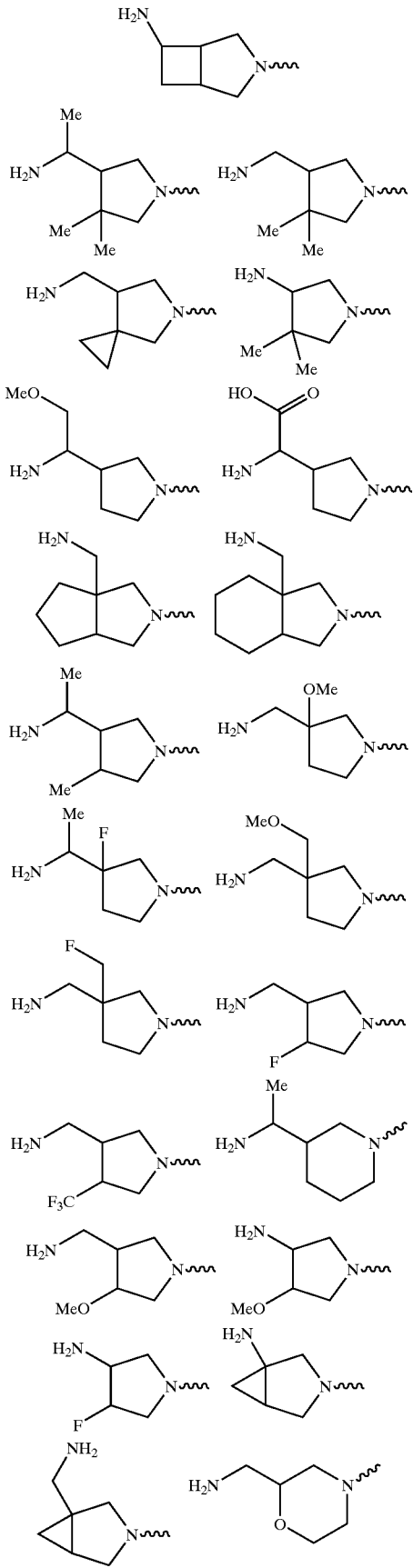

-continued
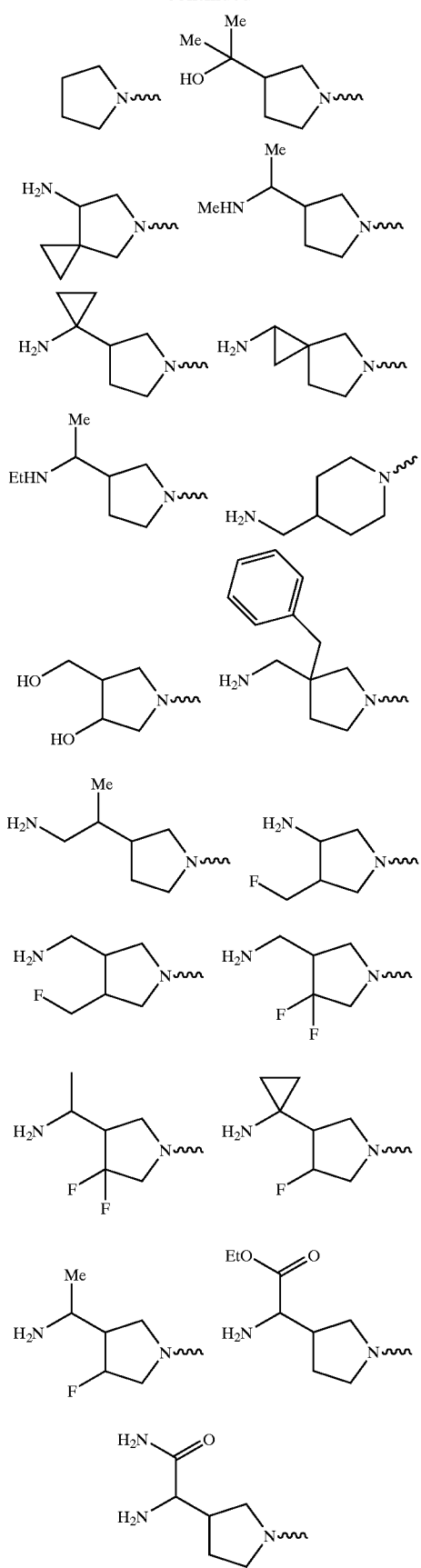
-continued
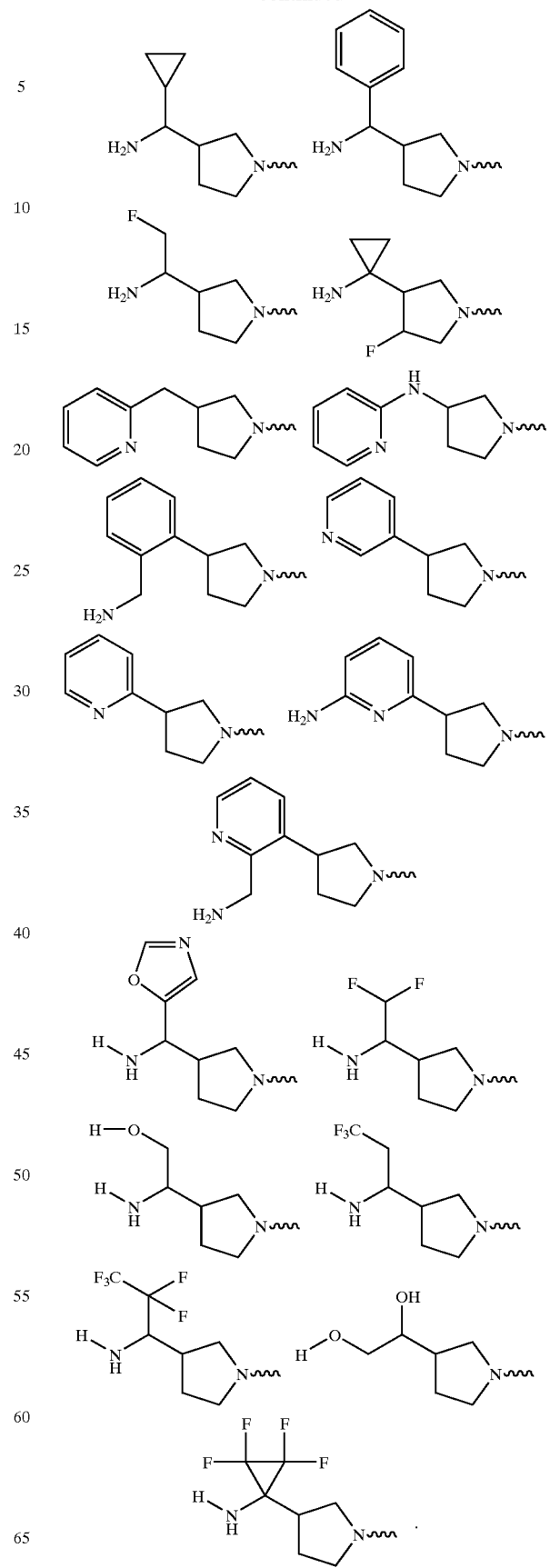

11. The compound of claim 9, wherein:
$R_1$ is cyclopropyl;
$R_2$ is H OH, or $NH_2$;
$R_3$ is H; $R_4$ is F or Cl;
$R_g$ and $R_h$, together with the nitrogen to which they are attached, are
   1-pyrrolidinyl or substituted 1-pyrrolidinyl,
   1-piperidinyl or substituted 1-piperidinyl;
   1-piperizinyl or substituted 1-piperizinyl; and
$R_6$ is F, Cl methyl, methoxy, $OCF_3$, $OCHF_2$, $OCH_2F$, $OCH_2CF_3$, $OCH_2CHF_2$, or $OCH_2CH_2F$.

12. The compound of claim 9, wherein:
$R_1$ is cyclopropyl;
$R_2$ is H or $NH_2$;
$R_3$ is H;
$R_4$ is F;
$R_g$ and $R_h$, together with the nitrogen to which they are attached, are
   1-pyrrolidinyl or substituted 1-pyrrolidinyl,
   1-piperidinyl or substituted 1-piperidinyl,
   1-piperizinyl or substituted 1-piperizinyl; and
$R_6$ is methyl, methoxy, $OCF_3$, $OCHF_2$, $OCH_2F$, $OCH_2CF_3$, $OCH_2CHF_2$, or $OCH_2CH_2F$.

13. the compound of claim 9, wherein:
$R_1$ is cyclopropyl;
$R_2$ is H or $NH_2$;
$R_3$ is H;
$R_4$ is F;
$R_g$ and $R_h$, together with the nitrogen to which they are attached, are
   1-pyrrolidinyl or substituted 1-pyrrolidinyl, or
   1-piperidinyl or substituted 1-piperidinyl, and
$R_6$ is methyl, methoxy, $OCF_3$, $OCHF_2$, $OCH_2F$, $OCH_2CF_3$, $OCH_2CHF_2$, or $OCH_2CH_2F$.

14. The compound of claim 9, wherein:
$R_1$ is cyclopropyl,
$R_2$ is H or $NH_2$;
$R_3$ is H;
$R_4$ is F;
$R_g$ and $R_h$, together with the nitrogen to which they are attached, are
   1-pyrrolidinyl or substituted 1-pyrrolidinyl, or
   1-piperidinyl or substituted 1-piperidinyl; and
$R_6$ is methyl, methoxy, $OCF_3$, $OCHF_2$, $OCH_2F$, $OCH_2CF_3$, $OCH_2CHF_2$.

15. A compound which is:
2-Amino-4-cyclopropyl-7-fluoro-5-methyl-6-[3-(1-methylaminoethyl)pyrrolidin-1-yl]pyrido[1,2-c]pyrimidine-1,3-dione;
2-Amino-4-cyclopropyl-7-fluoro-5-methyl-6-pyrrolidin-1-yl-pyrido[1,2-c]pyrimidine-1,3-dione;
2-Amino-4-cyclopropyl-7-fluoro-6-[3-(1-hydroxyethyl)pyrrolidin-1-yl-5-methylpyrido[1,2-c]pyrimidine-1,3-dione;
2-Amino-6-[(R)-3-(1-aminocyclopropyl)pyrrolidin-1-yl]-4-cyclopropyl-7-fluoro-5-methylpyrido[1,2-c]pyrimidine-1,3-dione;
2-Amino-6-((3S,4S) and (3R,4R)-3-aminomethyl-4-fluoropyrrolidin-1-yl)-4-cyclopropyl-7-fluoro-5-methylpyrido[1,2-c]pyrimidine-1,3-dione;
2-Amino-6-[(R)-3-((S)-1-aminoethyl)pyrrolidin-1-yl]-4-cyclopropyl-7-fluoro-5-methyl-pyrido[1,2-c]pyrimidine-1,3-dione; hydrochloride; and
2-Amino-6-[4-(1-aminoethyl)-3,3-dimethylpyrrolidin-1-yl]-4-cyclopropyl-7-fluoro-5-methyl-pyrido[1,2-c]pyrimidine-1,3-dione; hydrochloride;
2-Amino-4-cyclopropyl-7-fluoro-5-methyl-6-[3-(1-methylaminoethyl)pyrrolidin-1-yl]-pyrido[1,2-c]pyrimidine-1,3-dione;
2-Amino-4-cyclopropyl-7-fluoro-5-methyl-6-pyrrolidin-1-ylpyrido[1,2-c]pyrimidine-1,3-dione;
2-Amino-4-cyclopropyl-7-fluoro-6-[3-(1-hydroxyethyl)pyrrolidin-1-yl-5-methyl-pyrido[1,2-c]pyrimidine-1,3-dione;
2-Amino-6-[(R)-3-((R)-1-aminoethyl)-pyrrolidin-1-yl]-4-cyclopropyl-7-fluoro-5-methylpyrido[1,2-c]pyrimidine-1,3-dione hydrochloride;
2-Amino-6-[(R)-3-((S)-1-aminoethyl)-pyrrolidin-1-yl]-4-cyclopropyl-7-fluoro-5-methylpyrido[1,2-c]pyrimidine-1,3-dione hydrochloride;
2-Amino-6-[4-(1-aminoethyl)-3,3-dimethyl-pyrrolidin-1-yl]-4-cyclopropropyl-7-fluoro-5-methylpyrido[1,2-c]pyrimidine-1,3-dione hydrochloride;
2-Amino-6-(3-aminopyrrolidin-1-yl)-4-cyclopropyl-7-fluoro-5-methylpyrido[1,2-c]pyrimidine-1,3-dione hydrochloride;
2-Amino-6-[3-(1-aminoethyl)-4-methylpyrrolidin-1-yl]-4-cyclopropyl-7-fluoro-5-methylpyrido[1,2-c]pyrimidine-1,3-dione hydrochloride;
2-Amino-6-[3-(1-amino-1-phenylmethyl)pyrrolidin-1-yl]-4-cyclopropyl-7-fluoro-5-methylpyrido[1,2-c]pyrimidine-1,3-dione;
2-Amino-6-{3-[1-amino-1-(2-fluorophenyl)methyl]pyrrolidin-1-yl}-4-cyclopropyl-7-fluoro-5-methylpyrido[1,2-c]pyrimidine-1,3-dione;
2-Amino-6-{3-[1-amino-1-(4-fluorophenyl)methyl]pyrrolidin-1-yl}-4-cyclopropyl-7-fluoro-5-methylpyrido[1,2-c]pyrimidine-1,3-dione;
2-Amino-6-{3-[1-amino-1-(2,4-difluorophenyl)methyl]pyrrolidin-1-yl}-4-cyclopropyl-7-fluoro-5-methylpyrido[1,2-c]pyrimidine-1,3-dione;
2-Amino-6-{3-[1-amino-1-(2,6-difluorophenyl)methyl]pyrrolidin-1-yl}-4-cyclopropyl-7-fluoro-5-methylpyrido[1,2-c]pyrimidine-1,3-dione;
2-Amino-6-{3-[1-amino-1-(2,4,6-trifluorophenyl)methyl]pyrrolidin-1-yl}-4-cyclopropyl-7-fluoro-5-methylpyrido[1,2-c]pyrimidine-1,3-dione;
2-Amino-6-[3-(1-aminopropyl)pyrrolidin-1-yl]-4-cyclopropyl-7-fluoro-5-methylpyrido[1,2-c]pyrimidine-1,3-dione;
2-Amino-6-[3-(1-amino-2-methylpropyl)pyrrolidin-1-yl]-4-cyclopropyl-7-fluoro-5-methylpyrido[1,2-c]pyrimidine-1,3-dione;
2-Amino-6-[3-(1-amino-2-cyclopropylmethyl)pyrrolidin-1-yl]-4-cyclopropyl-7-fluoro-5-methylpyrido[1,2-c]pyrimidine-1,3-dione;
2-Amino-6-[3-(1-aminocyclopropyl)pyrrolidin-1-yl]-4-cyclopropyl-7-fluoro-5-methylpyrido[1,2-c]pyrimidine-1,3-dione;
2-Amino-6-[3-(1-aminocyclopropyl)-4-fluoropyrrolidin-1-yl]-4-cyclopropyl-7-fluoro-5-methylpyrido[1,2-c]pyrimidine-1,3-dione;
2-Amino-6-[3-(1-amino-1-phenylmethyl)-4-fluoropyrrolidin-1-yl]-4-cyclopropyl-7-fluoro-5-methylpyrido[1,2-c]pyrimidine-1,3-dione;
2-Amino-6-[3-(1-amino-2-fluoroethyl)pyrrolidin-1-yl]-4-cyclopropyl-7-fluoro-5-methylpyrido[1,2-c]pyrimidine-1,3-dione;

2-Amino-6-[3-(1-amino-2,2-difluorocyclopropyl)pyrrolidin-1-yl]-4-cyclopropyl-7-fluoro-5-methylpyrido[1,2-c]pyrimidine-1,3-dione;
2-Amino-6-[3-(1-aminoethyl)pyrrolidin-1-yl]-4-cyclopropyl-7-fluoro-5-methylpyrido[1,2-c]pyrimidine-1,3-dione;
2-Amino-6-[3-(1-amino-2-fluorocyclopropyl)pyrrolidin-1-yl]-4-cyclopropyl-7-fluoro-5-methylpyrido[1,2-c]pyrimidine-1,3-dione;
2-Amino-6-[3-(1-amino-1-methylethyl)pyrrolidin-1-yl]-4-cyclopropyl-7-fluoro-5-methylpyrido[1,2-c]pyrimidine-1,3-dione;
2-Amino-6-[3-(1-aminoethyl)-4-fluoropyrrolidin-1-yl]-4-cyclopropyl-7-fluoro-5-methylpyrido[1,2-c]pyrimidine-1,3-dione;
2-Amino-6-[3-(1-amino-1-pyridin-2-ylmethyl)pyrrolidin-1-yl]-4-cyclopropyl-7-fluoro-5-methylpyrido[1,2-c]pyrimidine-1,3-dione;
2-Amino-6-[3-(1-amino-2-fluorocyclopropyl)-4-fluoropyrrolidin-1-yl]-4-cyclopropyl-7-fluoro-5-methylpyrido[1,2-c]pyrimidine-1,3-dione;
2-Amino-6-[3-(1-amino-1-pyridin-3-ylmethyl)pyrrolidin-1-yl]-4-cyclopropyl-7-fluoro-5-methylpyrido[1,2-c]pyrimidine-1,3-dione;
2-Amino-6-[3-(1-amino-1-pyridin-4-ylmethyl)pyrrolidin-1-yl]-4-cyclopropyl-7-fluoro-5-methylpyrido[1,2-c]pyrimidine-1,3-dione;
2-Amino-6-(4-aminohexahydrocyclopenta[c]pyrrol-2-yl)-4-cyclopropyl-7-fluoro-5-methylpyrido[1,2-c]pyrimidine-1,3-dione;
2-Amino-6-(4-amino-5-fluorohexahydrocyclopenta[c]pyrrol-2-yl)-4-cyclopropyl-7-fluoro-5-methylpyrido[1,2-c]pyrimidine-1,3-dione;
2-Amino-4-cyclopropyl-7-fluoro-5-methyl-6-(3-phenylpyrrolidin-1-yl)pyrido[1,2-c]pyrimidine-1,3-dione;
2-Amino-4-cyclopropyl-7-fluoro-5-methyl-6-(3-pyridin-2-ylpyrrolidin-1-yl)pyrido[1,2-c]pyrimidine-1,3-dione;
2-Amino-4-cyclopropyl-7-fluoro-5-methyl-6-(3-pyridin-3-ylpyrrolidin-1-yl)pyrido[1,2-c]pyrimidine-1,3-dione;
2-Amino-4-cyclopropyl-7-fluoro-5-methyl-6-(3-pyridin-4-ylpyrrolidin-1-yl)pyrido[1,2-c]pyrimidine-1,3-dione;
2-Amino-4-cyclopropyl-7-fluoro-5-methyl-6-(piperazin-1-yl)pyrido[1,2-c]pyrimidine-1,3-dione;
2-Amino-4-cyclopropyl-7-fluoro-5-methyl-6-(4-methylpiperazin-1-yl)pyrido[1,2-c]pyrimidine-1,3-dione;
N-{1-[1-(2-Amino-4-cyclopropyl-7-fluoro-5-methyl-1,3-dioxo-2,3-dihydro-1H-pyrido[1,2-c]pyrimidin-6-yl)pyrrolidin-3-yl]ethyl}methanesulfonamide,
2-Amino-4-cyclopropyl-7-fluoro-5-methyl-6-octahydropyrrolo[3,4-b]pyridin-6-yl)pyrido[1,2-c]pyrimidine-1,3-dione;
2-Amino-6-(7-amino-5-azaspiro[2.4]hept-5-yl)-4-cyclopropyl-7-fluoro-5-methylpyrido[1,2-c]pyrimidine-1,3-dione;
2-Amino-4-cyclopropyl-7-fluoro-5-methyl-6-(thiophen-3-yl)pyrido[1,2-c]pyrimidine-1,3-dione;
2-Amino-4-cyclopropyl-7-fluoro-5-methyl-6-(1-methyl-2,3-dihydro-1H-isoindol-5-yl)pyrido[1,2-c]pyrimidine-1,3-dione;
2-Amino-4-cyclopropyl-7-fluoro-6-(7-hydroxymethyl-5-azaspiro[2.4]hept-5-yl)-5-methylpyrido[1,2-c]pyrimidine-1,3-dione;
2-Amino-6-(3-amino-4-methoxyiminopyrrolidin-1-yl)-4-cyclopropyl-7-fluoro-5-methylpyrido[1,2-c]pyrimidine-1,3-dione;
2-Amino-4-cyclopropyl-7-fluoro-5-methyl-6-(3-methylaminomethylpyrrolidin-1-yl)pyrido[1,2-c]pyrimidine-1,3-dione;
2-Amino-6-(5-aminomethylthiophen-3-yl)-4-cyclopropyl-7-fluoro-5-methylpyrido[1,2-c]pyrimidine-1,3-dione;
2-Amino-6-[3-(1-aminoethyl)-3-fluoropyrrolidin-1-yl]-4-cyclopropyl-7-fluoro-5-methylpyrido[1,2-c]pyrimidine-1,3-dione;
2-Amino-6-(5-aminomethylthiophen-3-yl]-4-cyclopropyl-7-fluoro-5-methylpyrido[1,2-c]pyrimidine-1,3-dione;
2-Amino-6-(5-aminomethylthiophen-2-yl]-4-cyclopropyl-7-fluoro-5-methylpyrido[1,2-c]pyrimidine-1,3-dione;
2-Amino-6-(4-aminomethylthiophen-2-yl]-4-cyclopropyl-7-fluoro-5-methylpyrido[1,2-c]pyrimidine-1,3-dione;
2-Amino-6-(4-aminomethylthiophen-3-yl]-4-cyclopropyl-7-fluoro-5-methylpyrido[1,2-c]pyrimidine-1,3-dione;
2-Amino-4-cyclopropyl-6-(5,6-dihydro-4H-thieno[2,3-c]pyrrol-3-yl)-7-fluoro-5-methylpyrido[1,2-c]pyrimidine-1,3-dione;
2-Amino-4-cyclopropyl-6-(5,6-dihydro-4H-thieno[2,3-c]pyrrol-2-yl)-7-fluoro-5-methylpyrido[1,2-c]pyrimidine-1,3-dione;
2-Amino-4-cyclopropyl-7-fluoro-5-methyl-6-(6-methyl-5,6-dihydro-4H-thieno[2,3-c]pyrrol-2-yl)pyrido[1,2-c]pyrimidine-1,3-dione;
2-Amino-4-cyclopropyl-7-fluoro-5-methyl-6-(6-methyl-5,6-dihydro-4H-thieno[2,3-c]pyrrol-3-yl)pyrido[1,2-c]pyrimidine-1,3-dione;
2-Amino-4-cyclopropyl-7-fluoro-5-methyl-6-(5-pyridin-4-ylthiophen-3-yl)pyrido[1,2-c]pyrimidine-1,3-dione;
2-Amino-4-cyclopropyl-7-fluoro-5-methyl-6-(5-pyridin-3-ylthiophen-3-yl)pyrido[1,2-c]pyrimidine-1,3-dione;
2-Amino-4-cyclopropyl-7-fluoro-5-methyl-6-(5-pyridin-2-ylthiophen-3-yl)pyrido[1,2-c]pyrimidine-1,3-dione;
2-Amino-4-cyclopropyl-7-fluoro-5-methyl-6-(4-pyridin-4-ylthiophen-3-yl)pyrido[1,2-c]pyrimidine-1,3-dione;
2-Amino-4-cyclopropyl-7-fluoro-5-methyl-6-(4-pyridin-3-ylthiophen-3-yl)pyrido[1,2-c]pyrimidine-1,3-dione;
2-Amino-4-cyclopropyl-7-fluoro-5-methyl-6-(4-pyridin-2-ylthiophen-3-yl)pyrido[1,2-c]pyrimidine-1,3-dione;
2-Amino-4-cyclopropyl-7-fluoro-5-methyl-6-pyridin-4-ylpyrido[1,2-c]pyrimidine-1,3-dione;
2-Amino-6-(4-aminomethylpyridin-2-yl)-4-cyclopropyl-7-fluoro-5-methylpyrido[1,2-c]pyrimidine-1,3-dione;
2-Amino-6-(5-aminomethylpyridin-2-yl)-4-cyclopropyl-7-fluoro-5-methylpyrido[1,2-c]pyrimidine-1,3-dione;
2-Amino-6-(6-aminomethylpyridin-2-yl)-4-cyclopropyl-7-fluoro-5-methylpyrido[1,2-c]pyrimidine-1,3-dione;
2-Amino-6-(5-aminomethylpyrimidin-2-yl]-4-cyclopropyl-7-fluoro-5-methylpyrido[1,2-c]pyrimidine-1,3-dione;
2-Amino-4-cyclopropyl-7-fluoro-5-methyl-6-pyrimidin-2-ylpyrido[1,2-c]pyrimidine-1,3-dione;
2-Amino-6-(2-aminomethylpyrimidin-5-yl]-4-cyclopropyl-7-fluoro-5-methylpyrido[1,2-c]pyrimidine-1,3-dione;

2-Amino-4-cyclopropyl-7-fluoro-5-methyl-6-pyrimidin-5-ylpyrido[1,2-c]pyrimidine-1,3-dione;

2-Amino-4-cyclopropyl-7-fluoro-5-methyl-6-pyrazin-2-ylpyrido[1,2-c]pyrimidine-1,3-dione;

2-Amino-6-(6-aminomethylpyrazin-2-yl]-4-cyclopropyl-7-fluoro-5-methylpyrido[1,2-c]pyrimidine-1,3-dione;

2-Amino-6-[3-(6-aminomethylpyridin-2-yl)pyrrolidin-1-yl]-4-cyclopropyl-7-fluoro-5-methylpyrido[1,2-c]pyrimidine-1,3-dione;

2-Amino-6-[3-(2-aminomethylpyridin-3-yl)pyrrolidin-1-yl]-4-cyclopropyl-7-fluoro-5-methylpyrido[1,2-c]pyrimidine-1,3-dione;

2-Amino-6-[5-(2-aminomethylpyridin-3-yl)thiophen-3-yl]-4-cyclopropyl-7-fluoro-5-methylpyrido[1,2-c]pyrimidine-1,3-dione;

2-Amino-6-[5-(2-aminomethylpyridin-3-yl)thiophen-2-yl]-4-cyclopropyl-7-fluoro-5-methylpyrido[1,2-c]pyrimidine-1,3-dione;

2-Amino-6-[5-(6-aminomethylpyridin-2-yl)thiophen-2-yl]-4-cyclopropyl-7-fluoro-5-methylpyrido[1,2-c]pyrimidine-1,3-dione;

2-Amino-6-[5-(6-aminomethylpyridin-2-yl)thiophen-3-yl]-4-cyclopropyl-7-fluoro-5-methylpyrido[1,2-c]pyrimidine-1,3-dione;

2-Amino-6-[4-(2-aminomethylpyridin-3-yl)thiophen-2-yl]-4-cyclopropyl-7-fluoro-5-methylpyrido[1,2-c]pyrimidine-1,3-dione;

2-Amino-6-[3-(2-aminomethylpyridin-3-yl)thiophen-2-yl]-4-cyclopropyl-7-fluoro-5-methylpyrido[1,2-c]pyrimidine-1,3-dione;

2-Amino-6-[4-(6-aminomethylpyridin-2-yl)thiophen-3-yl]-4-cyclopropyl-7-fluoro-5-methylpyrido[1,2-c]pyrimidine-1,3-dione;

2-Amino-4-cyclopropyl-7-fluoro-5-methyl-6-(4-pyridin-4-ylthiophen-2-yl)pyrido[1,2-c]pyrimidine-1,3-dione;

2-Amino-6-[4-(1-aminoethyl)thiophen-2-yl]-4-cyclopropyl-7-fluoro-5-methylpyrido[1,2-c]pyrimidine-1,3-dione;

2-Amino-6-[(R)-3-(1-aminocyclopropyl)pyrrolidin-1-yl]-4-cyclopropyl-7-fluoro-5-methylpyrido[1,2-c]pyrimidine-1,3-dione;

2-Amino-6-((3S,4S) and (3R,4R)-3-aminomethyl-4-fluoropyrrolidin-1-yl)-4-cyclopropyl-7-fluoro-5-methylpyrido[1,2-c]pyrimidine-1,3-dione;

2-Amino-6-(3-aminomethylpyrrolidin-1-yl)-4-cyclopropyl-7-fluoro-5-methylpyrido-[1,2-c]pyrimidine-1,3-dione;

2-Amino-6-(7-amino-5-azospiro[2.4]hept-5-yl)-4-cyclopropyl-7-fluoro-5-methylpyrido[1,2-c]primidine-1,3-dione;

2-Amino-6-[3-(aminooxazol-4-yl-methyl)pyrrolidin-1-yl]-4-cyclopropyl-7-fluoro-5-methylpyrido[1,2-c]pyrimidine-1,3-dione;

2-Amino-6-(4-aminooctahydroisoindol-2-yl)-4-cyclopropyl-7-fluoro-5-methylpyrido[1,2-c]pyrimidine-1,3-dione;

2-Amino-6-[3-(1-amino-1-methylethyl)pyrrolidine-1-yl]-4-cyclopropyl-7-fluoro-5-methylpyrido[1,2-c]pyrimidine-1,3-dione; and 6-Chloro-4-cyclopropyl-7-fluoro-5-methylpyrido[1,2-c]pyrimidine-1,3-dione;

2-Amino-4-cyclopropyl-7-fluoro-5-methoxy-6-[3-(1-methylaminoethyl)pyrrolidin-1-yl]pyrido[1,2-c]pyrimidine-1,3-dione;

2-Amino-4-cyclopropyl-7-fluoro-5-methoxy-6-pyrrolidin-1-yl-pyrido[1,2-c]pyrimidine-1,3-dione;

2-Amino-4-cyclopropyl-7-fluoro-6-[3-(1-hydroxyethyl)pyrrolidin-1-yl-5-methoxypyrido[1,2-c]pyrimidine-1,3-dione;

2-Amino-6-[(R)-3-(1-aminocyclopropyl)pyrrolidin-1-yl]-4-cyclopropyl-7-fluoro-5-methoxypyrido[1,2-c]pyrimidine-1,3-dione;

2-Amino-6-((3S,4S) and (3R,4R)-3-aminomethyl-4-fluoropyrrolidin-1-yl)-4-cyclopropyl-7-fluoro-5-methoxypyrido[1,2-c]pyrimidine-1,3-dione;

2-Amino-6-[(R)-3-((S)-1-aminoethyl)pyrrolidin-1-yl]-4-cyclopropyl-7-fluoro-5-methoxypyrido[1,2-c]pyrimidine-1,3-dione; hydrochloride; and 2-Amino-6-[4-(1-aminoethyl)-3,3-dimethylpyrrolidin-1-yl]-4-cyclopropyl-7-fluoro-5-methoxypyrido[1,2-c]pyrimidine-1,3-dione; hydrochloride;

2-Amino-4-cyclopropyl-7-fluoro-5-methoxy-6-[3-(1-methylaminoethyl)pyrrolidin-1-yl]-pyrido[1,2-c]pyrimidine-1,3-dione;

2-Amino-4-cyclopropyl-7-fluoro-5-methoxy-6-pyrrolidin-1-ylpyrido[1,2-c]pyrimidine-1,3-dione;

2-Amino-4-cyclopropyl-7-fluoro-6-[3-(1-hydroxyethyl)pyrrolidin-1-yl-5-methoxypyrido[1,2-c]pyrimidine-1,3-dione;

2-Amino-6-[(R)-3-((R)-1-aminoethyl)-pyrrolidin-1-yl]-4-cyclopropyl-7-fluoro-5-methoxypyrido[1,2-c]pyrimidine-1,3-dione hydrochloride;

2-Amino-6-[(R)-3-((S)-1-aminoethyl)-pyrrolidin-1-yl]-4-cyclopropyl-7-fluoro-5-methoxypyrido[1,2-c]pyrimidine-1,3-dione hydrochloride;

2-Amino-6-[4-(1-aminoethyl)-3,3-dimethyl-pyrrolidin-1-yl]-4-cyclopropyl-7-fluoro-5-methoxypyrido[1,2-c]pyrimidine-1,3-dione hydrochloride;

2-Amino-6-(3-aminopyrrolidin-1-yl)-4-cyclopropyl-7-fluoro-5-methoxypyrido[1,2-c]pyrimidine-1,3-dione hydrochloride;

2-Amino-6-[3-(1-aminoethyl)-4-methylpyrrolidin-1-yl]-4-cyclopropyl-7-fluoro-5-methoxypyrido[1,2-c]pyrimidine-1,3-dione hydrochloride;

2-Amino-6-[3-(1-amino-1-phenylmethyl)pyrrolidin-1-yl]-4-cyclopropyl-7-fluoro-5-methoxypyrido[1,2-c]pyrimidine-1,3-dione;

2-Amino-6-{3-[1-amino-1-(2-fluorophenyl)methyl]pyrrolidin-1-yl}-4-cyclopropyl-7-fluoro-5-methoxypyrido[1,2-c]pyrimidine-1,3-dione;

2-Amino-6-{3-[1-amino-1-(4-fluorophenyl)methyl]pyrrolidin-1-yl}-4-cyclopropyl-7-fluoro-5-methoxypyrido[1,2-c]pyrimidine-1,3-dione;

2-Amino-6-{3-[1-amino-1-(2,4-difluorophenyl)methyl]pyrrolidin-1-yl}-4-cyclopropyl-7-fluoro-5-methoxypyrido[1,2-c]pyrimidine-1,3-dione;

2-Amino-6-{3-[1-amino-1-(2,6-difluorophenyl)methyl]pyrrolidin-1-yl}-4-cyclopropyl-7-fluoro-5-methoxypyrido[1,2-c]pyrimidine-1,3-dione;

2-Amino-6-{3-[1-amino-1-(2,4,6-trifluorophenyl)methyl]pyrrolidin-1-yl}-4-cyclopropyl-7-fluoro-5-methoxypyrido[1,2-c]pyrimidine-1,3-dione;

2-Amino-6-[3-(1-aminopropyl)pyrrolidin-1-yl]-4-cyclopropyl-7-fluoro-5-methoxypyrido[1,2-c]pyrimidine-1,3-dione;

2-Amino-6-[3-(1-amino-2-methylpropyl)pyrrolidin-1-yl]-4-cyclopropyl-7-fluoro-5-methoxypyrido[1,2-c]pyrimidine-1,3-dione;

2-Amino-6-[3-(1-amino-2-cyclopropylmethyl)pyrrolidin-1-yl]-4-cyclopropyl-7-fluoro-5-methoxypyrido[1,2-c]pyrimidine-1,3-dione;
2-Amino-6-[3-(1-aminocyclopropyl)pyrrolidin-1-yl]-4-cyclopropyl-7-fluoro-5-methoxypyrido[1,2-c]pyrimidine-1,3-dione;
2-Amino-6-[3-(1-aminocyclopropyl)-4-fluoropyrrolidin-1-yl]-4-cyclopropyl-7-fluoro-5-methoxypyrido[1,2-c]pyrimidine-1,3-dione;
2-Amino-6-[3-(1-amino-1-phenylmethyl)-4-fluoropyrrolidin-1-yl]-4-cyclopropyl-7-fluoro-5-methoxypyrido[1,2-c]pyrimidine-1,3-dione;
2-Amino-6-[3-(1-amino-2-fluoroethyl)pyrrolidin-1-yl]-4-cyclopropyl-7-fluoro-5-methoxypyrido[1,2-c]pyrimidine-1,3-dione;
2-Amino-6-[3-(1-amino-2,2-difluorocyclopropyl)pyrrolidin-1-yl]-4-cyclopropyl-7-fluoro-5-methoxypyrido[1,2-c]pyrimidine-1,3-dione;
2-Amino-6-[3-(1-aminoethyl)pyrrolidin-1-yl]-4-cyclopropyl-7-fluoro-5-methoxypyrido[1,2-c]pyrimidine-1,3-dione;
2-Amino-6-[3-(1-amino-2-fluorocyclopropyl)pyrrolidin-1-yl]-4-cyclopropyl-7-fluoro-5-methoxypyrido[1,2-c]pyrimidine-1,3-dione;
2-Amino-6-[3-(1-amino-1-methylethyl)pyrrolidin-1-yl]-4-cyclopropyl-7-fluoro-5-methoxypyrido[1,2-c]pyrimidine-1,3-dione;
2-Amino-6-[3-(1-aminoethyl)-4-fluoropyrrolidin-1-yl]-4-cyclopropyl-7-fluoro-5-methoxypyrido[1,2-c]pyrimidine-1,3-dione;
2-Amino-6-[3-(1-amino-1-pyridin-2-ylmethyl)pyrrolidin-1-yl]-4-cyclopropyl-7-fluoro-5-methoxypyrido[1,2-c]pyrimidine-1,3-dione;
2-Amino-6-[3-(1-amino-2-fluorocyclopropyl)-4-fluoropyrrolidin-1-yl]-4-cyclopropyl-7-fluoro-5-methoxypyrido[1,2-c]pyrimidine-1,3-dione;
2-Amino-6-[3-(1-amino-1-pyridin-3-ylmethyl)pyrrolidin-1-yl]-4-cyclopropyl-7-fluoro-5-methoxypyrido[1,2-c]pyrimidine-1,3-dione;
2-Amino-6-[3-(1-amino-1-pyridin-4-ylmethyl)pyrrolidin-1-yl]-4-cyclopropyl-7-fluoro-5-methoxypyrido[1,2-c]pyrimidine-1,3-dione;
2-Amino-6-(4-aminohexahydrocyclopenta[c]pyrrol-2-yl)-4-cyclopropyl-7-fluoro-5-methoxypyrido[1,2-c]pyrimidine-1,3-dione;
2-Amino-6-(4-amino-5-fluorohexahydrocyclopenta[c]pyrrol-2-yl)-4-cyclopropyl-7-fluoro-5-methoxypyrido[1,2-c]pyrimidine-1,3-dione;
2-Amino-4-cyclopropyl-7-fluoro-5-methoxy-6-(3-phenylpyrrolidin-1-yl)pyrido[1,2-c]pyrimidine-1,3-dione;
2-Amino-4-cyclopropyl-7-fluoro-5-methoxy-6-(3-pyridin-2-ylpyrrolidin-1-yl)pyrido[1,2-c]pyrimidine-1,3-dione;
2-Amino-4-cyclopropyl-7-fluoro-5-methoxy-6-(3-pyridin-3-ylpyrrolidin-1-yl)pyrido[1,2-c]pyrimidine-1,3-dione;
2-Amino-4-cyclopropyl-7-fluoro-5-methoxy-6-(3-pyridin-4-ylpyrrolidin-1-yl)pyrido[1,2-c]pyrimidine-1,3-dione;
2-Amino-4-cyclopropyl-7-fluoro-5-methoxy-6-(piperazin-1-yl)pyrido[1,2-c]pyrimidine-1,3-dione;
2-Amino-4-cyclopropyl-7-fluoro-5-methoxy-6-(4-methylpiperazin-1-yl)pyrido[1,2-c]pyrimidine-1,3-dione;
N-{1-[1-(2-Amino-4-cyclopropyl-7-fluoro-5-methoxy-1,3-dioxo-2,3-dihydro-1H-pyrido[1,2-c]pyrimidin-6-yl)pyrrolidin-3-yl]ethyl}methanesulfonamide;
2-Amino-4-cyclopropyl-7-fluoro-5-methoxy-6-octahydropyrrolo[3,4-b]pyridin-6-yl)pyrido[1,2-c]pyrimidine-1,3-dione;
2-Amino-6-(7-amino-5-azaspiro[2.4]hept-5-yl)-4-cyclopropyl-7-fluoro-5-methoxypyrido[1,2-c]pyrimidine-1,3-dione;
2-Amino-4-cyclopropyl-7-fluoro-5-methoxy-6-(thiophen-3-yl)pyrido[1,2-c]pyrimidine-1,3-dione;
2-Amino-4-cyclopropyl-7-fluoro-5-methoxy-6-(1-methyl-2,3-dihydro-1H-isoindol-5-yl)pyrido[1,2-c]pyrimidine-1,3-dione;
2-Amino-4-cyclopropyl-7-fluoro-6-(7-hydroxymethyl-5-azaspiro[2.4]hept-5-yl)-5-methoxypyrido[1,2-c]pyrimidine-1,3-dione;
2-Amino-6-(3-amino-4-methoxyiminopyrrolidin-1-yl)-4-cyclopropyl-7-fluoro-5-methoxypyrido[1,2-c]pyrimidine-1,3-dione;
2-Amino-4-cyclopropyl-7-fluoro-5-methoxy-6-(3-methylaminomethylpyrrolidin-1-yl)pyrido[1,2-c]pyrimidine-1,3-dione;
2-Amino-6-(5-aminomethylthiophen-3-yl)-4-cyclopropyl-7-fluoro-5-methoxypyrido[1,2-c]pyrimidine-1,3-dione;
2-Amino-6-[3-(1-aminoethyl)-3-fluoropyrrolidin-1-yl]-4-cyclopropyl-7-fluoro-5-methoxypyrido[1,2-c]pyrimidine-1,3-dione;
2-Amino-6-(5-aminomethylthiophen-3-yl)-4-cyclopropyl-7-fluoro-5-methoxypyrido[1,2-c]pyrimidine-1,3-dione;
2-Amino-6-(5-aminomethylthiophen-2-yl)-4-cyclopropyl-7-fluoro-5-methoxypyrido[1,2-c]pyrimidine-1,3-dione;
2-Amino-6-(4-aminomethylthiophen-2-yl)-4-cyclopropyl-7-fluoro-5-methoxypyrido[1,2-c]pyrimidine-1,3-dione;
2-Amino-6-(4-aminomethylthiophen-3-yl)-4-cyclopropyl-7-fluoro-5-methoxypyrido[1,2-c]pyrimidine-1,3-dione;
2-Amino-4-cyclopropyl-6-(5,6-dihydro-4H-thieno[2,3-c]pyrrol-3-yl)-7-fluoro-5-methoxypyrido[1,2-c]pyrimidine-1,3-dione;
2-Amino-4-cyclopropyl-6-(5,6-dihydro-4H-thieno[2,3-c]pyrrol-2-yl)-7-fluoro-5-methoxypyrido[1,2-c]pyrimidine-1,3-dione;
2-Amino-4-cyclopropyl-7-fluoro-5-methoxy-6-(6-methyl-5,6-dihydro-4H-thieno[2,3-c]pyrrol-2-yl)pyrido[1,2-c]pyrimidine-1,3-dione;
2-Amino-4-cyclopropyl-7-fluoro-5-methoxy-6-(6-methyl-5,6-dihydro-4H-thieno[2,3-c]pyrrol-3-yl)pyrido[1,2-c]pyrimidine-1,3-dione;
2-Amino-4-cyclopropyl-7-fluoro-5-methoxy-6-(5-pyridin-4-ylthiophen-3-yl)pyrido[1,2-c]pyrimidine-1,3-dione;
2-Amino-4-cyclopropyl-7-fluoro-5-methoxy-6-(5-pyridin-3-ylthiophen-3-yl)pyrido[1,2-c]pyrimidine-1,3-dione;
2-Amino-4-cyclopropyl-7-fluoro-5-methoxy-6-(5-pyridin-2-ylthiophen-3-yl)pyrido[1,2-c]pyrimidine-1,3-dione;
2-Amino-4-cyclopropyl-7-fluoro-5-methoxy-6-(4-pyridin-4-ylthiophen-3-yl)pyrido[1,2-c]pyrimidine-1,3-dione;

2-Amino-4-cyclopropyl-7-fluoro-5-methoxy-6-(4-pyridin-3-ylthiophen-3-yl)pyrido[1,2-c]pyrimidine-1,3-dione;

2-Amino-4-cyclopropyl-7-fluoro-5-methoxy-6-(4-pyridin-2-ylthiophen-3-yl)pyrido[1,2-c]pyrimidine-1,3-dione;

2-Amino-4-cyclopropyl-7-fluoro-5-methoxy-6-pyridin-4-ylpyrido[1,2-c]pyrimidine-1,3-dione;

2-Amino-6-(4-aminomethylpyridin-2-yl)-4-cyclopropyl-7-fluoro-5-methoxypyrido[1,2-c]pyrimidine-1,3-dione;

2-Amino-6-(5-aminomethylpyridin-2-yl)-4-cyclopropyl-7-fluoro-5-methoxypyrido[1,2-c]pyrimidine-1,3-dione;

2-Amino-6-(6-aminomethylpyridin-2-yl)-4-cyclopropyl-7-fluoro-5-methoxypyrido[1,2-c]pyrimidine-1,3-dione;

2-Amino-6-(5-aminomethylpyrimidin-2-yl]-4-cyclopropyl-7-fluoro-5-methoxypyrido[1,2-c]pyrimidine-1,3-dione;

2-Amino-4-cyclopropyl-7-fluoro-5-methoxy-6-pyrimidin-2-ylpyrido[1,2-c]pyrimidine-1,3-dione;

2-Amino-6-(2-aminomethylpyrimidin-5-yl]-4-cyclopropyl-7-fluoro-5-methoxypyrido[1,2-c]pyrimidine-1,3-dione;

2-Amino-4-cyclopropyl-7-fluoro-5-methoxy-6-pyrimidin-5-ylpyrido[1,2-c]pyrimidine-1,3-dione;

2-Amino-4-cyclopropyl-7-fluoro-5-methoxy-6-pyrazin-2-ylpyrido[1,2-c]pyrimidine-1,3-dione;

2-Amino-6-(6-aminomethylpyrazin-2-yl]-4-cyclopropyl-7-fluoro-5-methoxypyrido[1,2-c]pyrimidine-1,3-dione;

2-Amino-6-[3-(6-aminomethylpyridin-2-yl)pyrrolidin-1-yl]-4-cyclopropyl-7-fluoro-5-methoxypyrido[1,2-c]pyrimidine-1,3-dione;

2-Amino-6-[3-(2-aminomethylpyridin-3-yl)pyrrolidin-1-yl]-4-cyclopropyl-7-fluoro-5-methoxypyrido[1,2-c]pyrimidine-1,3-dione;

2-Amino-6-[5-(2-aminomethylpyridin-3-yl)thiophen-3-yl]4-cyclopropyl-7-fluoro-5-methoxypyrido[1,2-c]pyrimidine-1,3-dione;

2-Amino-6-[5-(2-aminomethylpyridin-3-yl)thiophen-2-yl]-4-cyclopropyl-7-fluoro-5-methoxypyrido[1,2-c]pyrimidine-1,3-dione;

2-Amino-6-[5-(6-aminomethylpyridin-2-yl)thiophen-2-yl]-4-cyclopropyl-7-fluoro-5-methoxypyrido[1,2-c]pyrimidine-1,3-dione;

2-Amino-6-[5-(6-aminomethylpyridin-2-yl)thiophen-3-yl]-4-cyclopropyl-7-fluoro-5-methoxypyrido[1,2-c]pyrimidine-1,3-dione;

2-Amino-6-[4-(2-aminomethylpyridin-3-yl)thiophen-3-yl]-4-cyclopropyl-7-fluoro-5-methoxypyrido[1,2-c]pyrimidine-1,3-dione;

2-Amino-6-[3-(2-aminomethylpyridin-3-yl)thiophen-2-yl]-4-cyclopropyl-7-fluoro-5-methoxypyrido[1,2-c]pyrimidine-1,3-dione;

2-Amino-6-[4-(6-aminomethylpyridin-3-yl)thiophen-3-yl]-4-cyclopropyl-7-fluoro-5-methoxypyrido[1,2-c]pyrimidine-1,3-dione;

2-Amino-4-cyclopropyl-7-fluoro-5-methoxy-6-(4-pyridin-4-ylthiophen-2-yl)pyrido[1,2-c]pyrimidine-1,3-dione;

2-Amino-6-[4-(1-aminoethyl)thiophen-2-yl]-4-cyclopropyl-7-fluoro-5-methoxypyrido[1,2-c]pyrimidine-1,3-dione;

2-Amino-6-[(R)-3-(1-aminocyclopropyl)pyrrolidin-1-yl]-4-cyclopropyl-7-fluoro-5-methoxypyrido[1,2-c]pyrimidine-1,3-dione;

2-Amino-6-((3S,4S) and (3R,4R)-3-aminomethyl-4-fluoropyrrolidin-1-yl)-4-cyclopropyl-7-fluoro-5-methoxypyrido[1,2-c]pyrimidine-1,3-dione;

2-Amino-6-(3-aminomethylpyrrolidin-1-yl)-4-cyclopropyl-7-fluoro-5-methoxypyrido-[1,2-c]pyrimidine-1,3-dione;

2-Amino-6-(7-amino-5-azospiro[2.4]hept-5-yl)-4-cyclopropyl-7-fluoro-5-methoxypyrido[1,2-c]primidine-1,3-dione;

2-Amino-6-[3-(aminooxazol-4-yl-methyl)pyrrolidin-1-yl]-4-cyclopropyl-7-fluoro-5-methoxypyrido[1,2-c]pyrimidine-1,3-dione;

2-Amino-6-(4-aminooctahydroisoindol-2-yl)-4-cyclopropyl-7-fluoro-5-methoxypyrido[1,2-c]pyrimidine-1,3-dione;

2-Amino-6-[3-(1-aminoethyl)pyrrolidin-1-yl]-4-cyclopropyl-7-fluoro-5,8-dimethylpyrido[1,2-c]pyrimidine-1,3-dione;

2-Amino-6-[3-(1-aminoethyl)pyrrolidin-1-yl]-4-cyclopropyl-7-fluoro-5-methoxy-8-methylpyrido[1,2-c]pyrimidine-1,3-dione;

2,8-Diamino-6-[3-(1-aminoethyl)pyrrolidin-1-yl]-4-cyclopropyl-7-fluoro-5-methylpyrido[1,2-c]pyrimidine-1,3-dione;

2,8-Diamino-6-(3-aminomethyl-4-fluoropyrrolidin-1-yl)-4-cyclopropyl-7-fluoro-5-methylpyrido[1,2-c]pyrimidine-1,3-dione;

2-Amino-6-(3-aminomethyl-4-fluoropyrrolidin-1-yl)-4-cyclopropyl-7-fluoro-5,8-dimethylpyrido[1,2-c]pyrimidine-1,3-dione;

2-Amino-6-[3-(1-amino-2,2-difluoroethyl)pyrrolidin-1-yl]-4-cyclopropyl-7-fluoro-5,8-dimethylpyrido[1,2-c]pyrimidine-1,3-dione;

2-Amino-6-[3-(1-amino-2,2-difluoroethyl)pyrrolidin-1-yl]-4-cyclopropyl-7-fluoro-5-methoxy-8-methylpyrido[1,2-c]pyrimidine-1,3-dione;

2-Amino-6-(4-aminomethyl-4,5,6,7-tetrahydrobenzo[b]thiophen-2-yl)-4-cyclopropyl-7-fluoro-5-methoxy-8-methylpyrido[1,2-c]pyrimidine-1,3-dione;

2-Amino-6-(4-aminomethyl-4,5,6,7-tetrahydrobenzo[b]thiophen-2-yl)-4-cyclopropyl-7-fluoro-5,8-dimethylpyrido[1,2-c]pyrimidine-1,3-dione;

2-Amino-6-(4-aminomethyl-4,5,6,7-tetrahydrobenzo[b]thiophen-2-yl)-4-cyclopropyl-7-fluoro-5-methylpyrido[1,2-c]pyrimidine-1,3-dione;

2-Amino-4-cyclopropyl-6-[3-(1,2-dihydroxyethyl)pyrrolidin-1-yl]-7-fluoro-5-methoxy-8-methylpyrido[1,2-c]pyrimidine-1,3-dione;

2-Amino-4-cyclopropyl-6-[3-(1,2-dihydroxyethyl)pyrrolidin-1-yl]-7-fluoro-5,8-dimethylpyrido[1,2-c]pyrimidine-1,3-dione;

2-Amino-4-cyclopropyl-6-[3-(1,2-dihydroxyethyl)pyrrolidin-1-yl]-7-fluoro-5-methylpyrido[1,2-c]pyrimidine-1,3-dione;

2-Amino-4-cyclopropyl-6-[3-(1,2-dihydroxyethyl)pyrrolidin-1-yl]-7-fluoro-5-methoxypyrido[1,2-c]pyrimidine-1,3-dione;

2-Amino-6-[3-(1-amino-2-hydroxyethyl)pyrrolidin-1-yl]-4-cyclopropyl-7-fluoro-5-methoxypyrido[1,2-c]pyrimidine-1,3-dione;

2-Amino-6-[3-(1-amino-2-hydroxyethyl)pyrrolidin-1-yl]-4-cyclopropyl-7-fluoro-5-methoxy-8-methylpyrido[1,2-c]pyrimidine-1,3-dione;

2-Amino-6-[3-(1-amino-2-hydroxyethyl)pyrrolidin-1-yl]-4-cyclopropyl-7-fluoro-5,8-dimethylpyrido[1,2-c]pyrimidine-1,3-dione;

2-Amino-6-[3-(1-amino-1-methylethyl)pyrrolidine-1-yl]-4-cyclopropyl-7-fluoro-5-methoxypyrido[1,2-c]pyrimidine-1,3-dione; and 6-Chloro-4-cyclopropyl-7-fluoro-5-methoxypyrido[1,2-c]pyrimidine-1,3-dione;

6-Chloro-4-cyclopropyl-7-fluoro-5-methoxy-8-methylpyrido[1,2-c]pyrimidine-1,3-dione;

6-Chloro-4-cyclopropyl-7-fluoro-5,8-dimethylpyrido[1,2-c]pyrimidine-1,3-dione;

2-Amino-6-chloro-4-cyclopropyl-7-fluoro-5-methoxypyrido[1,2-c]pyrimidine-1,3-dione;

2-Amino-6-chloro-4-cyclopropyl-7-fluoro-5-methoxy-8-methylpyrido[1,2-c]pyrimidine-1,3-dione;

2-Amino-6-chloro-4-cyclopropyl-7-fluoro-5,8-dimethylpyrido[1,2-c]pyrimidine-1,3-dione;

8-Amino-6-hloro-4-cyclopropyl-7-fluoro-5-methylpyrido[1,2-c]pyrimidine-1,3-dione;

2,8-Diamino-6-hloro-4-cyclopropyl-7-fluoro-5-methylpyrido[1,2-c]pyrimidine-1,3-dione;

or a pharmaceutically acceptable salt thereof.

16. A compound which is:

4-Cyclopropyl-7-fluoro-5-methyl-6-[3-(1-methylaminoethyl)pyrrolidin-1-yl]pyrido[1,2-c]pyrimidine-1,3-dione;

4-Cyclopropyl-7-fluoro-5-methyl-6-pyrrolidin-1-ylpyrido[1,2-c]pyrimidine-1,3-dione;

4-Cyclopropyl-7-fluoro-6-[3-(1-hydroxyethyl)pyrrolidin-1-yl-5-methylpyrido[1,2-c]pyrimidine-1,3-dione;

6-[(R)-3-((R)-1-Aminoethyl)-pyrrolidin-1-yl]-4-cyclopropyl-7-fluoro-5-methylpyrido[1,2-c]pyrimidine-1,3-dione hydrochloride;

6-[(R)-3-((S)-1-Aminoethyl)-pyrrolidin-1-yl]-4-cyclopropyl-7-fluoro-5-methylpyrido[1,2-c]pyrimidine-1,3-dione hydrochloride;

6-[4-(1-Aminoethyl)-3,3-dimethylpyrrolidin-1-yl]-4-cyclopropropyl-7-fluoro-5-methylpyrido[1,2-c]pyrimidine-1,3-dione hydrochloride;

6-(3-Aminopyrrolidin-1-yl)-4-cyclopropyl-7-fluoro-5-methyl-pyrido[1,2-c]pyrimidine-1,3-dione hydrochloride;

6-[3-(1-Aminoethyl)-4-methylpyrrolidin-1-yl]-4-cyclopropyl-7-fluoro-5-methylpyrido[1,2-c]pyrimidine-1,3-dione hydrochloride;

6-[3-(1-Amino-1-phenylmethyl)pyrrolidin-1-yl]-4-cyclopropyl-7-fluoro-5-methylpyrido[1,2-c]pyrimidine-1,3-dione;

6-{3-[1-Amino-1-(2-fluorophenyl)methyl]pyrrolidin-1-yl}-4-cyclopropyl-7-fluoro-5-methylpyrido[1,2-c]pyrimidine-1,3-dione;

6-{3-[1-Amino-1-(4-fluorophenyl)methyl]pyrrolidin-1-yl}-4-cyclopropyl-7-fluoro-5-methylpyrido[1,2-c]pyrimidine-1,3-dione;

6-{3-[1-Amino-1-(2,4-difluorophenyl)methyl]pyrrolidin-1-yl}-4-cyclopropyl-7-fluoro-5-methylpyrido[1,2-c]pyrimidine-1,3-dione;

6-{3-[1-Amino-1-(2,6-difluorophenyl)methyl]pyrrolidin-1-yl}-4-cyclopropyl-7-fluoro-5-methylpyrido[1,2-c]pyrimidine-1,3-dione;

6-{3-[1-Amino-1-(2,4,6-trifluorophenyl)methyl]pyrrolidin-1-yl}-4-cyclopropyl-7-fluoro-5-methylpyrido[1,2-c]pyrimidine-1,3-dione;

6-[3-(1-Aminopropyl)pyrrolidin-1-yl]-4-cyclopropyl-7-fluoro-5-methylpyrido[1,2-c]pyrimidine-1,3-dione;

6-[3-(1-Amino-2-methylpropyl)pyrrolidin-1-yl]-4-cyclopropyl-7-fluoro-5-methylpyrido[1,2-c]pyrimidine-1,3-dione;

6-[3-(1-Amino-2-cyclopropylmethyl)pyrrolidin-1-yl]4-cyclopropyl-7-fluoro-5-methylpyrido[1,2-c]pyrimidine-1,3-dione;

6-[3-(1-Aminocyclopropyl)pyrrolidin-1-yl]-4-cyclopropyl-7-fluoro-5-methylpyrido[1,2-c]pyrimidine-1,3-dione;

6-[3-(1-Aminocyclopropyl)-4-fluoropyrrolidin-1-yl]-4-cyclopropyl-7-fluoro-5-methylpyrido[1,2-c]pyrimidine-1,3-dione;

6-[3-(1-Amino-1-phenylmethyl)-4-fluoropyrrolidin-1-yl]-4-cyclopropyl-7-fluoro-5-methylpyrido[1,2-c]pyrimidine-1,3-dione;

6-[3-(1-Amino-2-fluoroethyl)pyrrolidin-1-yl]-4-cyclopropyl-7-fluoro-5-methylpyrido[1,2-c]pyrimidine-1,3-dione;

6-[3-(1-Amino-2,2-difluorocyclopropyl)pyrrolidin-1-yl]-4-cyclopropyl-7-fluoro-5-methylpyrido[1,2-c]pyrimidine-1,3-dione;

6-[3-(1-Aminoethyl)pyrrolidin-1-yl]-4-cyclopropyl-7-fluoro-5-methylpyrido[1,2-c]pyrimidine-1,3-dione;

6-[3-(1-Amino-2-fluorocyclopropyl)pyrrolidin-1-yl]-4-cyclopropyl-7-fluoro-5-methylpyrido[1,2-c]pyrimidine-1,3-dione;

6-[3-(1-Amino-1-methylethyl)pyrrolidin-1-yl]-4-cyclopropyl-7-fluoro-5-methylpyrido[1,2-c]pyrimidine-1,3-dione;

6-[3-(1-Aminoethyl)-4-fluoropyrrolidin-1-yl]-4-cyclopropyl-7-fluoro-5-methylpyrido[1,2-c]pyrimidine-1,3-dione;

6-[3-(1-Amino-1-pyridin-2-ylmethyl)pyrrolidin-1-yl]-4-cyclopropyl-7-fluoro-5-methylpyrido[1,2-c]pyrimidine-1,3-dione;

6-[3-(1-Amino-2-fluorocyclopropyl)-4-fluoropyrrolidin-1-yl]-4-cyclopropyl-7-fluoro-5-methylpyrido[1,2-c]pyrimidine-1,3-dione;

6-[3-(1-Amino-1-pyridin-3-ylmethyl)pyrrolidin-1-yl]-4-cyclopropyl-7-fluoro-5-methylpyrido[1,2-c]pyrimidine-1,3-dione;

6-[3-(1-Amino-1-pyridin-4-ylmethyl)pyrrolidin-1-yl]-4-cyclopropyl-7-fluoro-5-methylpyrido[1,2-c]pyrimidine-1,3-dione;

6-(4-Aminohexahydrocyclopenta[c]pyrrol-2-yl)-4-cyclopropyl-7-fluoro-5-methylpyrido[1,2-c]pyrimidine-1,3-dione;

6-(4-Amino-5-fluorohexahydrocyclopenta[c]pyrrol-2-yl)-4-cyclopropyl-7-fluoro-5-methylpyrido[1,2-c]pyrimidine-1,3-dione;

4-Cyclopropyl-7-fluoro-5-methyl-6-(3-phenylpyrrolidin-1-yl)pyrido[1,2-c]pyrimidine-1,3-dione;

4-Cyclopropyl-7-fluoro-5-methyl-6-(3-pyridin-2-ylpyrrolidin-1-yl)pyrido[1,2-c]pyrimidine-1,3-dione;

4-Cyclopropyl-7-fluoro-5-methyl-6-(3-pyridin-3-ylpyrrolidin-1-yl)pyrido[1,2-c]pyrimidine-1,3-dione;

4-Cyclopropyl-7-fluoro-5-methyl-6-(3-pyridin-4-ylpyrrolidin-1-yl)pyrido[1,2-c]pyrimidine-1,3-dione;

4-Cyclopropyl-7-fluoro-5-methyl-6-(piperazin-1-yl)pyrido[1,2-c]pyrimidine-1,3-dione;

4-Cyclopropyl-7-fluoro-5-methyl-6-(4-methylpiperazin-1-yl)pyrido[1,2-c]pyrimidine-1,3-dione;

N-{1-[1-(4-Cyclopropyl-7-fluoro-5-methyl-1,3-dioxo-2,3-dihydro-1H-pyrido[1,2-c]pyrimidin-6-yl)pyrrolidin-3-yl]ethyl}methanesulfonamide;
4-Cyclopropyl-7-fluoro-5-methyl-6(octahydropyrrolo[3,4-b]pyridin-6-yl)pyrido[1,2-c]pyrimidine-1,3-dione;
6-(7-Amino-5-azaspiro[2.4]hept-5-yl)-4-cyclopropyl-7-fluoro-5-methylpyrido[1,2-c]pyrimidine-1,3-dione;
4-Cyclopropyl-7-fluoro-5-methyl-6-(thiophen-3-yl)pyrido[1,2-c]pyrimidine-1,3-dione;
4-Cyclopropyl-7-fluoro-5-methyl-6-(1-methyl-2,3-dihydro-1H-isoindol-5-yl)pyrido[1,2-c]pyrimidine-1,3-dione;
4-Cyclopropyl-7-fluoro-6-(7-hydroxymethyl-5-azaspiro[2.4]hept-5-yl)-5-methylpyrido[1,2-c]pyrimidine-1,3-dione;
6-(3-Amino-4-methoxyiminopyrrolidin-1-yl)-4-cyclopropyl-7-fluoro-5-methylpyrido[1,2-c]pyrimidine-1,3-dione;
4-cyclopropyl-7-fluoro-5-methyl-6-(3-methylaminomethylpyrrolidin-1-yl)pyrido[1,2-c]pyrimidine-1,3-dione;
6-(5-Aminomethylthiophen-3-yl)-4-cyclopropyl-7-fluoro-5-methylpyrido[1,2-c]pyrimidine-1,3-dione;
6-[3-(1-Aminoethyl)-3-fluoropyrrolidin-1-yl]-4-cyclopropyl-7-fluoro-5-methylpyrido[1,2-c]pyrimidine-1,3-dione;
6-(5-Aminomethylthiophen-3-yl)-4-cyclopropyl-7-fluoro-5-methylpyrido[1,2-c]pyrimidine-1,3-dione;
6-(5-Aminomethylthiophen-2-yl)-4-cyclopropyl-7-fluoro-5-methylpyrido[1,2-c]pyrimidine-1,3-dione;
6-(4-Aminomethylthiophen-2-yl)-4-cyclopropyl-7-fluoro-5-methylpyrido[1,2-c]pyrimidine-1,3-dione;
6-(4-Aminomethylthiophen-3-yl)-4-cyclopropyl-7-fluoro-5-methylpyrido[1,2-c]pyrimidine-1,3-dione;
4-Cyclopropyl-6-(5,6-dihydro-4H-thieno[2,3-c]pyrrol-3-yl)-7-fluoro-5-methylpyrido[1,2-c]pyrimidine-1,3-dione;
4-Cyclopropyl-6-(5,6-dihydro-4H-thieno[2,3-c]pyrrol-2-yl)-7-fluoro-5-methylpyrido[1,2-c]pyrimidine-1,3-dione;
4-Cyclopropyl-7-fluoro-5-methyl-6-(6-methyl-5,6-dihydro-4H-thieno[2,3-c]pyrrol-2-yl)pyrido[1,2-c]pyrimidine-1,3-dione;
4-Cyclopropyl-7-fluoro-5-methyl-6-(6-methyl-5,6-dihydro-4H-thieno[2,3-c]pyrrol-3-yl)pyrido[1,2-c]pyrimidine-1,3-dione;
4-Cyclopropyl-7-fluoro-5-methyl-6-(5-pyridin-4-ylthiophen-3-yl)pyrido[1,2-c]pyrimidine-1,3-dione;
4-Cyclopropyl-7-fluoro-5-methyl-6-(5-pyridin-3-ylthiophen-3-yl)pyrido[1,2-c]pyrimidine-1,3-dione;
4-Cyclopropyl-7-fluoro-5-methyl-6-(5-pyridin-2-ylthiophen-3-yl)pyrido[1,2-c]pyrimidine-1,3-dione;
4-Cyclopropyl-7-fluoro-5-methyl-6-(4-pyridin-4-ylthiophen-3-yl)pyrido[1,2-c]pyrimidine-1,3-dione;
4-Cyclopropyl-7-fluoro-5-methyl-6-(4-pyridin-3-ylthiophen-3-yl)pyrido[1,2-c]pyrimidine-1,3-dione;
4-Cyclopropyl-7-fluoro-5-methyl-6-(4-pyridin-2-ylthiophen-3-yl)pyrido[1,2-c]pyrimidine-1,3-dione;
4-Cyclopropyl-7-fluoro-5-methyl-6-pyridin-4-ylpyrido[1,2-c]pyrimidine-1,3-dione;
6-(4-Aminomethylpyridin-2-yl]-4-cyclopropyl-7-fluoro-5-methylpyrido[1,2-c]pyrimidine-1,3-dione;
6-(5-Aminomethylpyridin-2-yl]-4-cyclopropyl-7-fluoro-5-methylpyrido[1,2-c]pyrimidine-1,3-dione;
6-(6-Aminomethylpyridin-2-yl]-4-cyclopropyl-7-fluoro-5-methylpyrido[1,2-c]pyrimidine-1,3-dione;
6-(5-Aminomethylpyrimidin-2-yl]-4-cyclopropyl-7-fluoro-5-methylpyrido[1,2-c]pyrimidine-1,3-dione;
4-Cyclopropyl-7-fluoro-5-methyl-6-pyrimidin-2-ylpyrido[1,2-c]pyrimidine-1,3-dione;
6-(2-Aminomethylpyrimidin-5-yl]-4-cyclopropyl-7-fluoro-5-methylpyrido[1,2-c]pyrimidine-1,3-dione;
4-Cyclopropyl-7-fluoro-5-methyl-6-pyrimidin-5-ylpyrido[1,2-c]pyrimidine-1,3-dione;
4-Cyclopropyl-7-fluoro-5-methyl-6-pyrazin-2-ylpyrido[1,2-c]pyrimidine-1,3-dione;
6-(6-Aminomethylpyrazin-2-yl]-4-cyclopropyl-7-fluoro-5-methylpyrido[1,2-c]pyrimidine-1,3-dione;
6-[3-(6-Aminomethylpyridin-2-yl)pyrrolidin-1-yl]-4-cyclopropyl-7-fluoro-5-methylpyrido[1,2-c]pyrimidine-1,3-dione;
6-[3-(2-Aminomethylpyridin-3-yl)pyrrolidin-1-yl]-4-cyclopropyl-7-fluoro-5-methylpyrido[1,2-c]pyrimidine-1,3-dione;
6-[5-(2-Aminomethylpyridin-3-yl)thiophen-3-yl]-4-cyclopropyl-7-fluoro-5-methylpyrido[1,2-c]pyrimidine-1,3-dione;
6-[5-(2-Aminomethylpyridin-3-yl)thiophen-2-yl]-4-cyclopropyl-7-fluoro-5-methylpyrido[1,2-c]pyrimidine-1,3-dione;
6-[5-(6-Aminomethylpyridin-2-yl)thiophen-2-yl]-4-cyclopropyl-7-fluoro-5-methylpyrido[1,2-c]pyrimidine-1,3-dione;
6-[5-(6-Aminomethylpyridin-2-yl)thiophen-3-yl]-4-cyclopropyl-7-fluoro-5-methylpyrido[1,2-c]pyrimidine-1,3-dione;
6-[4-(2-Aminomethylpyridin-3-yl)thiophen-2-yl]-4-cyclopropyl-7-fluoro-5-methylpyrido[1,2-c]pyrimidine-1,3-dione;
6-[3-(2-Aminomethylpyridin-3-yl)thiophen-2-yl]-4-cyclopropyl-7-fluoro-5-methylpyrido[1,2-c]pyrimidine-1,3-dione;
6-[4-(6-Aminomethylpyridin-2-yl)thiophen-3-yl]-4-cyclopropyl-7-fluoro-5-methylpyrido[1,2-c]pyrimidine-1,3-dione;
4-Cyclopropyl-7-fluoro-5-methyl-6-(4-pyridin-4-ylthiophen-2-yl)pyrido[1,2-c]pyrimidine-1,3-dione; and
6-[4-(1-Aminoethyl)thiophen-2-yl]-4-cyclopropyl-7-fluoro-5-methylpyrido[1,2-c]pyrimidine-1,3-dione;
4-Cyclopropyl-7-fluoro-5-methoxy-6-[3-(1-methylaminoethyl)pyrrolidin-1-yl]pyrido[1,2-c]pyrimidine-1,3-dione;
4-Cyclopropyl-7-fluoro-5-methoxy-6-pyrrolidin-1-ylpyrido[1,2-c]pyrimidine-1,3-dione;
4-Cyclopropyl-7-fluoro-6-[3-(1-hydroxyethyl)pyrrolidin-1-yl-5-methoxypyrido[1,2-c]pyrimidine-1,3-dione;
6-[(R)-3-((R)-1-Aminoethyl)-pyrrolidin-1-yl]-4-cyclopropyl-7-fluoro-5-methoxypyrido[1,2-c]pyrimidine-1,3-dione;
6-[(R)-3-((S)-1-Aminoethyl)-pyrrolidin-1-yl]-4-cyclopropyl-7-fluoro-5-methoxypyrido[1,2-c]pyrimidine-1,3-dione;
6-[4-(1-Aminoethyl)-3,3-dimethylpyrrolidin-1-yl]-4-cyclopropropyl-7-fluoro-5-methoxypyrido[1,2-c]pyrimidine-1,3-dione;

6-(3-Aminopyrrolidin-1-yl)-4-cyclopropyl-7-fluoro-5-methoxypyrido[1,2-c]pyrimidine-1,3-dione;

6-[3-(1-Aminoethyl)-4-methylpyrrolidin-1-yl]-4-cyclopropyl-7-fluoro-5-methoxypyrido[1,2-c]pyrimidine-1,3-dione;

6-[3-(1-Amino-1-phenylmethyl)pyrrolidin-1-yl]-4-cyclopropyl-7-fluoro-5-methoxypyrido[1,2-c]pyrimidine-1,3-dione;

6-{3-[1-Amino-1-(2-fluorophenyl)methyl]pyrrolidin-1-yl}-4-cyclopropyl-7-fluoro-5-methoxypyrido[1,2-c]pyrimidine-1,3-dione;

6-{3-[1-Amino-1-(4-fluorophenyl)methyl]pyrrolidin-1-yl}-4-cyclopropyl-7-fluoro-5-methoxypyrido[1,2-c]pyrimidine-1,3-dione;

6-{3-[1-Amino-1-(2,4-difluorophenyl)methyl]pyrrolidin-1-yl}-4-cyclopropyl-7-fluoro-5-methoxypyrido[1,2-c]pyrimidine-1,3-dione;

6-{3-[1-Amino-1-(2,6-difluorophenyl)methyl]pyrrolidin-1-yl}-4-cyclopropyl-7-fluoro-5-methoxypyrido[1,2-c]pyrimidine-1,3-dione;

6-{3-[1-Amino-1-(2,4,6-trifluorophenyl)methyl]pyrrolidin-1-yl}-4-cyclopropyl-7-fluoro-5-methoxypyrido[1,2-c]pyrimidine-1,3-dione;

6-[3-(1-Aminopropyl)pyrrolidin-1-yl]-4-cyclopropyl-7-fluoro-5-methoxypyrido[1,2-c]pyrimidine-1,3-dione;

6-[3-(1-Amino-2-methylpropyl)pyrrolidin-1-yl]-4-cyclopropyl-7-fluoro-5-methoxypyrido[1,2-c]pyrimidine-1,3-dione;

6-[3-(1-Amino-2-cyclopropylmethyl)pyrrolidin-1-yl]-4-cyclopropyl-7-fluoro-5-methoxypyrido[1,2-c]pyrimidine-1,3-dione;

6-[3-(1-Aminocyclopropyl)pyrrolidin-1-yl]-4-cyclopropyl-7-fluoro-5-methoxypyrido[1,2-c]pyrimidine-1,3-dione;

6-[3-(1-Aminocyclopropyl)-4-fluoropyrrolidin-1-yl]-4-cyclopropyl-7-fluoro-5-methoxypyrido[1,2-c]pyrimidine-1,3-dione;

6-[3-(1-Amino-1-phenylmethyl)-4-fluoropyrrolidin-1-yl]-4-cyclopropyl-7-fluoro-5-methoxypyrido[1,2-c]pyrimidine-1,3-dione;

6-[3-(1-Amino-2-fluoroethyl)pyrrolidin-1-yl]-4-cyclopropyl-7-fluoro-5-methoxypyrido[1,2-c]pyrimidine-1,3-dione;

6-[3-(1-Amino-2,2-difluorocyclopropyl)pyrrolidin-1-yl]-4-cyclopropyl-7-fluoro-5-methoxypyrido[1,2-c]pyrimidine-1,3-dione;

6-[3-(1-Aminoethyl)pyrrolidin-1-yl]-4-cyclopropyl-7-fluoro-5-methoxypyrido[1,2-c]pyrimidine-1,3-dione;

6-[3-(1-Amino-2-fluorocyclopropyl)pyrrolidin-1-yl]-4-cyclopropyl-7-fluoro-5-methoxypyrido[1,2-c]pyrimidine-1,3-dione;

6-[3-(1-Amino-1-methylethyl)pyrrolidin-1-yl]-4-cyclopropyl-7-fluoro-5-methoxypyrido[1,2-c]pyrimidine-1,3-dione;

6-[3-(1-Aminoethyl)-4-fluoropyrrolidin-1-yl]-4-cyclopropyl-7-fluoro-5-methoxypyrido[1,2-c]pyrimidine-1,3-dione;

6-[3-(1-Amino-1-pyridin-2-ylmethyl)pyrrolidin-1-yl]-4-cyclopropyl-7-fluoro-5-methoxypyrido[1,2-c]pyrimidine-1,3-dione;

6-[3-(1-Amino-2-fluorocyclopropyl)-4-fluoropyrrolidin-1-yl]-4-cyclopropyl-7-fluoro-5-methoxypyrido[1,2-c]pyrimidine-1,3-dione;

6-[3-(1-Amino-1-pyridin-3-ylmethyl)pyrrolidin-1-yl]-4-cyclopropyl-7-fluoro-5-methoxypyrido[1,2-c]pyrimidine-1,3-dione;

6-[3-(1-Amino-1-pyridin-4-ylmethyl)pyrrolidin-1-yl]-4-cyclopropyl-7-fluoro-5-methoxypyrido[1,2-c]pyrimidine-1,3-dione;

6-(4-Aminohexahydrocyclopenta[c]pyrrol-2-yl)-4-cyclopropyl-7-fluoro-5-methoxypyrido[1,2-c]pyrimidine-1,3-dione;

6-(4-Amino-5-fluorohexahydrocyclopenta[c]pyrrol-2-yl)-4-cyclopropyl-7-fluoro-5-methoxypyrido[1,2-c]pyrimidine-1,3-dione;

4-Cyclopropyl-7-fluoro-5-methoxy-6-(3-phenylpyrrolidin-1-yl)pyrido[1,2-c]pyrimidine-1,3-dione;

4-Cyclopropyl-7-fluoro-5-methoxy-6-(3-pyridin-2-ylpyrrolidin-1-yl)pyrido[1,2-c]pyrimidine-1,3-dione;

4-Cyclopropyl-7-fluoro-5-methoxy-6-(3-pyridin-3-ylpyrrolidin-1-yl)pyrido[1,2-c]pyrimidine-1,3-dione;

4-Cyclopropyl-7-fluoro-5-methoxy-6-(3-pyridin-4-ylpyrrolidin-1-yl)pyrido[1,2-c]pyrimidine-1,3-dione;

4-Cyclopropyl-7-fluoro-5-methoxy-6-(piperazin-1-yl)pyrido[1,2-c]pyrimidine-1,3-dione;

4-Cyclopropyl-7-fluoro-5-methoxy-6-(4-methylpiperazin-1-yl)pyrido[1,2-c]pyrimidine-1,3-dione;

N-{1-[1-(4-Cyclopropyl-7-fluoro-5-methoxy-1,3-dioxo-2,3-dihydro-1H-pyrido[1,2-c]pyrimidin-6-yl)pyrrolidin-3-yl]ethyl}methanesulfonamide, 4-Cyclopropyl-7-fluoro-5-methoxy-6(octahydropyrrolo[3,4-b]pyridin-6-yl)pyrido[1,2-c]pyrimidine-1,3-dione;

6-(7-Amino-5-azaspiro[2.4]hept-5-yl)-4-cyclopropyl-7-fluoro-5-methoxypyrido[1,2-c]pyrimidine-1,3-dione;

4-Cyclopropyl-7-fluoro-5-methoxy-6-(thiophen-3-yl)pyrido[1,2-c]pyrimidine-1,3-dione;

4-Cyclopropyl-7-fluoro-5-methoxy-6-(1-methyl-2,3-dihydro-1H-isoindol-5-yl)pyrido[1,2-c]pyrimidine-1,3-dione;

4-Cyclopropyl-7-fluoro-6-(7-hydroxymethyl-5-azaspiro[2.4]hept-5-yl)-5-methoxypyrido[1,2-c]pyrimidine-1,3-dione;

6-(3-Amino-4-methoxyiminopyrrolidin-1-yl)-4-cyclopropyl-7-fluoro-5-methoxypyrido[1,2-c]pyrimidine-1,3-dione;

4-cyclopropyl-7-fluoro-5-methoxy-6-(3-methylaminomethylpyrrolidin-1-yl)pyrido[1,2-c]pyrimidine-1,3-dione;

6-(5-Aminomethylthiophen-3-yl)-4-cyclopropyl-7-fluoro-5-methoxypyrido[1,2-c]pyrimidine-1,3-dione;

6-[3-(1-Aminoethyl)-3-fluoropyrrolidin-1-yl]-4-cyclopropyl-7-fluoro-5-methoxypyrido[1,2-c]pyrimidine-1,3-dione;

6-(5-Aminomethylthiophen-3-yl]-4-cyclopropyl-7-fluoro-5-methoxypyrido[1,2-c]pyrimidine-1,3-dione;

6-(5-Aminomethylthiophen-2-yl]-4-cyclopropyl-7-fluoro-5-methoxypyrido[1,2-c]pyrimidine-1,3-dione;

6-(4-Aminomethylthiophen-2-yl]-4-cyclopropyl-7-fluoro-5-methoxypyrido[1,2-c]pyrimidine-1,3-dione;

6-(4-Aminomethylthiophen-3-yl]-4-cyclopropyl-7-fluoro-5-methoxypyrido[1,2-c]pyrimidine-1,3-dione;

4-Cyclopropyl-6-(5,6-dihydro-4H-thieno[2,3-c]pyrrol-3-yl)-7-fluoro-5-methoxypyrido[1,2-c]pyrimidine-1,3-dione;

4-Cyclopropyl-6-(5,6-dihydro-4H-thieno[2,3-c]pyrrol-2-yl)-7-fluoro-5-methoxypyrido[1,2-c]pyrimidine-1,3-dione;

4-Cyclopropyl-7-fluoro-5-methoxy-6-(6-methyl-5,6-dihydro-4H-thieno[2,3-c]pyrrol-2-yl)pyrido[1,2-c]pyrimidine-1,3-dione;

4-Cyclopropyl-7-fluoro-5-methoxy-6-(6-methyl-5,6-dihydro-4H-thieno[2,3-c]pyrrol-3-yl)pyrido[1,2-c]pyrimidine-1,3-dione;

4-Cyclopropyl-7-fluoro-5-methoxy-6-(5-pyridin-4-ylthiophen-3-yl)pyrido[1,2-c]pyrimidine-1,3-dione;

4-Cyclopropyl-7-fluoro-5-methoxy-6-(5-pyridin-3-ylthiophen-3-yl)pyrido[1,2-c]pyrimidine-1,3-dione;

4-Cyclopropyl-7-fluoro-5-methoxy-6-(5-pyridin-2-ylthiophen-3-yl)pyrido[1,2-c]pyrimidine-1,3-dione;

4-Cyclopropyl-7-fluoro-5-methoxy-6-(4-pyridin-4-ylthiophen-3-yl)pyrido[1,2-c]pyrimidine-1,3-dione;

4-Cyclopropyl-7-fluoro-5-methoxy-6-(4-pyridin-3-ylthiophen-3-yl)pyrido[1,2-c]pyrimidine-1,3-dione;

4-Cyclopropyl-7-fluoro-5-methoxy-6-(4-pyridin-2-ylthiophen-3-yl)pyrido[1,2-c]pyrimidine-1,3-dione;

4-Cyclopropyl-7-fluoro-5-methoxy-6-pyridin-4-ylpyrido[1,2-c]pyrimidine-1,3-dione;

6-(4-Aminomethylpyridin-2-yl)-4-cyclopropyl-7-fluoro-5-methoxypyrido[1,2-c]pyrimidine-1,3-dione;

6-(5-Aminomethylpyridin-2-yl)-4-cyclopropyl-7-fluoro-5-methoxypyrido[1,2-c]pyrimidine-1,3-dione;

6-(6-Aminomethylpyridin-2-yl)-4-cyclopropyl-7-fluoro-5-methoxypyrido[1,2-c]pyrimidine-1,3-dione;

6-(5-Aminomethylpyrimidin-2-yl)-4-cyclopropyl-7-fluoro-5-methoxypyrido[1,2-c]pyrimidine-1,3-dione;

4-Cyclopropyl-7-fluoro-5-methoxy-6-pyrimidin-2-ylpyrido[1,2-c]pyrimidine-1,3-dione;

6-(2-Aminomethylpyrimidin-5-yl)-4-cyclopropyl-7-fluoro-5-methoxypyrido[1,2-c]pyrimidine-1,3-dione;

4-Cyclopropyl-7-fluoro-5-methoxy-6-pyrimidin-5-ylpyrido[1,2-c]pyrimidine-1,3-dione;

4-Cyclopropyl-7-fluoro-5-methoxy-6-pyrazin-2-ylpyrido[1,2-c]pyrimidine-1,3-dione;

6-(6-Aminomethylpyrazin-2-yl]-4-cyclopropyl-7-fluoro-5-methoxypyrido[1,2-c]pyrimidine-1,3-dione;

6-[3-(6-Aminomethylpyridin-2-yl)pyrrolidin-1-yl]-4-cyclopropyl-7-fluoro-5-methoxypyrido[1,2-c]pyrimidine-1,3-dione;

6-[3-(2-Aminomethylpyridin-3-yl)pyrrolidin-1-yl]-4-cyclopropyl-7-fluoro-5-methoxypyrido[1,2-c]pyrimidine-1,3-dione;

6-[5-(2-Aminomethylpyridin-3-yl)thiophen-3-yl]-4-cyclopropyl-7-fluoro-5-methoxypyrido[1,2-c]pyrimidine-1,3-dione;

6-[5-(2-Aminomethylpyridin-3-yl)thiophen-2-yl]-4-cyclopropyl-7-fluoro-5-methoxypyrido[1,2-c]pyrimidine-1,3-dione;

6-[5-(6-Aminomethylpyridin-2-yl)thiophen-2-yl]-4-cyclopropyl-7-fluoro-5-methoxypyrido[1,2-c]pyrimidine-1,3-dione;

6-[5-(6-Aminomethylpyridin-2-yl)thiophen-3-yl]-4-cyclopropyl-7-fluoro-5-methoxypyrido[1,2-c]pyrimidine-1,3-dione;

6-[4-(2-Aminomethylpyridin-3-yl)thiophen-2-yl]-4-cyclopropyl-7-fluoro-5-methoxypyrido[1,2-c]pyrimidine-1,3-dione;

6-[3-(2-Aminomethylpyridin-3-yl)thiophen-2-yl]-4-cyclopropyl-7-fluoro-5-methoxypyrido[1,2-c]pyrimidine-1,3-dione;

6-[4-(6-Aminomethylpyridin-2-yl)thiophen-3-yl]-4-cyclopropyl-7-fluoro-5-methoxypyrido[1,2-c]pyrimidine-1,3-dione;

6-[3-(1-Aminoethyl)pyrrolidin-1-yl]-4-cyclopropyl-7-fluoro-5,8-dimethylpyrido[1,2-c]pyrimidine-1,3-dione;

6-[3-(1-Aminoethyl)pyrrolidin-1-yl]-4-cyclopropyl-7-fluoro-5-methoxy-8-methylpyrido[1,2-c]pyrimidine-1,3-dione;

8-Amino-6-[3-(1-aminoethyl)pyrrolidin-1-yl]-4-cyclopropyl-7-fluoro-5-methylpyrido[1,2-c]pyrimidine-1,3-dione;

8-Amino-6-(3-aminomethyl-4-fluoropyrrolidin-1-yl)-4-cyclopropyl-7-fluoro-5-methylpyrido[1,2-c]pyrimidine-1,3-dione;

6-(3-Aminomethyl-4-fluoropyrrolidin-1-yl)-4-cyclopropyl-7-fluoro-5,8-dimethylpyrido[1,2-c]pyrimidine-1,3-dione;

6-[3-(1-Amino-2,2-difluoroethyl)pyrrolidin-1-yl]-4-cyclopropyl-7-fluoro-5,8-dimethylpyrido[1,2-c]pyrimidine-1,3-dione;

6-[3-(1-Amino-2,2-difluoroethyl)pyrrolidin-1-yl]-4-cyclopropyl-7-fluoro-5-methoxy-8-methylpyrido[1,2-c]pyrimidine-1,3-dione;

6-(4-Aminomethyl-4,5,6,7-tetrahydrobenzo[b]thiophen-2-yl)-4-cyclopropyl-7-fluoro-5-methoxy-8-methylpyrido[1,2-c]pyrimidine-1,3-dione;

6-(4-Aminomethyl-4,5,6,7-tetrahydrobenzo[b]thiophen-2-yl)-4-cyclopropyl-7-fluoro-5,8-dimethylpyrido[1,2-c]pyrimidine-1,3-dione;

6-(4-Aminomethyl-4,5,6,7-tetrahydrobenzo[b]thiophen-2-yl)-4-cyclopropyl-7-fluoro-5-methylpyrido[1,2-c]pyrimidine-1,3-dione;

4-Cyclopropyl-6-[3-(1,2-dihydroxyethyl)pyrrolidin-1-yl]-7-fluoro-5-methoxy-8-methylpyrido[1,2-c]pyrimidine-1,3-dione;

4-Cyclopropyl-6-[3-(1,2-dihydroxyethyl)pyrrolidin-1-yl]-7-fluoro-5,8-dimethylpyrido[1,2-c]pyrimidine-1,3-dione;

4-Cyclopropyl-6-[3-(1,2-dihydroxyethyl)pyrrolidin-1-yl]-7-fluoro-5-methylpyrido[1,2-c]pyrimidine-1,3-dione;

4-Cyclopropyl-6-[3-(1,2-dihydroxyethyl)pyrrolidin-1-yl]-7-fluoro-5-methoxypyrido[1,2-c]pyrimidine-1,3-dione;

6-[3-(1-Amino-2-hydroxyethyl)pyrrolidin-1-yl]-4-cyclopropyl-7-fluoro-5-methoxypyrido[1,2-c]pyrimidine-1,3-dione;

6-[3-(1-Amino-2-hydroxyethyl)pyrrolidin-1-yl]-4-cyclopropyl-7-fluoro-5-methoxy-8-methylpyrido[1,2-c]pyrimidine-1,3-dione;

6-[3-(1-Amino-2-hydroxyethyl)pyrrolidin-1-yl]-4-cyclopropyl-7-fluoro-5,8-dimethylpyrido[1,2-c]pyrimidine-1,3-dione;

4-Cyclopropyl-7-fluoro-5-methoxy-6-(4-pyridin-4-ylthiophen-2-yl)pyrido[1,2-c]pyrimidine-1,3-dione;

6-[4-(1-Aminoethyl)thiophen-2-yl]-4-cyclopropyl-7-fluoro-5-methoxypyrido[1,2-c]pyrimidine-1,3-dione; or a pharmaceutically acceptable salt thereof.

17. A process for preparing a compound of claim 1, wherein $R_2$ is H or $NH_2$, comprising:

(a) reacting amide 2 with a carbon monoxide equivalent which is phosgene to form bicyclic compound 3;

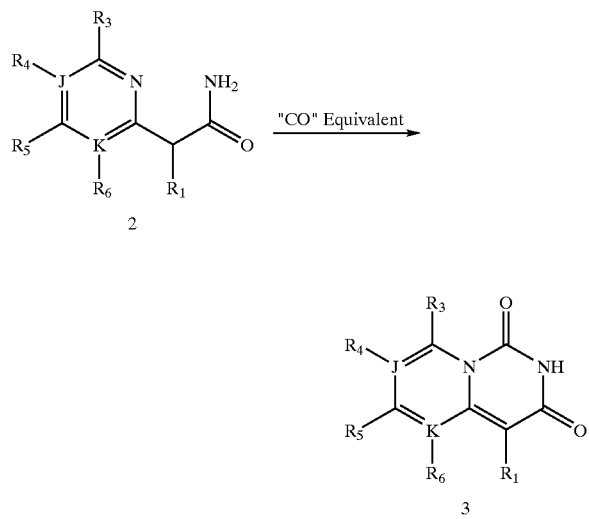

wherein J and K are C;

(b) coupling an amine to bicyclic compound 3 to form compound C1;

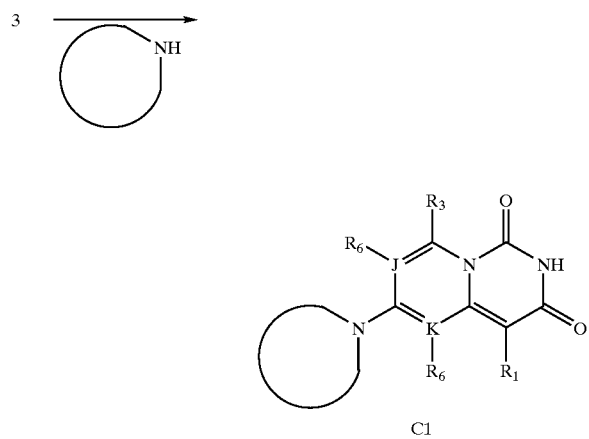

and optionally (c) aminating bicyclic compound 3 to form compound B1

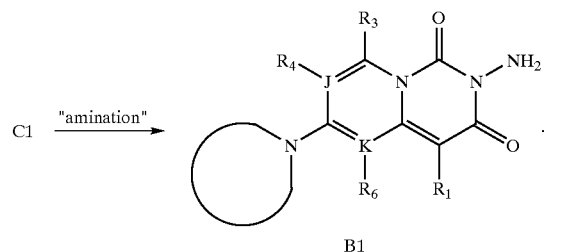

18. A process for preparing a compound of claim 1, wherein $R_2$ is H or $NH_2$ and $R_6$ is $C_1$–$C_7$ alkalkoxy and substituted alkoxy, comprising:

(a) reacting substituted pyridine compound 6 with hydrazine to from hydrazine derivative 7;

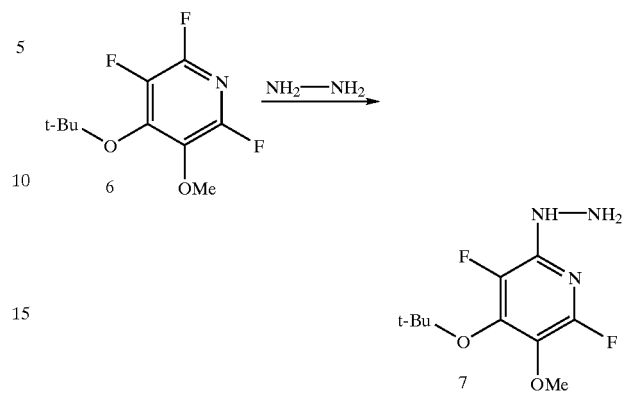

(b) reacting hydrazine derivative 7 with oxygen in the presence of base to form compound 8;

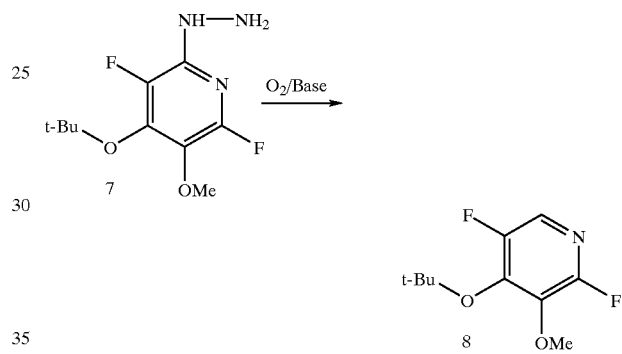

(c) reacting compound 8 with the anion of cyclopropyl acetonitrile to form compound 9;

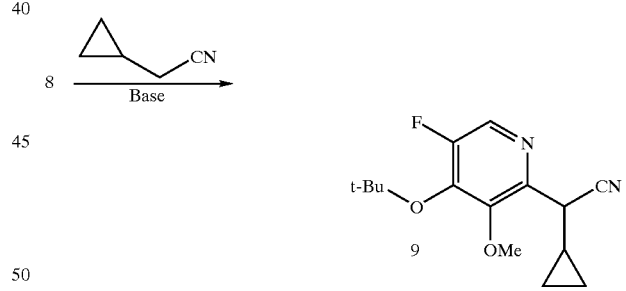

(d) reacting compound 9 with acid in the presence of a halo or triflate source "X" to form halo or triflate compound 10;

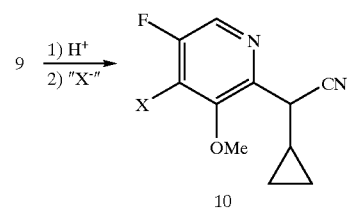

(e) converting the nitrile moiety in compound 10 to an amide and cyclizing according to step a of claim 17.

19. A pharmaceutical composition comprising a compound of claim 1 or 9, admixed with a carrier, diluent, or excipient.

20. A method of treating a bacterial infection in a mammal comprising administering to the mammal in need thereof an antibacterial effective amount of a compound claim 1 or 9.

21. A method of inhibiting a bacterial topoisomerase in a mammal comprising administering to the mammal in need thereof an effective amount of a compound claim 1 or 9.

22. A method of inhibiting a bacterial DNA gyrase in a mammal comprising administering to the mammal in need thereof an effective amount of a compound claim 1 or 9.

23. A method of inhibiting a bacterial topoisomerase IV in a mammal comprising administering to the mammal in need thereof an effective amount of a compound claim 1 or 9.

24. A method of inhibiting a quinolone resistant bacteria in a mammal comprising administering to the mammal an effective amount of a compound of claim 1 or 9.

25. A method of inhibiting a quinolone resistant DNA gyrase in a mammal comprising administering to the mammal an effective amount of a compound of claim 1 or 9.

26. A method of inhibiting a quinolone resistant topoisomerase in a mammal comprising administering to the mammal an effective amount of a compound of claim 1 or 9.

* * * * *